US009090897B2

(12) United States Patent
Hochrein

(10) Patent No.: US 9,090,897 B2
(45) Date of Patent: Jul. 28, 2015

(54) PRODUCTION OF IFN-LAMBDA BY CONVENTIONAL DENDRITIC CELLS

(75) Inventor: Hubertus Hochrein, Munich (DE)

(73) Assignee: Bavarian Nordic A/S, Kvistgaard (DK)

( * ) Notice: Subject to any disclaimer, the term of this patent is extended or adjusted under 35 U.S.C. 154(b) by 90 days.

(21) Appl. No.: 13/516,670

(22) PCT Filed: Dec. 17, 2010

(86) PCT No.: PCT/EP2010/007751
§ 371 (c)(1),
(2), (4) Date: Jun. 15, 2012

(87) PCT Pub. No.: WO2011/072871
PCT Pub. Date: Jun. 23, 2011

(65) Prior Publication Data
US 2012/0258082 A1 Oct. 11, 2012

Related U.S. Application Data

(60) Provisional application No. 61/287,777, filed on Dec. 18, 2009.

(30) Foreign Application Priority Data

May 21, 2010 (EP) .................................. 10005348

(51) Int. Cl.
A01N 63/00 (2006.01)
A61K 45/00 (2006.01)
C12P 21/00 (2006.01)
C07K 14/53 (2006.01)
C07K 14/555 (2006.01)
C12N 15/117 (2010.01)
A61K 35/15 (2015.01)

(52) U.S. Cl.
CPC .............. *C12N 15/117* (2013.01); *A61K 35/15* (2013.01); *C12N 2310/17* (2013.01)

(58) Field of Classification Search
CPC .. C12N 15/117; C12N 2310/17; C07K 14/53; A61K 38/193; A61K 35/15
See application file for complete search history.

(56) References Cited

U.S. PATENT DOCUMENTS

2008/0267994 A1* 10/2008 Hochrein et al. .......... 424/204.1

FOREIGN PATENT DOCUMENTS

| WO | WO 94/28391 A1 | 12/1994 |
| WO | WO 2004/060319 A2 | 7/2004 |
| WO | WO 2006/054177 A1 | 5/2006 |
| WO | WO 2008/131926 A1 | 11/2008 |
| WO | WO 2009/088401 A2 | 7/2009 |

OTHER PUBLICATIONS

N. Ank et al., "An Important Role for Type III Interferon (IFN-λ/IL-28) in TLR-Induced Antiviral Activity," *J. Immunol.* 180:2474-2485 (2008).
S.S. Diebold et al., "Role of TLR3 in the immunogenicity of replicon plasmid-based vaccines," *Gene Ther.* 16:359-366 (2009).
Extended European Search Report for EP Application No. 10005348. 7, issued Nov. 9, 2010.
T. Fujimura et al., "Inhibitory effect of the polyinosinic-polycytidylic acid/cationic liposome on the progression of murine B16F10 melanoma," *Eur. J. Immunol.* 36:3371-3380 (2006).
T.K. Ghosh et al., "TLR-TLR cross talk in human PBMC resulting in synergistic and antagonistic regulation of type-1 and 2 interferons, IL-12, and TNF-α," *Int'l Immunopharmacol.* 7:1111-1121 (2007).
C.S. Higano et al., "Safety and Biological Activity of Repeated Doses of Recombinant Human Flt3 Ligand in Patients with Bone Scan-Negative Hormone-Refractory Prostate Cancer," *Clin. Cancer Res.* 10:1219-1225 (2004).
X.-L. Huang et al., "Maturation of dendritic cells for enhanced activation of anti-HIV-1 CD8+ T cell immunity," *J. Leukoc. Biol.* 83:1530-1540 (2008).
International Search Report for International Application No. PCT/EP2010/007751, issued Mar. 9, 2011.
Q. Jiang et al., "IFN-producing Killer Dendritic Cells Contribute to the Inhibitory Effect of Poly I:C on the Progression of Murine Melanoma," *J. Immunother.* 31:555-562 (2008).
H. Lauterbach et al., "Mouse CD8α+ DCs and human BDCA3+ DCs are major producers of IFN-λ in response to poly IC,"*J. Exp. Med.* 207(12):2703-2717 (2010).
C. Maliszewski, "Dendritic cells in models of tumor immunity. Role of Flt3 ligand," *Pathol. Biol.* 49:481-483 (2001).
T. Miyake et al., "Poly I:C-Induced Activation of NK Cells by CD8α+ Dendritic Cells via the IPS-1 and TRIF-Dependent Pathways,"*J. Immunol.* 183:2522-2528 (2009).
G. Napolitani et al., "Selected Toll-like receptor agonist combinations synergistically trigger a T helper type 1-polarizing program in dendritic cells," *Nature Immunol.* 6(8):769-776 (2005) [published on-line Jul. 3, 2005].
M. O'Keeffe et al., "Effects of administration of progenipoietin 1, Flt-3 ligand, granulocyte colony-stimulating factor, and pegylated granulocyte-macrophage colony-stimulating factor on dendritic cell subsets in mice," *Blood* 99:2122-2130 (2002).
O. Schulz et al., "Toll-like receptor 3 promotes cross-priming to virus-infected cells," *Nature* 433:887-892 (2005).
P. Sheppard et al., "IL-28, IL-29 and their class II cytokine receptor IL-28R," *Nature Immunol.* 4(1):63-68 (2003).

(Continued)

*Primary Examiner* — Robert Landsman
*Assistant Examiner* — Bruce D Hissong

(57) ABSTRACT

In the present invention, CD8+ conventional dendritic cells (CD8+ cDCs) and equivalents thereof (eCD8+ cDCs) in mouse and human have been established as major source of IFN-lambda (IFN-λ) in response to double-stranded (ds) nucleic acids. The invention relates to therapeutic applications of ds nucleic acids or analogs thereof targeting CD8+ and/or eCD8+ cDCs in the prevention and/or treatment of infectious diseases, preferably viral infections, or cancer. Furthermore, the invention relates to an in vitro method for producing IFN-λ and/or generating or obtaining a population of IFN-λ producing CD8+ or eCD8+ cDCs as well as in vitro method for detecting or screening for CD8+ and/or eCD8+ cDCs. In addition, the invention relates to a Flt3-ligand or a M-CSF receptor ligand for use in increasing the level of CD8+ and/or eCD8+ cDCs in a subject suffering from an infectious disease or cancer.

19 Claims, 27 Drawing Sheets

(56) References Cited

OTHER PUBLICATIONS

K. Shortman et al., "Improving vaccines by targeting antigens to dendritic cells," *Exp. Mol. Med.* 41(2):61-68 (2009).

J.R. Smith et al., "Reduced herpes simplex virus type 1 latency in Flt-3 ligand-treated mice is associated with enhanced numbers of natural killer and dendritic cells," *Immunol.* 102:352-358 (2001).

K.S. Stopak et al., "Distinct Patterns of Cytokine Regulation of APOBEC3G Expression and Activity in Primary Lymphocytes, Macrophages, and Dendritic Cells," *J. Biol. Chem.* 282(6):3539-3546 (2007).

S. Vollstedt et al., "Flt3 Ligand-treated Neonatal Mice Have Increased Innate Immunity Against Intracellular pathogens and Efficiently Control Virus Infections," *J. Exp. Med.* 197(5):575-584 (2003).

M.M. Whitmore et al., "Synergistic Activation of Innate Immunity by Double-Stranded RNA and CpG DNA Promotes Enhanced Antitumor Activity," *Cancer Res.* 64:5850-5860 (2004).

R. Zheng et al., "Paired Toll-like Receptor Agonists Enhance Vaccine Therapy through Induction of Interleukin-12," 68(11):4045-4049 (2008).

* cited by examiner

Figure 5
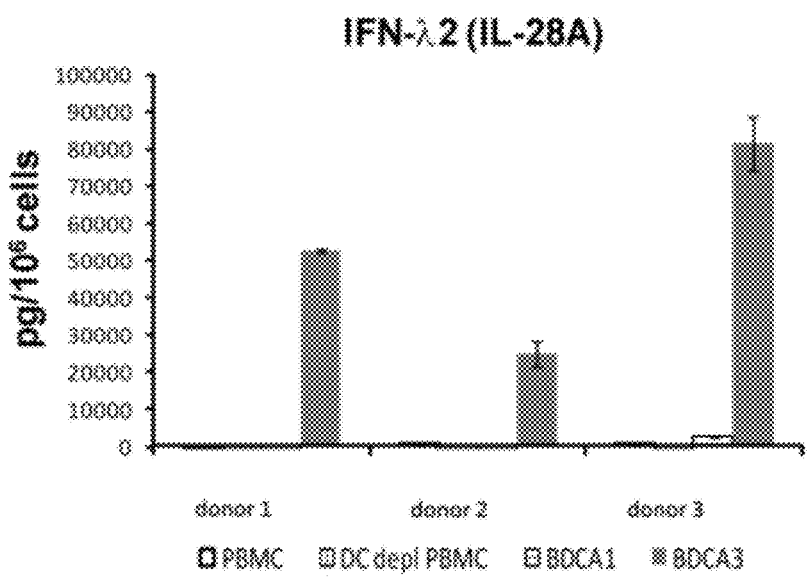
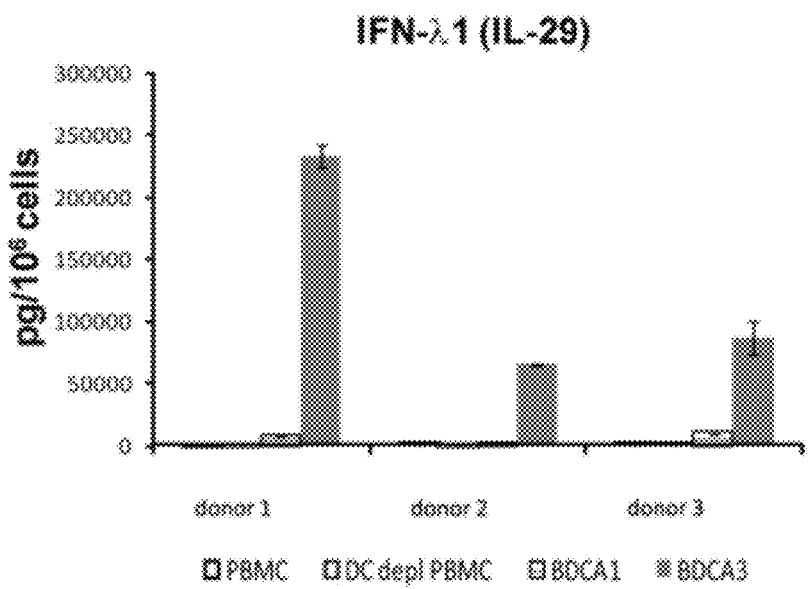

Figure 10 A-B
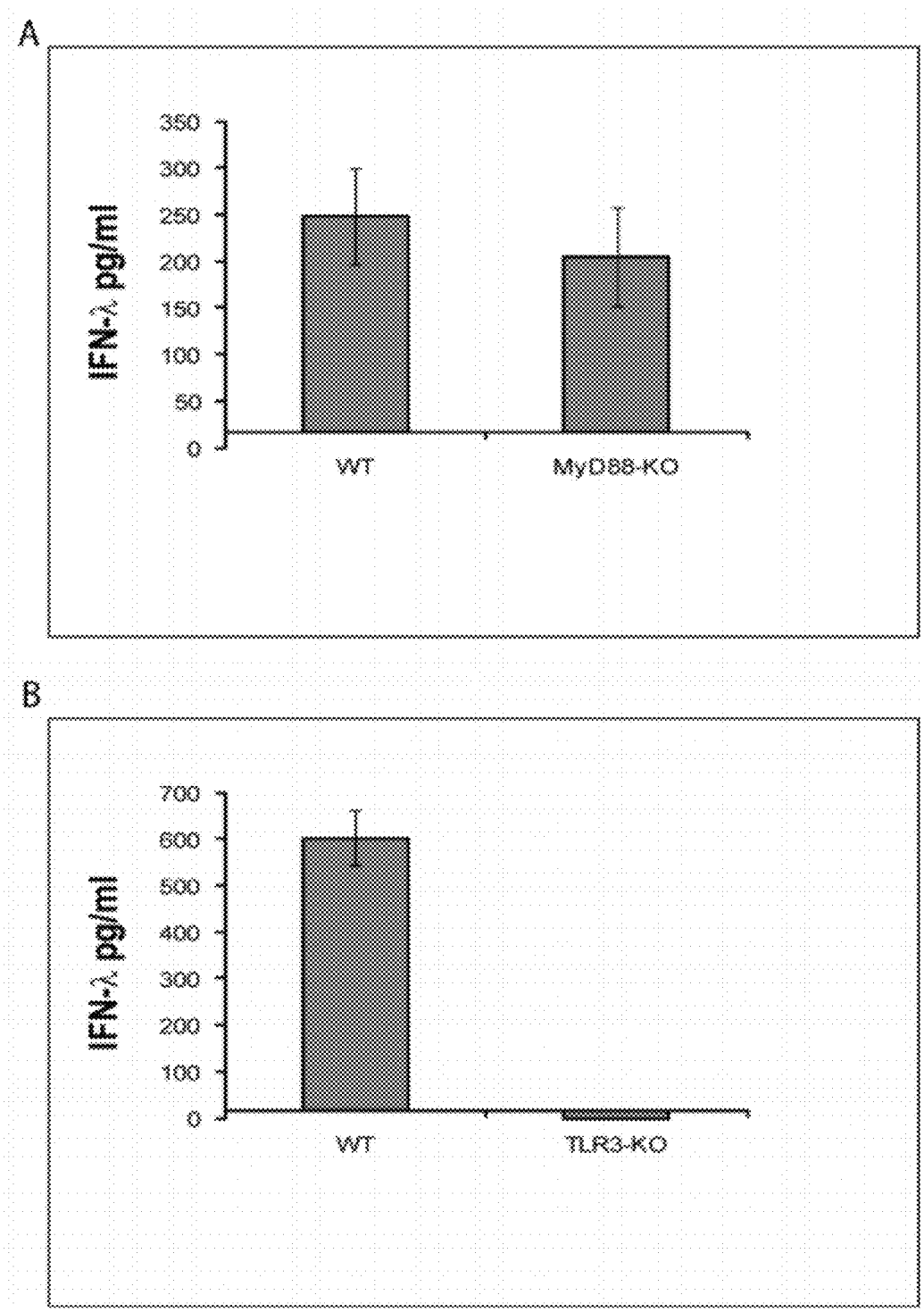

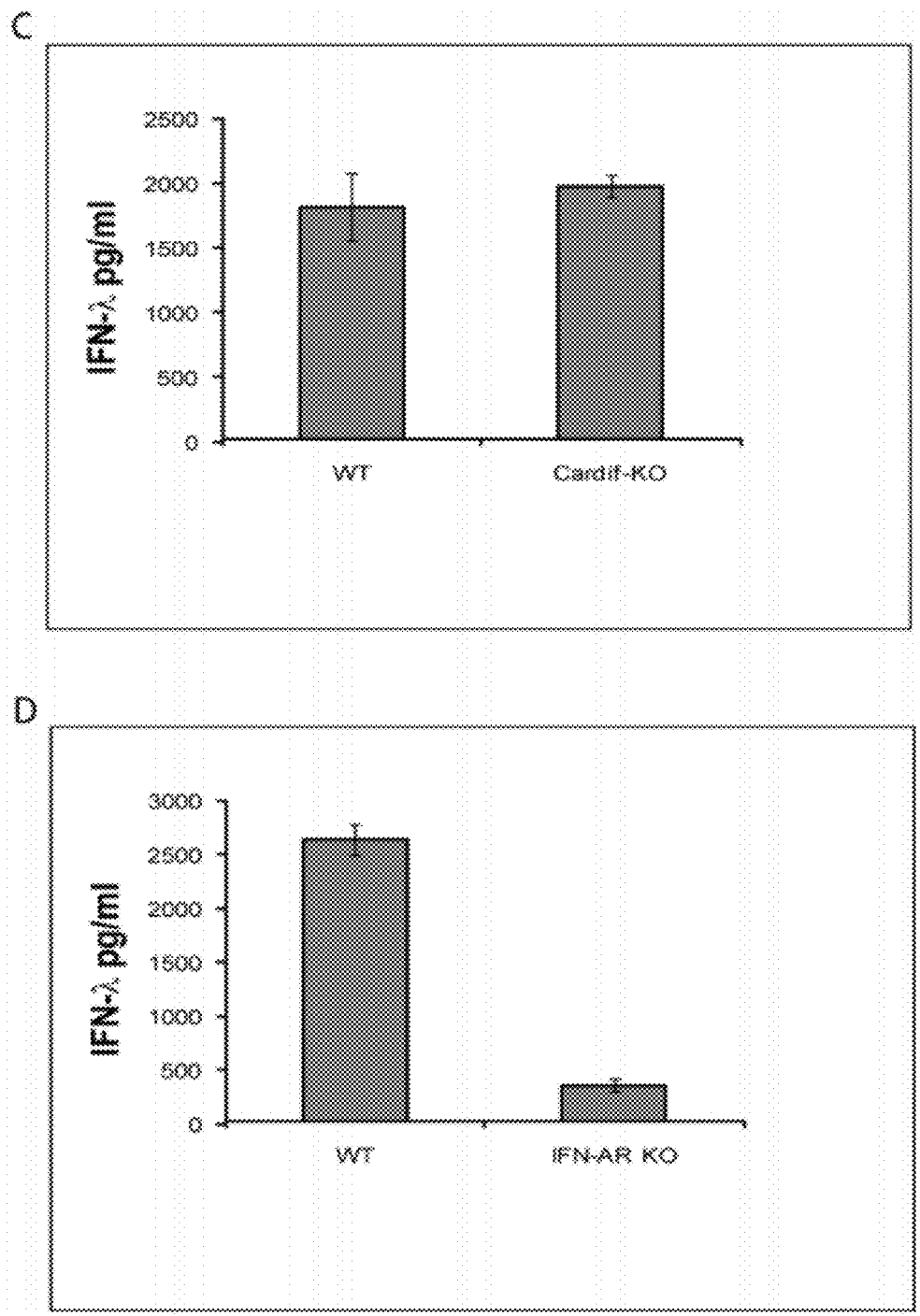
Figure 10 C-D

Figure 14
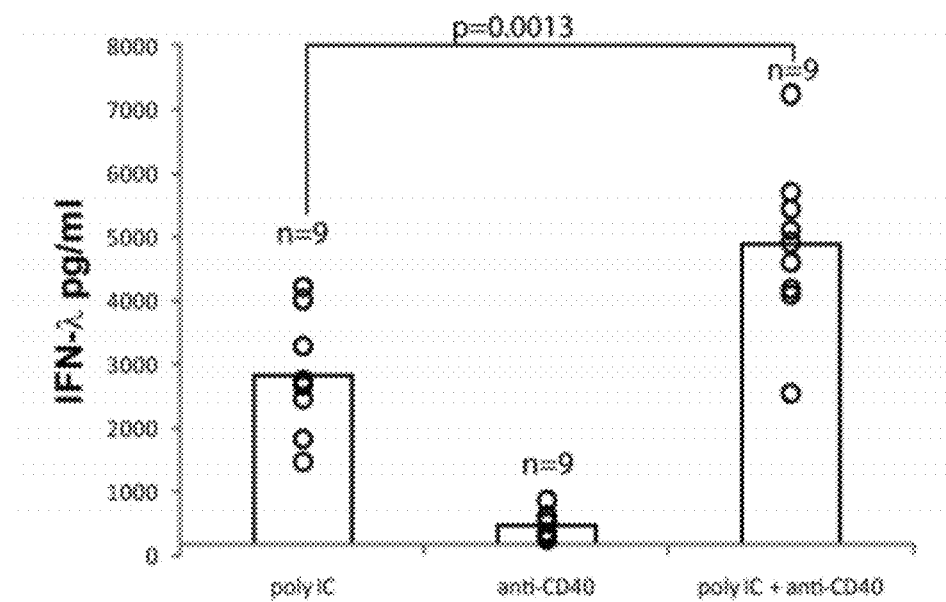
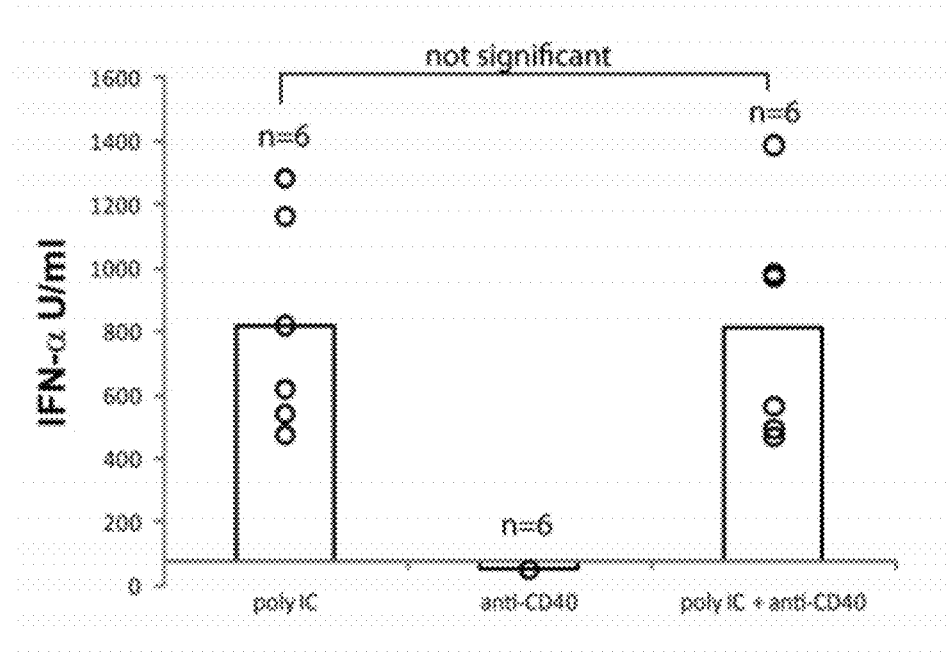

Figure 20
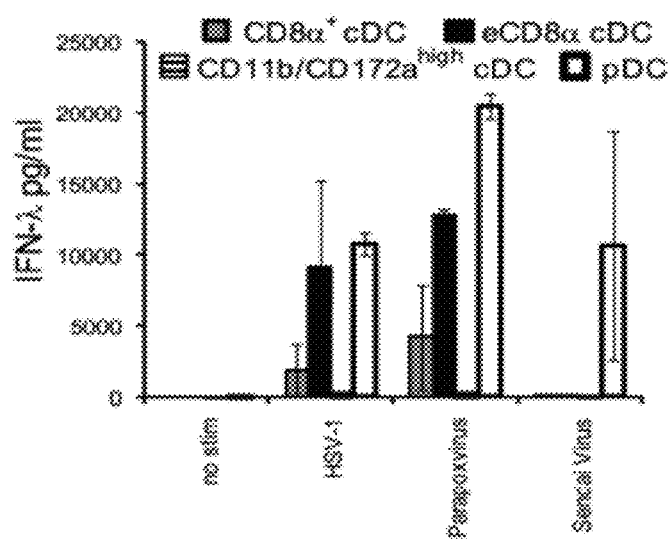
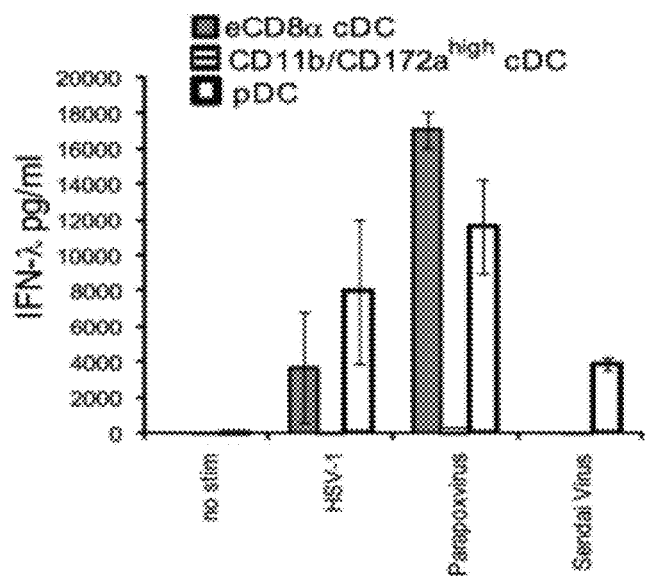

PRODUCTION OF IFN-LAMBDA BY CONVENTIONAL DENDRITIC CELLS

This application is a National Phase application under 35 U.S.C. 5 371 of International Application No. PCT/EP2010/007751, filed Dec. 17, 2010, and claims the benefit under 35 U.S.C. 5 365 of European Application No. 10005348.7, filed May 21, 2010, and the benefit under 35 U.S.C. 5 119(e) of U.S. Provisional Patent Application No. 61/287,777, filed Dec. 18, 2009, the disclosures of which are incorporated herein by reference in their entirety.

FIELD OF THE INVENTION

The present invention relates to the field of immunotherapy, in particular to the field of the production of interferons (IF) by dendritic cells. The invention relates to a specific dendritic cell type responsible for the production of IFN-lambda (IFN-λ) and methods for regulating this production. In particular, the present invention relates to compositions and methods for the production of IFN-λ in vitro and in vivo. The present invention thus relates to therapeutic applications of double stranded (ds) nucleic acids capable of inducing an anti-infectious response, in particular an anti-viral response in a subject by inducing the production of IFN-λ in a specific dendritic cell type. In particular, the present invention relates to ds nucleic acids targeting CD8+ conventional dendritic cells (CD8+ cDCs) and/or equivalents thereof (eCD8+ cDCs) in the prevention and/or treatment of infectious diseases, especially caused by viral infections, or cancer. The invention further relates to methods for producing IFN-λ and/or generating or obtaining IFN-λ producing CD8+ and/or eCD8+ cDCs. The present invention also relates to methods for detecting or screening for CD8+ and/or eCD8+ cDCs. In addition, the invention relates to an ex vivo method for inducing the production of IFN-λ in cDCs.

BACKGROUND OF THE INVENTION

The IFN-lambda (IFN-λ) 1, 2, 3 cytokine family, also called IL-29, IL-28A, and IL-28B, respectively, has recently been identified (Kotenko et al., 2003; Sheppard et al., 2003). IFN-lambdas (IFN-λs) are potent immune-modulatory and anti-viral cytokines, recently implicated in clearance of Hepatitis C virus in humans. IL-28A (also named IFN-λ2), IL-28B (IFN-λ3) and IL-29 (IFN-λ1) are type III interferons that are class II cytokine receptor ligands. IFN-λs are related to type I IFNs (IFN-Is) as well as the IL-10 family of cytokines and signal via a heterodimeric receptor, consisting of one chain unique for IFN-λ (IFN-λ R1 or IL-28Rα) and another chain (IL-10R2), which is shared with IL-10 related cytokines. IFN-λs possess antiviral, antitumor and various immune modulating functions and in many ways resemble the function of IFN-Is (Li et al., 2009). In contrast to the ubiquitous expression of the IFN-I receptor, the expression of the IFN-λ receptor is restricted to limited cell types including epithelial cells and plasmacytoid dendritic cells (pDCs) (Ank et al., 2008; Sommereyns et al., 2008). Exposure to viruses or analogues of nucleic acids such as poly IC or CpG-oligonucleotides (ODN), conditions known to trigger the production of IFN-Is, also induce IFN-λs and largely depend on similar signaling components (Ank et al., 2008; Osterlund et al., 2007; Onoguchi et al., 2007). IFN-λs play a role in toll-like receptor (TLR) induced protection against mucosal viral infections and recent reports link the IL-28B gene with an ability to clear and recover from Hepatitis C infection (Ank et al., 2008; Ge et al., 2009). It is thus of utmost importance to understand the cellular origin of IFN-λs and the regulation of its production.

Several cell types have been described to produce IFN-λ including monocyte derived dendritic cells (DCs) and plasmacytoid dendritic cells (pDCs), but the cellular origin of double-stranded (ds) nucleic acid-induced IFN-λ in vivo is still elusive (Coccia et al., 2004; Ank et al., 2008; Osterlund et al., 2005). Monocyte derived DCs are not CD8+ conventional DCs (CD8+ cDCs) or equivalents of CD8+ cDCs (eCD8+ cDCs) since eCD8+ cDCs involve Fms-related tyrosine kinase 3 ligand (Flt3)-ligand (FL), but not GM-CSF, for development. Monocyte derived DCs fully depend on GM-CSF for development, even though GM-CSF might be combined with other cytokines such as IL-4 or TNF-alpha (TNF-α). GM-CSF dependent DCs are not equivalents of steady state DCs because the lack of GM-CSF or the GM-CSF receptor has no influence on the presence of normal pDC or cDC subsets in lymphoid organs (Naik et al. 2008). If cells are generated in vitro with the combination of GM-CSF and FL, only GM-CSF DC develop, but not pDCs or eCD8+ cDCs (Gilliet et al. 2002).

Polyinosinic:polycytidylic acid (poly IC) is a mimic of viral double stranded (ds) RNA generated during viral infections and it is recognized by TRIF-dependent TLR3 or Cardif (also known as IPS-1, MAVS, VISA)-dependent Rig-like helicases (RLH) in vivo. It is commonly used as an immune stimulant and it is an excellent adjuvant for the induction of Th1 CD4 T cell responses in a DC-targeted vaccine model (Longhi et al., 2009).

Conventional dendritic cells (cDCs) are not only effective antigen presenting cells but are also known as an innate source of cytokines. Among the mouse cDCs, a subset defined by the expression of CD8αα homodimers (CD8+) was identified as the major producers of IL-12p70 in various organs including spleen, lymph nodes, thymus and liver (Reis e Sousa et al., 1997; Hochrein et al., 2001; Pillarisetty et al., 2004). Another functional feature of CD8+ cDCs is their capacity for cross-presentation (Shortman et al., 2009).

The CD8+ cDCs are clearly a functionally distinct DC subset. However, these functional attributes may not always correspond with CD8 expression. Thus, apart from the CD8 molecule, other combinations of surface markers can be used to identify CD8+ cDC or their functional equivalents that may lack CD8 expression (eCD8+). Among CD11c$^+$ MHC Class II high cells, various combinations of high expression of CD205, CD103, Necl2, Clec9a, CD24 accompanied with negative or low expression of CD11b and CD172a can be used (Hochrein and O'Keeffe, 2008; Shortman et al., 2009).

DC subsets can be generated in vitro from bone marrow precursor cells in the presence of Flt3-ligand (FL), FLDC (Brasel et al., 2000). The FLDC cDCs lack expression of CD8 and CD4, but using markers described above, they can be divided into functionally distinct subsets that resemble the spleen cDCs. One FLDC subset has been identified as the eCD8+ since it depends on the same transcription factors for development as CD8+ cDC, expresses several characteristic surface markers, such as high expression of Clec9a, but low expression of CD11b and CD172a and shows a similar expression profile of TLRs. Functionally, the eCD8+ DCs demonstrate a similar TLR-ligand responsiveness, as well as high IL-12p70 production and efficient cross-presentation. Upon in vivo transfer and recovery in the spleen, eCD8+ DCs express CD8 on their surface (Naik et al., 2005).

Expression of the different nucleic acid sensing systems TLR3, TLR7, or TLR9 and the RLHs varies among DC subsets (Hochrein and O'Keeffe, 2008). The downstream functions after engagement of these receptors also differ among the different DCs. pDCs predominantly use TLR7 and TLR9 for nucleic acid sensing, resulting in the high production of IFN-I and IFN-λs. Among cDCs, CD8+ cDCs highly express TLR3 but lack expression of TLR7 (Edwards et al., 2003). Furthermore, it has been found by proteomics that CD8+ cDCs, in contrast to CD8-cDCs, hardly express the RLHs and as a consequence are unable to detect the single stranded (ss) RNA viruses Sendai or Influenza virus (Luber et al., 2010).

CD8 is not expressed on human DC, whereas CD4 is expressed by all DC subsets, and thus other markers have to be employed to define human DC subsets and to possibly align the mouse and human counterparts. A set of antibodies designated BDCA1-4 has been established and is used to differentiate between pDCs and subsets of cDCs (Dzionek et al., 2000). Human BDCA3 positive DCs have been proposed as the human eCD8+ DC since they, as the mouse eCD8+ DC, selectively express high levels of Clec9a and Necl2, but only low amounts of CD11b (Shortman et al., 2009). Genome wide transcriptional analysis substantiated a close relationship of murine CD8+ cDC with human BDCA3+ cDCs (Robbins et al., 2008). As with the mouse eCD8+ cDCs, the human BDCA3+ cDCs have been found in various organs including blood, spleen, lung, tonsils, lymph nodes, colon and liver. Functional correlation between these human and mouse DC subsets are scarce although the $CD11b^{low}$ cDC of human thymus correlated with the mouse thymic $CD11b^{low}$ DC with high IL-12p70 production (Vandenabeele et al., 2001; Hochrein et al., 2001).

Miyake at al., 2009, describes that poly IC activates NK cells via IPS-1 and TRIF dependent ways. Both pathways were involved in B16 tumor suppression via NK cells. CD8a+ cDCs were identified as source of type I IFN (IFN-alpha/beta), IL-6 and IL-12p40 and responsible for the NK cell activation as measured by IFN-gamma production by NK cells.

Schulz et al., 2005, describes that, dsRNA present in virally infected cells is recognized by dendritic cells via TLR3. That, poly IC activates CD8a+ cDCs (increase of surface markers such as CD40, CD86, CD80 and gene activation of TNF-alpha, IL-6 and IFN-alpha/beta but only IL-6 protein could be detected). It was shown that TLR3 was necessary for this activation and that activated CD8a+ cDCs induced stronger CTL induction via cross-presentation.

Diebold et al., 2009, describes that replicon plasmid induce dsRNA intermediates which are detected by CD8a+ cDCs in a TLR3 dependent way. In contrast the activation of CTL was independent of TLR3.

WO 2006/054177 describes that certain tumors express TLR3 and that these tumors might be treated with TLR3-agonists such as poly AU.

WO 2009/088401 describes that combinations of TLR ligands with one of them being a TLR3 agonist would induce increased (adaptive) immune responses especially antigen specific CD8 T-cell responses. The claims also include activation of dendritic cells with combinations of TLR3 agonists and other TLR agonists and claim enhanced CD8 T-cell responses including enhanced cytokines produced by the T-cells.

WO 2004/060319 describes that combinations of TLR agonists and TNF/R agonist increase the amount of an antigen specific immune response. These antigen specific responses were either from T-helper cells (CD4 T cells) or Killer T cells (CD8 T cells).

WO 94/28391 describes that ligands for FLT3 can be used for hematopoietic stem cell or other immune cell expansion. Different forms of Flt3-ligands are described.

WO 2008/131926 describes that M-CSF can be used independent of Flt3-ligands or GM-CSF to induce the generation of dendritic cells. In particular the production of pDCs was independent of FL and of cDCs independent of GM-CSF.

Ank et al., 2008, describes that many different cell types produce IFN-lambda to TLR ligands or viruses. It also analyses the IFN-lambda receptor expression and uses in vivo virus infection models. Local application (intra vaginal) of poly IC or CpG-ODN protected mice from lethal intra vaginal HSV-2 challenge. It describes also that cDCs, pDC, B-cells T-cells and macrophages from the spleen produced IFN-lambda mRNA in response to HSV-2.

Sheppard et al., 2003, describes the existence of the IFN-lambdas and that they are related to IFN-I and IL-10 family of cytokines. It shows mRNAs for IFN-lambdas (IL-28A, IL-28B, IL-29), IFN-alpha and IFN-beta of human PBMCs after poly IC treatment or EMCV infection. The mRNA of the 3 IFN-lambdas and IFN-alpha and IFN-beta were upregulated upon exposure to either poly IC or virus.

O'Keeffe et al., 2002, describes the increase of DC subsets in response to various growth factors including showing the increase of CD8a cDCs in response to flt3-ligand. IL-12p40 and IL-12p70 production in response to CpG was analyzed and CD8a+ cDCs and after FL to ProGP (fusion protein of FL and G-CSF) $CD8a^{int}$ cDCs were the major producers of IL-12p70.

However, none of the above cited documents and patent applications provides a clue about cells which are the source of IFN-lambda.

It is therefore an object of the present invention to provide the specific type of cDC, which is the major producer of ds nucleic acid-induced IFN-λ.

SUMMARY OF THE INVENTION

The present invention provides the following items:

[1] A composition comprising a double-stranded (ds) nucleic acid or analog thereof for use in the induction of IFN-λ production in CD8+ and/or eCD8+ conventional dendritic cells (cDCs), wherein said eCD8+ cDCs express Clec9a and/or Necl2. Preferably, said conventional cDCs are human cDCs.

[2] Use of a double-stranded (ds) nucleic acid or analog thereof for the preparation of a pharmaceutical composition for the induction of IFN-λ production in CD8+ and/or eCD8+ conventional dendritic cells, wherein said eCD8+ cDCs express Clec9a and/or Necl2. Preferably, said conventional cDCs are human cDCs.

[3] A method for inducing IFN-λ production in CD8+ and/or eCD8+ conventional dendritic cells, wherein said eCD8+ cDCs express Clec9a and/or Necl2, in a subject in need thereof, comprising the step of administering to said subject a composition comprising a double-stranded (ds) nucleic acid or analog thereof. Preferably, said conventional cDCs are human cDCs.

[4] The composition of item [1], the use of item [2] or the method of item [3] for use in a method of prevention and/or treatment of an IFN-λ dependent disease.

[5] The composition of item [1] or [4], the use of item [2] or [4] or the method of item [3] or [4], wherein said double-stranded (ds) nucleic acid or analog thereof is administered to CD8+ and/or eCD8+ conventional dendritic cells (cDCs) from a subject ex vivo, said cDCs are preferably isolated from said subject.

[6] The composition, use or the method of item [5], wherein an agent which increases the level of CD8+ and/or eCD8+ conventional dendritic cells (cDCs) is administered to said isolated cDCs ex vivo prior to the administration of said double-stranded (ds) nucleic acid or analog thereof.

[7] The composition, use or method of any one of items 1 to 6, wherein said ds nucleic acid is dsRNA or dsDNA.

[8] The composition, use or method of any one of any one of items [1] to [7], wherein said induction is independent of MyD88-dependent TLRs.

[9] The composition, use or method of any one of any one of items [1] to [8], wherein said induction is independent of (the adaptor molecule) MyD88.

[10] The composition, use or method of any one of any one of items [1] to [9], wherein said induction is independent of (the adaptor molecule for Rig-like helicases) Cardif.

[11] The composition, use or method of any one of any one of items [1] to [10], wherein said induction is independent of TRIF.

[12] The composition, use or method of any one of any one of items [1] to [11], wherein said induction is independent of TLR-7 and/or TLR-9.

[13] The composition, use or method of any one of any one of items [1] to [12], wherein said induction is mediated by TLR-3.

[14] The composition, use or method of any one of any one of items [1] to [13], wherein said induction is mediated by IRF3 and/or IRF7.

[15] The composition, use or method of any one of any one of items [1] to [14], wherein said induction is mediated by IRF8.

[16] The composition, use or method of any one of any one of items [1] to [15], wherein said induction is mediated by IFN-IR.

[17] The composition, use or method of any one of any one of items [1] to [16], wherein said composition further comprises an agent which increases the level of CD8+ and/or eCD8+ conventional dendritic cells (cDCs).

[18] The composition, use or method of item [17], wherein said agent which increases the level of CD8+ and/or eCD8+ conventional dendritic cells is a Flt3-ligand or a M-CSF receptor ligand.

[19] The composition, use or method of any one of items [1] to [18], wherein said composition further comprises an agent enhancing ds nucleic acid-based IFN-λ production.

[20] The composition, use or method of item [19], wherein the agent enhancing ds nucleic acid-based IFN-λ production is a agent which is a TLR-ligand, wherein the TLR-ligand is preferably a TLR2 ligand, a TLR4 ligand, a TLR9 ligand, a TLR10 ligand or a TLR11 ligand; or a TNF-family member, wherein the TNF-family member preferably is a CD40-ligand or a cytokine, wherein the cytokine preferably is a Flt3-ligand, a M-CSF receptor ligand, IL-3, GM-CSF, IL-4, or IFN-γ.

[21] A composition comprising an agent which increases the level of CD8+ and/or eCD8+ conventional dendritic cells (cDCs), wherein said eCD8+ cDCs express Clec9a and/or Necl2, in combination with a double-stranded (ds) nucleic acid or analog thereof for use in a method of prevention and/or treatment of an IFN-λ dependent disease, comprising
(a) administering to a subject said agent which increases the level of CD8+ and/or eCD8+ conventional dendritic cells (cDCs); and
(b) administering to a subject a double-stranded (ds) nucleic acid or analog thereof to induce production of IFN-λ in CD8+ and/or eCD8+ conventional dendritic cells.

[22] A method for the prevention and/or treatment of an IFN-λ dependent disease in a subject in need thereof, comprising the steps
(a) administering to a subject said agent which increases the level of CD8+ and/or eCD8+ conventional dendritic cells (cDCs); and
(b) administering to a subject a double-stranded (ds) nucleic acid or analog thereof to induce production of IFN-λ in CD8+ and/or eCD8+ conventional dendritic cells.

[23] The composition of item [21] or the method of item [22], wherein said agent which increases the level of CD8+ and/or eCD8+ conventional dendritic cells is a Flt3-ligand or a M-CSF receptor ligand.

[24] The composition, use or method of any one of items [1] to [23], wherein said IFN-λ dependent disease is an infectious disease or cancer.

[25] The composition, use or method of item [24], wherein said IFN-λ dependent disease is a disease of blood, spleen, lung, tonsils, lymph nodes, colon or liver.

[26] The composition, use or method of item [24] or [25], wherein said infectious disease is a viral infection.

[27] The composition, use or method of item [26], wherein said viral infection is an infection by a virus that comprises dsRNA or dsDNA.

[28] The composition, use or method of item [26] or [27], wherein said viral infection is a persistent viral infection, preferably a viral infection of the liver or a Herpes virus infection, more preferably a Hepatitis virus infection.

[29] An in vitro method for producing IFN-λ and/or generating or obtaining a population of IFN-λ producing CD8+ or eCD8+ conventional dendritic cells, wherein said eCD8+ cDCs express Clec9a and/or Necl2, comprising the steps of:
(a) providing a population of cells comprising CD8+ and/or eCD8+ conventional dendritic cells;
(b) contacting said conventional dendritic cells with an agent that increases the level of said conventional dendritic cells, said agent is preferably a Flt3-ligand or an M-CSF receptor ligand; and
(c) contacting said conventional dendritic cells with a double-stranded (ds) nucleic acid or analog thereof.

[30] The method of item [29], wherein the population of cells is further incubated with an enhancer of IFN-λ production.

[31] The method of item [30], wherein the enhancer is a TLR-ligand, wherein the TLR-ligand is preferably a TLR2 ligand, a TLR4 ligand, a TLR9 ligand, a TLR10 ligand or a TLR11 ligand; or a TNF-family member, wherein the TNF-family member preferably is a CD40-ligand or a cytokine, wherein the cytokine preferably is IL-3, GM-CSF, IL-4, or IFN-γ.

[32] A pharmaceutical composition comprising a population of IFN-λ producing human CD8+ and/or eCD8+ conventional dendritic cells obtainable by the method of any one of items 29 to 31 and, optionally, a pharmaceutically acceptable carrier or diluent.

[33] An in vitro method for detecting or screening for human CD8+ and/or eCD8+ conventional dendritic cells, comprising the steps of:
(a) providing a population of cells comprising dendritic cells;
(b) selecting BDCA3+ dendritic cells;
(c) contacting said BDCA3+ cells with a double-stranded (ds) nucleic acid or analog thereof;
(d) detecting the production of IFN-λ; and
(e) correlating the production of IFN-λ with the presence of CD8+ and/or eCD8+ conventional dendritic cells.

[34] The method of item [33] for screening or detecting the presence of CD8+ and/or eCD8+ conventional dendritic cells in a biopsy, preferably a biopsy of an organ or blood.

[35] A method for inducing the production of IFN-λ in a population of (human) conventional dendritic cells (cDCs) comprising contacting ex vivo cDCs with a double-stranded (ds) nucleic acid or analog thereof.

[36] The method of item [35], wherein Flt3-ligand- and/or M-CSF receptor ligand-pretreated cDCs are contacted ex vivo with said ds nucleic acid.

[37] The composition, use or method of any one of the preceding items, wherein said analog of a ds nucleic acid is poly IC, poly AU, poly ICLC, poly dAaT

[38] A composition comprising a double-stranded (ds) nucleic acid or analog thereof targeting CD8+ and/or eCD8+ cDCs for use in the prevention and/or treatment of an infectious disease or cancer, preferably a viral infection.

[39] A combined preparation comprising a ds nucleic acid or analog thereof targeting CD8+ and/or eCD8+ cDCs and an agent enhancing ds nucleic acid-based IFN-λ production.

[40] The combined preparation according to item [39], wherein the agent enhancing ds nucleic acid-based IFN-λ production is a TLR-ligand, wherein the TLR-Ligand is preferably a TLR2 ligand, a TLR4 ligand, a TLR9 ligand, a TLR10 ligand or a TLR11 ligand; or a TNF-family member, wherein the TNF-family member preferably is a CD40-ligand or a cytokine, wherein the cytokine preferably is a Flt3-ligand, a M-CSF receptor ligand, IL-3, GM-CSF, IL-4, or IFN-γ.

[41] A Flt3-ligand or an M-CSF receptor ligand for use in increasing the level of CD8+ and/or eCD8+ cDCs in a subject suffering from an infectious disease or cancer, preferably a viral infection.

[42] The composition according to item [38], or the Flt3-ligand or M-CSF receptor ligand according to item [41], wherein the viral infection is a persistent viral infection, preferably a viral infection of the liver or a Herpes virus infection, more preferably a Hepatitis virus infection.

[43] An in vitro method for producing IFN-λ and/or generating or obtaining a population of IFN-λ producing CD8+ or eCD8+ cDCs, comprising the steps of: (a) providing a population of cells comprising CD8+ and/or eCD8+ cDCs; and (b) contacting the cDCs with a ds nucleic acid or analog thereof.

[44] The method according to item [43], wherein the population of cells is incubated with an enhancer of IFN-λ production.

[45] The method according to item [44], wherein the enhancer is a TLR-ligand, wherein the TLR-ligand is preferably a TLR2 ligand, a TLR4 ligand, a TLR9 ligand, a TLR10 ligand or a TLR11 ligand; or a TNF-family member, wherein the TNF-family member preferably is a CD40-ligand or a cytokine, wherein the cytokine preferably is IL-3, GM-CSF, IL-4, or IFN-γ.

[46] A pharmaceutical composition comprising a population of IFN-λ producing CD8+ and/or eCD8+ cDCs obtainable by the method according to any one of items [43] to [45] and, optionally, a pharmaceutically acceptable carrier or diluent.

[47] An in vitro method for detecting or screening for CD8+ and/or eCD8+ cDCs, comprising the steps of: (a) providing a population of cells; (b) contacting the cells with a ds nucleic acid or analog thereof capable of stimulating or inducing the production of IFN-λ in CD8+ and/or eCD8+ cDCs; (c) detecting the production of IFN-λ; and (d) correlating the production of IFN-λ with the presence of CD8+ and/or eCD8+ cDCs.

[48] The method according to item [47] for screening or detecting the presence of CD8+ and/or eCD8+ cDCs in a biopsy, preferably a biopsy of an organ or blood.

[49] A method for inducing the production of IFN-λ in a population of cDCs comprising contacting ex vivo a cDC with a ds nucleic acid or analog thereof.

[50] The method according to item [49], wherein Flt3-ligand- and/or M-CSF receptor ligand-pretreated cDCs are contacted ex vivo with said ds nucleic acid.

It must be noted that as used herein, the singular forms "a", "an", and "the", include plural references unless the context clearly indicates otherwise. Thus, for example, reference to "an agent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

As described herein, "preferred embodiment" means "preferred embodiment of the present invention". Likewise, as described herein, "various embodiments" and "another embodiment" means "various embodiments of the present invention" and "another embodiment of the present invention", respectively.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

DETAILED DESCRIPTION OF THE INVENTION

The invention is based on the finding that ds RNA induces IFN-λ production in CD8+ conventional DCs (CD8+ cDCs) and equivalents of CD8+ cDCs (eCD8+ cDCs), whereas it is known in the prior art that plasmacytoid DCs (pDCs) are responsible for IFN-λ production by a different mechanism.

The inventors of the present application surprisingly found that ds nucleic acids, as dsRNA or dsDNA, as well as synthetic ds nucleic acid analogs, such as poly IC, induce large amounts of IFN-λ in CD8+ conventional DCs (CD8+ cDCs) and equivalents of CD8+ cDCs (eCD8+ cDCs) but not in pDCs or in other cDC subsets. Contacting CD8+ or eCD8+ cDCs with ds nucleic acid or an analog thereof stimulates the production of IFN-λ.

Plasmacytoid DCs (pDCs) produce large amounts of IFN-λ under conditions that also induce large amounts of IFN-alpha (IFN-α). This production via pDCs is completely dependent on the presence of the Toll-like receptor (TLR) adaptor molecule MyD88. Using several knock-out mice, the present inventors were able to demonstrate that the IFN-λ production of CD8+ cDCs in response to a synthetic ds nucleic acid analog is independent of MyD88-dependent TLRs, independent of the adaptor molecule for TLRs, MyD88, independent of the adaptor molecule for Rig-like helicases, Cardif, independent of TRIF which is a TIR-domain-containing adapter-inducing interferon-β (TRIF) that responds to activation of toll-like receptors (TLRs), independent of TLR-7 and/or independent of TLR-9.

TLR-7 recognizes ssRNA, TLR-9 recognizes dsDNA, while TLR-3 recognizes dsRNA. Interestingly, human conventional dendritic cells (i.e., BDCA3+ cells) do not express TLR-9, while human plasmacytoid dendritic cells express TLR-9. However, nevertheless human conventional dendritic cells can recognize dsDNA and are thus induced to produce IFN-λ as shown in the appended Examples (see Example 11).

In addition, by the use of further knock-out mice, the present inventors found that IFN-λ production is mediated by TLR-3 (i.e., the receptor that recognizes dsRNA). Furthermore, the present inventors found that IFN-λ production is mediated by IRF3 and/or IRF7, IRF8 and/or IFN-RI.

IRF3, IRF7 and IRF8 are members of the interferon regulatory transcription factor (IRF) family, while IFN-RI is the IFN receptor type I.

Specifically, in the present invention mouse CD8+ and eCD8+ cDCs were identified as major producers of IFN-λ in response to ds nucleic acids (dsRNA or dsDNA) as well as synthetic ds nucleic acid analogs, such as poly IC, in vitro and in vivo. The nature of the stimulus and the cytokine milieu determined if CD8+ cDCs produced IFN-λ or IL-12p70. IFN-λ, but not IFN-α, production to poly IC in vivo was abrogated in mice that lacked most DC due to a lack of Fms-related tyrosine kinase 3 ligand. TLR3, but not RLHs, was shown to be involved in in vivo poly IC-induced IFN-λ production. IRF7, which is required for MyD88-dependent type I IFN production, was also shown to be involved in this IFN-λ production. The BDCA3+ human DC, proposed to be the equivalents of mouse CD8+ DCs, displayed the highest IFN-λ1 and IFN-λ2 production upon poly IC stimulation. CD8+ cDC equivalents in mouse and human have been identified as the major source of IFN-λs in response to ds nucleic acids (dsRNA or dsDNA) as well as synthetic ds nucleic acid analogs, such as poly IC.

Within all species studied, dendritic cells are rare cells present in blood, skin, and all lymphoid organs. In the spleen, for example, they account for only about 1% of total splenocytes. Yet, it is clear that these rare cells are crucial for normal immune responses. Mice depleted of DCs display defective immune responses to viral (Ciavarra et al., 2006), parasitic (Jung et al., 2002; Liu et al., 2006a), and bacterial infections (Jung et al., 2002).

The most extensive studies of DC subtypes have been carried out in the mouse system. It is clear that within every mouse lymphoid organ and blood there are two distinct categories of DCs: conventional DCs (cDCs) and plasmacytoid DCs (pDCs). The same scenario exists in other mammalian species, including humans. Accordingly, the CD8+ and eCD8+ cDCs of the present invention can be further separated by phenotype, function and origin. Within the murine spleen three major cDC subsets have been defined (see Table 1). Based on their selective expression of the molecules CD8-alpha (CD8α) and CD4 they are named CD8+ DC (CD8$^{pos}$, CD4$^{neg}$), CD4+ DC (CD8$^{neg}$, CD4$^{pos}$) and double negative DN-DC (CD8$^{neg}$, CD4$^{neg}$).

TABLE 1

Differential expression of selected molecules on the cell surface of spleen cDC subsets.

|  | CD4(−) CD8(−) | CD4(+) CD8(−) | CD4(−) CD8(+) |
| --- | --- | --- | --- |
| CD1d | +/− | +/− | ++ |
| CD5 | + | ++ | +/− |
| CD11b | ++ | ++ | +/− |
| CD22 | + | ++ | +/− |
| CD24 | + | + | +++ |
| CD36 | +/− | +/− | ++ |
| CD49f | + | + | +++ |
| CD72 | + | + | − |
| CD81 | + | +/− | ++ |
| CD103 | − | − | ++ |
| CD205 | + | + | +++ |
| CD207 | − | − | + |
| F4/80 | ++ | ++ | +/− |
| Clec9a | − | − | + |
| Necl2 | − | − | ++ |
| XCR1 | − | − | ++ |
| Sirp-α | ++ | ++ | +/− |

The CD8+ and eCD8+ cDCs of the present invention can be further characterized by the differential expression of selected molecules according to the above Table 1. Notably, the skilled person, if necessary, will be readily in a position to find the human counterpart molecules on the cell surface of spleen cDC subsets in case Table 1 only provides the mouse molecule and vice versa.

Beside the phenotypic differentiation several functional differences have been identified, e.g. the CD8+ DCs are the major cross-presenters, the major IL-12p70 producers and are able to respond to dsRNA via TLR3. In contrast they cannot respond to ssRNA due to the lack of the ssRNA receptors TLR7 and RIG-I.

Whereas pDC are known to produce IFN-λ in response to CpG-DNA or to Sendai Virus (SeV), the inventors of the present application have surprisingly found that CD8+ cDCs are the sole producers of IFN-λ in response to dsRNA.

Besides the isolation of DC subsets from the animal, DC subsets can be generated utilizing Flt3-ligand (or M-CSF receptor ligand) to drive mouse bone marrow precursors into cDC and pDC (Brasel et al., 2000; Brawand et al., 2002; Gilliet et al., 2002; Hochrein et al., 2002; Fancke et al., 2008). These systems generate high numbers of immature cDC and pDC and has been instrumental in defining the mouse pDC in particular.

Subsets of DCs in Flt3-ligand cultures: pDC and cDC subsets are defined with the help of surface markers as follows:
pDC: CD11C$^{pos}$, CD11b$^{low}$, B220$^{high}$, CD45RA$^{hi}$, CD24$^{low}$, Sirp-α$^{pos}$
cDC equivalents of CD8$^{neg}$ DC (eCD8$^{neg}$ DC): CD11C$^{pos}$, CD11b$^{high}$, B220$^{neg}$, CD45RA$^{neg}$, CD24$^{low}$, Sirp-α$^{pos}$
cDC equivalents of CD8+ DC (eCD8+ DC): CD11c$^{pos}$, CD11b$^{low}$, B220$^{neg}$, CD45RA$^{neg}$, CD24$^{high}$, Sirp-α$^{neg}$ The finding that CD8+ and eCD8+ cDCs are major producers of IFN-λ enables one to use this feature to identify CD8+ and/or eCD8+ cDCs in different mixed cell populations of different organs. In those mixed populations the IFN-λ production corresponds with the presence of CD8+ and/or eCD8+ cDCs and thus allows detecting the presence of eCD8+ cDCs via their specific cytokine they produce.

DEFINITIONS

In the present invention, the IFN-λ can be IFN-λ1, IFN-λ2, or IFN-λ-3, which are also referred to as IL-29, IL-28A and IL-28B, respectively.

In the present invention, the term "ds" is equally used for the terms "double-strand" and "double-stranded", respectively. Likewise, the term "ss" is equally used for the terms "single-strand" and "single-stranded". ds nucleic acid includes both dsRNA and dsDNA.

Poly IC is a mismatched ds RNA with one strand being a polymer of inosinic acid, the other a polymer of cytidylic acid. Poly IC is a synthetic double-strand RNA and, thus, can be considered as a synthetic analog of ds RNA. Poly IC is a common tool for scientific research on the immune system. In a preferred embodiment, the ds nucleic acid or analog thereof according to the present invention is poly IC. However, further synthetic analogs of ds nucleic acids are equally suitable according to the present invention as, for example, polyadenylic-polyuridylic acid (Poly AU), which is a synthetic ds RNA, signalling exclusively via TLR3 (Wang et al. 2002). Likewise, equally suitable is poly (ICLC), which is a poly IC complexed with carboxymethylcellulose and poly L-lysine (Longhi et al., 2009), or poly (dA:dT), which is a synthetic ds DNA of poly (dA-dT)*poly (dA:dT) complexed with liposomes (Ishii et al., 2006). The further synthetic analogs of ds nucleic acids described in Wang et al. 2002, Longhi et al., 2009 and Ishii et al., 2006 are incorporated herein by reference as synthetic analogs of ds nucleic acids, which are equally suitable in the present invention. Also suitable are artificial ds oligonucleotides (sense and antisense), which may be provided in combination with transfecting reagents.

As used herein, the phrase "pharmaceutically acceptable diluent or carrier" is intended to include substances that can be co-administered with the active compound of the medicament and allows the active compound to perform its indicated function. Examples of such carriers include solutions, solvents, dispersion media, delay agents, emulsions and the like. The uses of such media for pharmaceutically active substances are well known in the art. Any other conventional carrier suitable for use in the present invention falls within the scope of the instant invention.

The term "effective amount" in accordance with the present invention refers to the amount necessary or sufficient to realize a desired effect, in particular a medical and/or biological one.

In the present invention, the ds nucleic acid or analog thereof that is stimulating or inducing the production of IFN-λ in CD8+ and/or eCD8+ cDCs is preferably ds DNA or ds RNA, including analogs thereof. Suitable dsDNA may comprise natural dsDNA such as genomic DNA which might be of prokaryotic or eukaryotic or viral origin, e.g. mitochondrial DNA, plasmid DNA, viral DNA or thymic DNA. To facilitate the uptake of the DNA, methods for enhanced uptake such as liposomes, electroporation, or nanoparticles may be employed.

In one embodiment, the ds nucleic acid or analog thereof according to the present invention is provided by a dsDNA virus, a dsRNA virus or an ssRNA virus. The dsRNA or dsDNA according to the present invention, including analogs thereof, can be provided by a dsDNA virus, a dsRNA virus, an ssDNA virus, or a positive ssRNA virus. Thus, in one embodiment, the analog of a ds nucleic acid according to the present invention is an ss nucleic acid, which is processed or can be processed to a ds nucleic acid. Further analogs of a ds nucleic acid are poly IC, poly AU, poly ICLC, poly dAdT. These analogs are envisaged to be applied in the compositions, uses and methods of the present invention.

In various embodiments, the virus is a positive ssRNA virus, such as a Togavirus, a Flavivirus, an Astrovirus, a Picornavirus, a Calicivirus, a Hepevirus, a Nodavirus, an Arterivirus, or a Coronavirus. In various embodiments, the virus is a dsRNA virus, such as Reovirus or a Birnavirus. In various embodiments, the virus is a retrovirus, such as an HIV-1, HIV-2, or SIV. In various embodiments, the virus is a ds DNA virus, such an Asfarvirus, an Iridovirus, a Polyomavirus, a Papillomavirus, a Papovavirus, an Adenovirus, a Herpesvirus, a Poxvirus, or a Hepadnavirus. In a preferred embodiment, the virus is a poxvirus, such as an Orthopoxvirus or a Parapoxvirus. Preferably, the poxvirus is a variola virus, a cowpoxvirus, a camelpoxvirus, or a vaccinia virus. Particularly preferred is a MVA virus. In various embodiments, the virus is a Herpesvirus, such as a Herpes simplex virus (HSV 1 or HSV 2), Varicella Zoster virus, human cytomegalovirus, Epstein-Barr virus, and Kaposi sarcoma-associated herpesvirus.

In various embodiments, the ds nucleic acid or analog thereof that stimulates the production of IFN-λ in CD8+ and/or eCD8+ cDCs is produced by a dsDNA virus or an ssRNA virus. In preferred embodiments, the virus is a Poxvirus, Herpesvirus, Togavirus, or a Coronavirus.

In various embodiments, the ds nucleic acid or analog thereof according to the present invention is recognized via toll-like receptor (TLR) 3 on cDCs.

Isolation and Characterization of DCs According to the Invention

When used herein the term "conventional dendritic cells" or "CD8+ conventional dendritic cells", sometimes also abbreviated as "cDC(s)" encompasses mouse CD8+ conventional dendritic cells which are characterized by the features described herein such as expression of the surface markers (molecules) (see Table 1).

Though CD8 is not expressed on human cDCs, said term nevertheless also encompasses human conventional dendritic cells (human cDCs). Human cDCs are sometimes characterized herein as "equivalents of mouse CD8+ DCs" or "eCD8+ conventional dendritic cells", sometimes abbreviated as "eCD8+ cDCs". Human cDCs can be characterized by the features as described herein (see, for example, Table 1), in particular they can be characterized by being recognized by the BDCA3 antibody. In particular, a set of antibodies designated BDCA1-4 has been developed to differentiate between pDCs and subsets of cDCs (Dzionek et al., 2000). On the basis of the recognition of the BDCA3 antibody, the human BDCA3 positive cDCs have been proposed as the human equivalent to mouse CD8+ cDCs. Common to the mouse CD8+ DCs, BDCA3 positive cDCs selectively express high levels of Clec9a and Necl2 but low amounts of CD11b (Shortman et al., 2009). Thus, human BDCA3+ cDCs can also be characterized by the expression of Clec9a and/or Necl2 as described in detail below.

As described above, eCD8+ dendritic cells according to the present invention represent a subset of conventional DCs, and eCD8+ dendritic cells according to the present invention are named eCD8+ cDCs accordingly.

Dendritic cells (DCs) are a heterogeneous population of cells that can be divided into two major populations: (1) non-lymphoid tissue migratory and lymphoid tissue resident DCs and (2) plasmacytoid DCs (pDCs). The term "classic" or "conventional" DCs (cDCs) has recently been used to oppose lymphoid organ-resident DCs to pDCs. Non-lymphoid organ DCs, on the other hand are mainly called tissue DCs. While non-lymphoid tissue DCs are also different from pDCs, and primary non-lymphoid tissue DCs can be found in lymph nodes on migration but are not cDCs, the term cDCs refers to all non-pDCs whether they are present in lymphoid or non-lymphoid tissues.

Within the context of the present invention, an eCD8+ dendritic cell is defined as a conventional, non plasmacytoid dendritic cell which does not depend on GM-CSF for its development. In one embodiment, dendritic cells according to the present invention are isolated as in Example 2. In one embodiment, dendritic cells are isolated as in Example 5.

In accordance with the present invention, precursor cells can be incubated with an agent enhancing CD8+ and/or eCD8+ cDC formation in vitro and in vivo. In a preferred embodiment, the agent enhancing CD8+ and/or eCD8+ cDC formation is a Flt3-ligand or an M-CSF receptor ligand. The addition of a Flt3-ligand can increase the numbers of CD8+ or eCD8+ cDCs 30-fold or more. The administration of a Flt3-ligand to increase CD8+ or eCD8+ cDCs can be combined with stimulation of the CD8+ or eCD8+ cDCs with a ds nucleic acid or analog thereof to increase the production of IFN-λ.

Furthermore, in accordance with the present invention, precursor cells can be incubated with a cytokine. Preferably, the cytokine is selected from the group consisting of IL-3, GM-CSF, IL-4, and IFN-γ.

In one embodiment, dendritic cells according to the present invention are isolated using antibodies against CD8. In one embodiment, dendritic cells are isolated using antibodies against BDCA3. In various embodiments, dendritic cells according to the present invention are isolated using antibodies against Clec9A and/or Necl2. In various embodiments, dendritic cells are isolated using antibodies against Clec9A and/or Necl2 and/or CD205. In various embodiments, dendritic cells are isolated using antibodies against Clec9A and/or Necl2 and/or CD205 and/or CD11c. In various embodiments, dendritic cells are isolated using antibodies against Clec9A and/or Necl2 and/or CD205 and/or CD11c and/or CD24. In various embodiments, dendritic cells are isolated using antibodies against Clec9A and/or Necl2 and/or CD205 and/or CD11c and/or CD24 and/or CD11b. In various embodiments, dendritic cells are isolated using antibodies against Clec9A and/or Necl2 and/or CD205 and/or CD11c and/or CD24 and/or CD11b and/or CD172a. In various embodiments, dendritic cells are isolated using antibodies against Clec9A and/or Necl2 and/or CD205 and/or CD11c and/or CD24 and/or CD11b and/or CD172a and/or MHC-II. In various embodiments, dendritic cells are isolated using antibodies against Clec9A and/or Necl2 and/or CD205 and/or CD11c and/or CD24 and/or CD11b and/or CD172a and/or MHC-II and/or CD103.

Isolation of cDCs according to the present invention can be based on positive expressed surface antigens combined with negative or low expressed surface antigens. Among the highly expressed surface markers on eCD8+ cells are Clec9A, Necl2, CD8, CD103, CD24, CD205, CD36, CD97, CD162, MHC-I, MHC-II, CD11c, and BDCA3 (=CD141), whereas, negative or lower expressed surface antigens that can be used to discriminate DC subsets also from other immune cells are BDCA1 (=CD1c), BDCA2, BDCA4, CD3, CD11b, CD14, CD19, CD20, CD45R, CD45RA, CD172a, PDCA1, BST2, and F4/80 antigen.

The CD8+ cDCs are clearly a functionally distinct DC subset. However, these functional attributes may not always correspond with CD8 expression. Thus, apart from the CD8 molecule, other combinations of surface markers can be used to characterize CD8+ cDC or their functional equivalents that may lack CD8 expression (eCD8+). Among CD11c$^+$ MHC Class II high cells, various combinations of high expression of CD205, CD103, Necl2, Clec9a, CD24 accompanied with negative or low expression of CD11b and CD172a can be used as mentioned herein above. Thus, in various embodiments, the CD8+ and eCD8+ dendritic cells according to the present invention are characterized by positive expressed surface antigens combined with negative or low expressed surface antigens as mentioned above. Furthermore, in various embodiments, the CD8+ and eCD8+ dendritic cells according to the present invention are characterized by the highly expressed surface markers as mentioned above. In a preferred embodiment, CD8+ and eCD8+ dendritic cells according to the present invention have a high expression of Clec9A. In another preferred embodiment, CD8+ and eCD8+ dendritic cells according to the present invention have a high expression of Necl2. In a still further preferred embodiment, CD8+ and eCD8+ conventional dendritic cells according to the present invention have a high expression of Clec9A and/or Necl2. In various embodiments according the present invention, the CD8+ and eCD8+ cDCs according to the present invention are human BDCA3+ dendritic cells.

In various embodiments according to the present invention, the CD8+ and/or eCD8+ cDCs have a high expression of Clec9A and Necl2. High expression of Clec9a and Necl2 can be detected as described in Hochrein et al., 2008, and Shortman et al., 2009, both of which are hereby incorporated by reference.

Therapeutic Applications

In a first aspect, the present invention provides a composition comprising a double-stranded (ds) nucleic acid or analog thereof for use in the induction of IFN-λ production in CD8+ and/or eCD8+ conventional dendritic cells (cDCs), wherein said eCD8+ cDCs express Clec9a and/or Necl2.

In a second aspect, the present invention provides the use of a double-stranded (ds) nucleic acid or analog thereof for the preparation of a pharmaceutical composition for the induction of IFN-λ production in CD8+ and/or eCD8+ conventional dendritic cells (cDCs), wherein said eCD8+ cDCs express Clec9a and/or Necl2.

In a third aspect, the present invention provides a method for inducing IFN-λ production in CD8+ and/or eCD8+ conventional dendritic cells (cDCs), wherein said eCD8+ cDCs express Clec9a and/or Necl2, in a subject in need thereof, comprising the step of administering to said subject a double-stranded (ds) nucleic acid or analog thereof.

IFN-λs possess antiviral, antitumor and various immune modulating functions (Li et al., 2009). Accordingly, the cDCs according to the present invention that produce IFN-λ have a potential antiviral, antitumor and/or immune modulating function. Any of these functions can be used to prevent and/or treat an IFN-λ dependent disease, i.e., a disease the treatment of which with IFN-λ is beneficial for a subject who suffers from such a disease. An IFN-λ dependent disease can be an infectious disease or cancer.

In some embodiments, the IFN-λ dependent disease is a disease of blood, spleen, lung, tonsils, lymph nodes, colon or liver. As described herein, cDCs reside in particular in the blood, spleen, tonsils, lymph nodes and/or liver. Accordingly, it is believed that at these locations, it is highly beneficial to have producers of IFN-λ so that cDCs can exert their antiviral and/or immune modulating activity in order to fight against the causative agents of an infectious disease. The infectious disease may be a viral infection. The viral infection may be caused by a virus that comprises dsRNA or dsDNA, either as its genome or as replication intermediate.

In some preferred embodiments, the viral infection is one described herein, more preferably, it is a persistent viral infection, even more preferably it is a viral infection of the liver or a Herpes virus infection, particularly preferably it is a Hepatitis virus infection. As mentioned above, cDCs reside in the liver ans, thus, it is advantageous to induce the production of IFN-λ directly at the location where the infection is going on.

Similarly, it is assumed that IFN-λ exerts an immune modulating activity, thereby it can activate immune cells which recognize and attack/eliminate cancerous cells such as liver cancer cells.

In view of the foregoing explanations, the present invention provides a method for the prevention and/or treatment of an infectious disease, preferably a viral infection, or cancer, comprising administering to a subject in need thereof a composition comprising a ds nucleic acid or analog thereof targeting CD8+ and/or eCD8+ cDCs. In other words, the present invention provides the use of a composition comprising a ds nucleic acid or analog thereof targeting CD8+ and/or eCD8+ cDCs in the manufacture of a medicament for the prevention and/or treatment of an infectious disease, preferably a viral infection, or cancer.

Also, the present invention provides a combined preparation comprising a ds nucleic acid or analog thereof targeting CD8+ and/or eCD8+ cDCs and an agent enhancing ds nucleic acid-based IFN-λ production.

In some preferred embodiments, the double-stranded (ds) nucleic acid or analog thereof is administered to CD8+ and/or eCD8+ conventional dendritic cells (cDCs) from a subject ex vivo. It is preferred that said cDCs are isolated, i.e., obtained from a subject. Said subject is preferably in need of prevention or treatment of an IFN-λ dependent disease. Said DCs are obtained from the subject by means and methods commonly known in the art. The term "ex vivo", which is interchangeable with the term "in vitro", refers to activities conducted in a controlled environment which is apart from the human body. As used herein and in the art, this term is often used interchangeably with the term "in culture".

The composition as well as the combined preparation provided by the present invention are characterized in that the ds nucleic acid or analog thereof comprised by the composition or combined preparation is targeting CD8+ and/or eCD8+ cDCs. In order to target CD8+ or eCD8+ cDCs, the stimuli for IFN-λ production in those cells, i.e. ds nucleic acids or an analogs thereof, may be coupled to or integrated into carriers, together with one or more surface marker binding molecules for CD8+ and eCD8+ cDCs. Surface marker binding molecules for CD8+ and eCD8+ cDCs may be antibodies to, e.g., CD1d, CD8a, CD11c, CD24, CD36, CD40, CD49f, CD103, CD135, CD141, CD162, CD205, CD207, Necl2, Clec9a, XCR1, TLR10, TLR11, TLR12, and/or TLR13. Thus, in a preferred embodiment, the composition as well as the combined preparation provided by the present invention may comprise a ds nucleic acid or an analog thereof coupled to or integrated into carriers together with one or more of such surface marker binding molecules for CD8+ and eCD8+ cDCs.

Other possibilities include natural or artificial ligands for the surface markers expressed by CD8+ cDCs or eCD8+ cDCs, e.g., glycolipids (for CD1d), MHC-I (for CD8), fibronectin (for CD11c), laminin (for CD49f), CD62P (for CD24), oxidized low-density lipoproteins (for CD36), CD40-ligand (for CD40), E-cadherin (for CD103), Flt3-ligand (for CD135), thrombin (for CD141), P-Selectin (for CD162), mannose, N-acetyl glucosamine or fucose containing molecules (for DEC207), Class-1-restricted T cell-associated molecule (CRTAM) (for Necl2), dead cells (for Clec9a), XCR1-ligand (for XCR1), TLR10-ligand (for TLR10), toxoplasma antigen or profilin (for TLR11), TLR12-ligand (for TLR12), and/or TLR13 ligand (for TLR13). Thus, in a further preferred embodiment, the composition as well as the combined preparation provided by the present invention may comprise a ds nucleic acid or an analog thereof coupled to or integrated into carriers together with one or more of such natural or artificial ligands for the surface markers expressed by CD8+ cDCs or eCD8+ cDCs.

The CD8+ cDC selective binding molecules mentioned above may be directly or indirectly connected to the stimuli (ds nucleic acids or analogs thereof), e.g. by covalent linkage, adaptor molecule binding complexes (e.g., biotin-avidin complexes) binding to microspheres, nanoparticles, virus like particles, and/or liposomes.

When used herein, ds nucleic acid or analog thereof that "targets (or any grammatical form thereof) CD8+ cells and/or eCD8+ conventional dendritic cells" also includes that ds nucleic acids are recognized via certain TLRs. In particular, dsRNA is recognized via TLR-3, dsDNA is recognized via TLR-9 and ssRNA is recognized via TLR-7. Put in other words, "targeting" preferably includes that recognition of dsRNA by cDCs is TLR-3 mediated.

Accordingly, in case of human cDCs, recognition of ds nucleic acids, in particular dsRNA is TLR-3 mediated, i.e, ds nucleic acid, in particular dsRNA is targeted to cDCs via TLR-3.

Notably, human and mouse cDCs do not express TLR-7 and human cDCs do not express TLR-9, either. Nevertheless, dsDNA is recognized by human cDCs as shown in Example 11. Accordingly, dsDNA can be targeted to human cDCs independent of TLRs, i.e., independent of MyD88-dependent TLRs, in particular independent of TLR-7 and/or TLR-9 as described herein.

ds nucleic acids may also be applied in conjunction with dead cells, which are selectively recognized by CD8+ and eCD8+ cDCs via Clec9a and up to now unknown uptake receptors. Dead and dying cells after viral infection in vitro would be another targeted application of ds nucleic acids, which are generated by the cells before death, in conjunction with a selective CD8+ and eCD8+ cDC stimulation. Thus, viral infection of cells in vitro provides dead or dying cells loaded with ds nucleic acid provided by the infecting virus. Such dead and/or dying cells are selectively captured by CD8+ and/or eCD8+ cDCs and elicit IFN-λ production in said CD8+ and/or eCD8+ cDCs by stimulation with the ds nucleic acid provided by the infecting virus. The cells to be used for viral infection in vitro may be any cell as long as such cells are not immunogenic to the subject, to which the dead and/or dying cells loaded with ds nucleic acid of a virus are administered.

In a preferred embodiment, the combined preparation according to the present invention may comprise a ds nucleic acid or analog thereof targeting CD8+ and/or eCD8+ cDCs and an agent enhancing ds nucleic acid-based IFN-λ production, wherein said enhancing agent is a Flt3-ligand, a M-CSF receptor ligand, a TLR2 ligand, a TLR4 ligand, a TLR9 ligand, a TLR10 ligand, a TLR11 ligand, a CD40 ligand, IL-3, GM-CSF, IL-4, or IFN-γ. Since the inventors of the present application found that CD8+ and eCD8+ cDCs produce enhanced amount of IFN-λ by way of combination of ds nucleic acids and other stimuli, wherein the latter themselves do not induce IFN-λ production (e.g. certain TLR ligands (see FIG. 2A) or CD40 ligands), the ds nucleic acid may be applied together with an enhancing stimulus to increase the IFN-λ production. Thus, the linkage of, for example, a CD40 ligand and ds nucleic acid achieves both, targeting to CD8+ cDCs and eCD8+ cDCs, respectively, and enhanced production of CD8+ and/or eCD8+ cDCs-derived IFN-λ. Accordingly, in a preferred embodiment the above described method for the prevention and/or treatment of an infectious disease or cancer comprising administering to a subject in need thereof a composition comprising a ds nucleic acid or analog thereof targeting CD8+ and/or eCD8+ cDCs further comprises the administration of an agent enhancing ds nucleic acid-based IFN-λ production. More preferably, said enhancing agent is a Flt3-ligand, a M-CSF receptor ligand, a TLR2 ligand, a TLR4 ligand, a TLR9 ligand, a TLR10 ligand, a TLR11 ligand, a CD40 ligand, IL-3, GM-CSF, IL-4, or IFN-γ.

In another preferred embodiment, the composition or the composition applied in the methods and uses of the present invention further comprises an agent enhancing ds nucleic acid-based IFN-λ production. Preferably, the agent enhancing ds nucleic acid-based IFN-λ production is a agent which is a TLR-ligand, wherein the TLR-ligand is preferably a TLR2 ligand, a TLR4 ligand, a TLR9 ligand, a TLR10 ligand or a TLR11 ligand; or a TNF-family member, wherein the TNF-family member preferably is a CD40-ligand or a cytokine, wherein the cytokine preferably is a Flt3-ligand, a M-CSF receptor ligand, IL-3, GM-CSF, IL-4, or IFN-γ.

In a preferred embodiment, said agent enhancing ds nucleic acid-based IFN-λ production by of CD8+ and/or eCD8+ conventional dendritic cells (cDCs) is administered to CD8+ and/or eCD8+ cDCs ex vivo. Prior to administration, said cDCs are isolated from a subject.

In another preferred embodiment of the composition or the composition applied in the uses or methods of the present invention further comprises an agent which increases the level of CD8+ and/or eCD8+ conventional dendritic cells (cDCs). Preferably, said agent is a Flt3-ligand or a M-CSF receptor ligand. In other words, in a preferred embodiment the present invention provides a Flt3-ligand or a M-CSF receptor ligand for use in increasing the level of CD8+ and/or eCD8+ cDCs in a subject suffering from an infectious disease or cancer.

In a preferred embodiment, said agent which increases the level of CD8+ and/or eCD8+ conventional dendritic cells (cDCs) is administered to CD8+ and/or eCD8+ cDCs ex vivo. Prior to administration, said cDCs are isolated from a subject.

For example, the present invention provides a method or use for increasing the level of CD8+ and/or eCD8+ cDCs in a subject suffering from an infectious disease or cancer comprising administering to a subject in need thereof an agent which increases the level of CD8+ and/or eCD8+ conventional dendritic cells. Preferably, said agent is a Flt3-ligand or a M-CSF receptor ligand.

The Flt3-ligand or M-CSF receptor-ligand is to be administered to the subject at a dosage sufficient to increase the level of CD8+ and/or eCD8+ cDCs in said subject. In a preferred embodiment, the M-CSF receptor ligand is M-CSF or IL-34. In various embodiments of the method for increasing the level of CD8+ and/or eCD8+ cDCs in a subject suffering from an infectious disease or cancer, a ds nucleic acid or analog thereof can be administered to the subject in addition to a Flt3-ligand or a M-CSF receptor ligand. Said additional administration of a ds nucleic acid or analog thereof stimulates the production of IFN-λ in the subject suffering from an infectious disease or cancer.

Assuming that it appears to be beneficial to increase the level of CD8+ and/or eCD8+ cDCs in a subject, since said cDCs are not abundantly present in a subject, the present invention relates to a composition comprising an agent which increases the level of CD8+ and/or eCD8+ conventional dendritic cells (cDCs), wherein said eCD8+ cDCs express Clec9a and/or Necl2, in combination with a double-stranded (ds) nucleic acid or analog thereof for use in a method of prevention and/or treatment of an IFN-λ dependent disease, comprising (a) administering to a subject said agent which increases the level of CD8+ and/or eCD8+ conventional dendritic cells (cDCs); and (b) administering to a subject a double-stranded (ds) nucleic acid or analog thereof to induce production of IFN-λ in CD8+ and/or eCD8+ conventional dendritic cells.

It is envisaged that steps (a) and (b) are performed subsequent to each other. However, there may be a gap between the performance of both steps. For example, one may await the increase of the number of cDCs before said cDCs are contacted with a ds nucleic acid or analog thereof in order to induce IFN-λ production.

Preferably, the agent which increases the level (i.e., number) of CD8+ and/or eCD8+ conventional dendritic cells (cDCs) is administered in an amount sufficient to increase the level of CD8+ and/or eCD8+ conventional dendritic cells in a subject. An increase is measured by the number of cDCs in comparison to a subject to whom said agent is not administered.

Similarly, it is preferred to administer a double-stranded (ds) nucleic acid or analog thereof in an amount sufficient to induce IFN-λ production in CD8+ and/or eCD8+ cDCs.

As mentioned above, said agent which increases the level (i.e., number) of CD8+ and/or eCD8+ conventional dendritic cells (cDCs) is a Flt3-ligand or a M-CSF receptor ligand or both of them.

Likewise, the present invention provides a method for the prevention and/or treatment of an IFN-λ dependent disease in a subject in need thereof, comprising the steps (a) administering to a subject said agent which increases the level of CD8+ and/or eCD8+ conventional dendritic cells (cDCs); and (b) administering to a subject a double-stranded (ds) nucleic acid or analog thereof to induce production of IFN-λ in CD8+ and/or eCD8+ conventional dendritic cells.

In the alternative, steps (a) and (b) can be carried out ex vivo, i.e, cDCs are isolated from a subject and the agent which increases the level of CD8+ and/or eCD8+ cDCs is administered, followed by the administration of a ds nucleic acid or analog thereof to induce production of IFN-λ in said cDCs.

Given the above, the present invention also provides a method for inducing the production of IFN-λ in a population of cDCs comprising contacting ex vivo cDCs with a ds nucleic acid or analog thereof. As mentioned before, it is preferred that said cDCs are contacted, prior to be contacted with a ds nucleic acid or analog, with an agent which increases the level (number) of cDCs. In particular, for inducing said production of IFN-λ ex vivo, cDCs are obtained from a subject. In the method for inducing the production of IFN-λ in a population of cDCs according to the present invention, the subject from whom the cDCs are obtained is preferably a subject in need of a treatment with cDCs induced to produce large amounts of IFN-λ. Thus, the subject may be a subject in need of a prevention and/or treatment of an INF-λ dependent disease, preferably an infectious disease, preferably a viral infection, or cancer. More preferably, the cDCs may preferably be obtained from a subject suffering from a persistent viral infection, more preferably a viral infection of the liver or a Herpes virus infection, still more preferably a Hepatitis virus infection. Following incubation ex vivo with an agent which increases the level (number) of cDCs and/or a ds nucleic acid or analog thereof, the cDCs are harvested and resuspended in appropriate media for therapy, i.e. for being reintroduced into the subject from whom they were derived. Thus, in the method for inducing the production of IFN-λ in a population of cDCs according to the present invention the cDCs are preferably autologous cDCs. The re-introduction to the subject in need thereof may be carried out by a number of commonly known approaches, like for example intravenous injection. Furthermore, the population of cDCs induced for production of IFN-λ may be re-introduced in a variety of pharmaceutical formulations.

As mentioned, a population of cDCs induced to produce IFN-λ by contacting ex vivo cDCs with ds nucleic or an analog thereof may be administered to a subject in need thereof. Accordingly, the present invention provides a method for inducing a reaction against an IFN-λ dependent disease, preferably an infectious disease or cancer in vivo comprising contacting ex vivo cDCs with a ds nucleic acid or analog thereof and introducing them into a subject suffering from an infectious disease or cancer.

Preferably, said cDCs are contacted before with an agent that increases the number of cDCs. In other words, the present invention provides a method for the prevention and/or treatment of a subject suffering from an IFN-λ dependent disease, preferably an infectious disease or cancer comprising administering to said subject IFN-λ producing cDCs generated by a an ex vivo method for inducing the production of IFN-λ in a population of cDCs, said method comprising contacting ex vivo cDCs with a ds nucleic acid or analog thereof. Preferably, said cDCs are contacted before with an agent that increases the number of cDCs.

In one embodiment, the present invention provides a method for the prevention and/or treatment of an infectious disease or cancer comprising: (a) providing a subject suffering from an infectious disease or cancer; (b) obtaining cDCs from said subject; (c) contacting said cDCs ex vivo with a ds nucleic acid or analog thereof to generate a population of cDCs producing IFN-λ; and (d) re-introducing said population of IFN-λ producing cDCs into said subject so as to induce an in vivo therapeutic reaction against the infectious disease or cancer.

Preferably, step (c) is preceded by step (b'): contacting said cDCs with an agent which increases the number of cDCs.

Preferably, the population of cDCs is washed prior to re-introducing into the subject. In another preferred embodiment, the population of IFN-λ producing cDCs is resuspended in media suitable for administration to the subject in need thereof. The populations of IFN-λ producing cDCs may be re-introduced to the subject by a number of well-known approaches like, for example, intravenous injection.

As mentioned above, it is generally preferred that in all embodiments according to the present invention, which concern and/or include contacting in vivo or ex vivo cDCs with a ds nucleic acid or analog thereof for inducing the production of IFN-λ in a population of cDCs, preferably cDCs which are pre-treated with an agent which increases the level (number) of cDCs, said agent is preferably a Flt3-ligand- and/or M-CSF receptor ligand, are contacted ex vivo or in vivo with a ds nucleic acid or analog thereof. For example, this means that a Flt3-ligand and/or a M-CSF receptor ligand is administered to a subject prior to obtaining the cDCs from said subject for inducing the production of IFN-λ by contacting ex vivo the obtained cDCs with a ds nucleic acid or analog thereof. Alternatively, a Flt3-ligand and/or a M-CSF receptor ligand is administered to cDCs obtained from a subject.

For example, this pretreatment with a Flt3-ligand and/or a M-CSF receptor ligand provides for increasing the formation/ level of cCDs in said subject prior to obtaining such pretreated cDCs from said subject for contacting ex vivo said pretreated cDCs with a ds nucleic acid or analog thereof.

In the context of obtaining cDCs from a subject for contacting ex vivo cDCs with an agent which increases the number of cDCs and/or a ds nucleic acid or analog thereof for inducing the production of IFN-λ in a population of cDCs, methods for obtaining/isolating cDCs from a subject are well-known to the person skilled in the art. In the present invention, the terms "obtaining cDCs from a subject" and "isolating cDCs from a subject" have the same meaning.

In the various embodiments according to the present invention, which concern/include contacting ex vivo cDCs with an agent which increases the number of cDCs and/or with a ds nucleic acid or analog thereof for inducing the production of IFN-λ in a population of cDCs, cDCs obtained/isolated from a subject can be further incubated with a TLR2-, TLR4-, TLR9-, TLR10-, TLR11- or CD40-ligand. This incubation increases the expression of IFN-λ. In various embodiments, the ligand is Pam3Cys, LPS, CpG-ODN, profilin or a CD40-ligand. In various embodiments, the cDCs obtained/isolated from a subject can be further incubated with a cytokine, wherein the cytokine preferably is IL-3, GM-CSF, IL-4, or IFN-gamma (IFN-γ).

In therapeutic applications according to the present invention, the infectious disease is preferably a viral infection. More preferably, in the therapeutic applications according to the present invention the viral infection is a persistent viral infection. Still more preferably, the persistent viral infection is a viral infection of the liver or a Herpes virus infection. In a specifically preferred embodiment, said viral infection of the liver is a Hepatitis virus infection. Accordingly, in the methods for the prevention and/or treatment of an infectious disease or cancer as well as in the methods for increasing the level of CD8+ and/or eCD8+ cDCs in a subject suffering from an infectious disease or cancer, preferably the viral infection is a persistent viral infection, more preferably a viral infection of the liver or a Herpes virus infection, and still more preferably a Hepatitis virus infection. In the present invention, a Hepatitis virus infection includes a Hepatitis A virus infection, a Hepatitis B virus infection, a Hepatitis C virus infection, a Hepatitis D virus infection and a Hepatitis E virus infection, wherein the Hepatitis virus infection preferably is a Hepatitis C virus infection. In another preferred embodiment, in the present invention the persistent viral infection is a retroviral infection.

The subject according to the present invention includes animals and human. In accordance with the present invention, a "subject" shall mean a human or vertebrate animal including a dog, cat, horse, cow, pig, sheep, goat, chicken, monkey, rat, and mouse. In the various embodiments according to the present invention, the subject is preferably human and the eCD8+ cDCs are human BDCA3+ cDCs.

In various preferred embodiments of the present invention, the subject suffering from cancer is a subject suffering from a tumor disease. Preferably, the tumor disease is a carcinoma, i.e. a cancer or tumor of the epithelial cells or epithelial tissue in a subject. Preferably the carcinoma is a squamous cell carcinoma or an adenocarcinoma. More preferably, the carcinoma is squamous cell lung cancer.

In the compositions, uses and methods as well as in the therapeutic applications described above, a ds nucleic acid can be used alone or in combination with one or more other anti-cancer or anti-tumor therapeutic uses and methods, wherein such therapeutic uses and methods are preferably selected from anti-tumor chemotherapy and immunotherapy. Thus, a ds nucleic acid or analog thereof targeting CD8+ and/or eCD8+ cDCs according to the present invention, i.e. which is capable of stimulating or inducing IFN-λ production in CD8+ or eCD8+ cDCs, can be administered prior to, along with or after administration of a chemotherapy or immunotherapy to increase the responsiveness of the malignant cells to subsequent chemotherapy or immunotherapy. Also provided by the present invention is a method for the production of IFN-λ in a subject comprising administering to said subject a ds nucleic acid or analog thereof targeting CD8+ and/or eCD8+ cDCs.

The present invention also provides a combined preparation comprising a ds nucleic acid or analog thereof targeting CD8+ and/or eCD8+ cDCs and an agent enhancing ds nucleic acid-based IFN-λ production. In a preferred embodiment, the agent enhancing ds nucleic acid-based IFN-λ production is a Flt3-ligand, a M-CSF receptor ligand, a TLR2 ligand, a TLR4 ligand, a TLR9 ligand, a TLR10 ligand, a TLR11 ligand, IL-3, GM-CSF, IL-4, or IFN-γ.

In a preferred embodiment, the ds nucleic acid or analog thereof used for therapeutic applications is dsDNA or dsRNA. More preferably, the ds nucleic acid or analog thereof according to the present invention is provided by a dsDNA virus, a dsRNA virus, an ssRNA virus, or a positive ssRNA virus. Thus, in one embodiment, the analog of a ds nucleic acid is an ss nucleic acid, which is processed or can be processed to a ds nucleic acid.

Methods for Producing IFN-λ and/or Generating or Obtaining a Population of IFN-λ Producing CD8+ and/or eCD8+ cDCs The present invention provides a method for producing IFN-λ and/or generating or obtaining a population of IFN-λ producing CD8+ or eCD8+ cDCs, comprising the steps of: (a) providing a population of cells comprising CD8+ and/or eCD8+ cDCs; and (b) contacting the cDCs with a ds nucleic acid or analog thereof. Contacting the cDCs with the ds nucleic acid or analog thereof stimulates the production of IFN-λ. In various preferred embodiments, said population of cells is incubated with an enhancer of IFN-λ production. More preferably, said enhancer is a TLR-ligand or a TNF-family member. Still more preferably, the TLR-ligand is a TLR2-, TLR4-, TLR9-, TLR10- or TLR11-ligand and the TNF-family member is a CD40 ligand or a cytokine. Even more preferably, the cytokine is IFN-γ. The combination of a ds nucleic acid or analog thereof, for example poly IC, and an immunostimulatory CpG DNA, for example CpG-1668, synergistically induces even larger amounts of IFN-λ by CD8+ cDCs.

In various embodiments of the above described methods for producing IFN-λ and/or generating or obtaining a population of IFN-λ producing CD8+ or eCD8+ cDCs, the population of cells is further incubated with a cytokine. Preferably, the cytokine is selected from the group consisting of IL-3, GM-CSF, IL-4, and IFN-γ.

In still another embodiment, the present invention provides thus an in vitro method for producing IFN-λ and/or generating or obtaining a population of IFN-λ producing CD8+ or eCD8+ conventional dendritic cells, wherein said eCD8+ cDCs express Clec9a and/or Necl2, comprising the steps of: (a) providing a population of cells comprising CD8+ and/or eCD8+ conventional dendritic cells;
(b) contacting said conventional dendritic cells with an agent that increases the level of said conventional dendritic cells, preferably Flt3-ligand or M-CSF receptor ligand; and
(c) contacting said conventional dendritic cells with a double-stranded (ds) nucleic acid or analog thereof.

Said contacting may, for example, be achieved by collecting said cDCs in a bag coated with an agent that increases the level of said conventional dendritic cells and/or with a a double-stranded (ds) nucleic acid or analog thereof. Alternatively, said contacting may be achieved by culturing said cDCs.

Preferably, the population of cells is further incubated with an enhancer of IFN-λ production. Said enhancer is preferably, a TLR-ligand, wherein the TLR-ligand is preferably a TLR2 ligand, a TLR4 ligand, a TLR9 ligand, a TLR10 ligand or a TLR11 ligand; or a TNF-family member, wherein the TNF-family member preferably is a CD40-ligand or a cytokine, wherein the cytokine preferably is IL-3, GM-CSF, IL-4, or IFN-γ.

In various preferred embodiments, the above described methods further comprise a step of identifying and/or detecting IFN-λ produced by the ds nucleic acid-stimulated cDCs. In various preferred embodiments, the above described methods still further comprise a step of isolating and/or separating IFN-λ produced by the ds nucleic acid-stimulated cDCs. In other preferred embodiments, the above described methods further comprise a step of identifying and/or isolating and/or separating IFN-λ producing CD8+ and/or eCD8+ cDCs.

The IFN-λ produced by the CD8+ and/or eCD8+ cDCs can be detected and quantitated by techniques well-known in the art, such as those in the examples. The IFN-λ produced by the cDCs in accordance with the present invention can also be collected, isolated, and purified by conventional biochemical techniques.

Thus, the present invention provides a population of IFN-λ producing cDCs obtainable by a method for inducing the production of IFN-λ in a population of cDCs according to the present invention as well as a pharmaceutical composition comprising said population of IFN-λ producing cDCs. Said cDCs are preferably human cDCs.

Preferably, said population of IFN-λ producing cDCs contains more than 10%, 20%, 30%, 40%, 50%, 60%, 70%, 75%, 80%, 85%, 90%, 95%, 96%, 97% 98% or 99% CD8+ and/or eCD8+ cDCs. In various preferred embodiments, the cDCs are preferably human BDCA3+ cDCs. In one embodiment, the population of cells comprising CD8+ and/or eCD8+ cDCs comprises more than 50% eCD8+ cDCs. In another preferred embodiment, the population of cells comprising CD8+ and/or eCD8+ cDCs comprises more than 75% eCD8+ cDCs. In a further preferred embodiment, the population of cells comprising CD8+ and/or eCD8+ cDCs comprises more than 85% eCD8+ cDCs.

In one embodiment, the population of cells comprising CD8+ and/or eCD8+ cDCs comprises more than 50% human BDCA3+ cDCs. In another preferred embodiment, the population of cells comprising CD8+ and/or eCD8+ cDCs comprises more than 75% human BDCA3+ cDCs. In a further preferred embodiment, the population of cells comprising CD8+ and/or eCD8+ cDCs comprises more than 85% human BDCA3+ cDCs.

As described above, the present invention provides a population of IFN-λ producing CD8+ and/or eCD8+ cDCs or a cell line of an IFN-λ producing CD8+ and/or eCD8+ cDC, obtainable by the above described methods for generating or obtaining a population of IFN-λ producing CD8+ or eCD8+ cDCs. Furthermore, the present invention provides a pharmaceutical composition comprising a population of IFN-λ producing CD8+ and/or eCD8+ cDCs obtainable by the above described methods for generating or obtaining a population of IFN-λ producing CD8+ or eCD8+ cDCs. In various preferred embodiments, said a pharmaceutical composition optionally further comprises a pharmaceutically acceptable carrier or diluent.

Methods for Detecting or Screening for CD8+ and eCD8+ cDCs

IFN-λ production in response to a ds nucleic acid or an analog thereof, for example poly IC, can be used to detect, diagnose or screen for the presence of eCD8+ cDCs even in complex mixtures of different cells and even if the amount of eCD8+ cDCs is very low (see FIG. 3A). IFN-λ can be used as a marker for finding the CD8+ and/or eCD8+ subsets of cells, which thus can be targeted in certain situations, for example when it is desirable to increase the amount of CD8+ and/or eCD8+ cDCs.

The present invention encompasses methods for detecting or screening for the presence of CD8+ and/or eCD8+ cDCs. In particular, the present invention provides an in vitro method for detecting or screening for CD8+ and/or eCD8+ cDCs, comprising the steps of: (a) providing a population of cells; (b) contacting the cells with a ds nucleic acid or analog thereof capable of stimulating or inducing the production of IFN-λ in CD8+ and/or eCD8+ cDCs; (c) detecting the production of IFN-λ; and (d) correlating the production of IFN-λ with the presence of CD8+ and/or eCD8+ cDCs. In various preferred embodiments, said method is a method for detecting or screening for the presence of CD8+ and/or eCD8+ cDCs in a biopsy, preferably a biopsy of an organ or blood. Thus, a biopsy of an organ or blood can be checked for the presence of those cells via their unique IFN-λ production in response to a ds nucleic acid or an analog thereof. Since the production of IFN-λ is quite constant after induction, one can quantitate the amount of the specific CD8+ and/or eCD8+ cDCs in, for example, the body of a subject or cell culture. Thus, one can detect/diagnose and determine conditions where the amount of CD8+ and/or eCD8+ cDCs is increased or decreased. In various embodiments, the method for detecting or screening for CD8+ and/or eCD8+ cDCs further comprises a step of separating and/or isolating IFN-λ producing CD8+ and/or eCD8+ cDCs. The methods may further comprise measuring the IFN-λ production from said separated and/or isolated IFN-λ producing cDCs.

The IFN-λ produced by the CD8+ and/or eCD8+ cDCs can be detected and quantitated by techniques well-known in the art, such as those in the examples. The IFN-λ produced by the dendritic cells in accordance with the present invention can also be collected, isolated, and purified by conventional biochemical techniques.

In a further aspect, the present invention relates to an in vitro method for detecting or screening for human CD8+ and/or eCD8+ conventional dendritic cells, comprising the steps of:
(a) providing a population of cells comprising human dendritic cells;
(b) selecting BDCA3+ dendritic cells
(c) contacting said BDCA3+ cells with a double-stranded (ds) nucleic acid or analog thereof;
(d) detecting the production of IFN-λ; and
(e) correlating the production of IFN-λ with the presence of CD8+ and/or eCD8+ conventional dendritic cells.

In a preferred embodiment, step (c) may be preceded by the (b'): contacting said BDCA3+ cells with an agent which increases the number of said BDCA3+ cells. Said step b' may aid in amplifying the detection of IFN-λ production, since more BDCA3+ cells will be present that can thus produce more IFN-λ.

Preferably, said method is for screening or detecting the presence of human CD8+ and/or eCD8+ conventional dendritic cells in a biopsy, preferably a biopsy of an organ or blood.

BRIEF DESCRIPTION OF THE DRAWINGS

FIG. 5 depicts human BDCA3+ cDCs are major producers of IFN-λ upon poly IC stimulation. PBMC, PBMC depleted of BDCA1 and 3, or cells selected for BDCA1 or BDCA3 were stimulated in the presence of IL-3, GM-CSF and IFN-γ with (donor 1) 100 μg/ml poly IC+10 μg/ml Pam3Cys+10 μg/ml LPS or with (donor 2 and 3) 100 μg/ml poly IC for 18-24 h. Supernatants were analyzed for IFN-λ1 and IFN-λ2. The experiments are shown for the individual donors and data represent mean+/−SD of duplicate samples.

FIGS. 10A-D depict that TLR3 and IFN-AR, but not MyD88 or Cardif, are involved in IFN-λ production to poly IC by FLDC-derived eCD8+ cDCs. Sorted FLDC eCD8+5×10$^5$/ml from mice as indicated were stimulated for 18 h and supernatants were analyzed for IFN-λ. (A) WT and MyD88-KO eCD8+ DCs stimulated with poly IC in the presence of IL-4 and IFN-γ. (B) WT and TLR3-KO eCD8+ DCs stimulated with poly IC in the presence of IL-3+IL-4+IFN-γ+GM-CSF. (C) WT and Cardif-KO eCD8+ DC stimulated with poly IC+CpG-1668 in the presence of IL-3 and GM-CSF. (D) WT and IFN-AR-KO eCD8+ DC stimulated with poly IC+profilin in the presence of IL-3 and GM-CSF. Representative results of at least 2 independent experiments are shown. Data represent mean+/−SD of duplicate samples.

FIG. 14 depicts that CD40 costimulation enhances poly IC induced IFN-λ production in vivo. Mice were injected (i.v.) with poly IC (100 µg), anti-CD40 mAb (100 µg) or the combination of poly+anti-CD40 (100 µg each). After 3-4 h sera were analyzed for IFN-λ and IFN-α. Circles indicate the results of individual mice and their total number (n) is indicated in the graph. The columns represent the mean of all mice used. Three (IFN-λ) or two (IFN-α) independent experiments have been performed.

FIG. 20 depicts that in vivo and in vitro FL generated CD8α+ cDCs, eCD8α cDCs and pDCs are major producers of IFN-λ to HSV-1 and parapoxvirus. Highly purified (A) FL expanded ex-vivo isolated splenic or (B) generated in vitro from BM with FL DC subsets 5×10$^5$/ml were stimulated in the presence of IL-3+GM-CSF+IL-4+IFN-γ with the stimuli as indicated. After 18 h supernatants were analyzed for IFN-λ. Bars represent the mean±SD of 2 independent experiments each using a pool of at least 2 mice per experiment.

EXAMPLES

Figure 1:
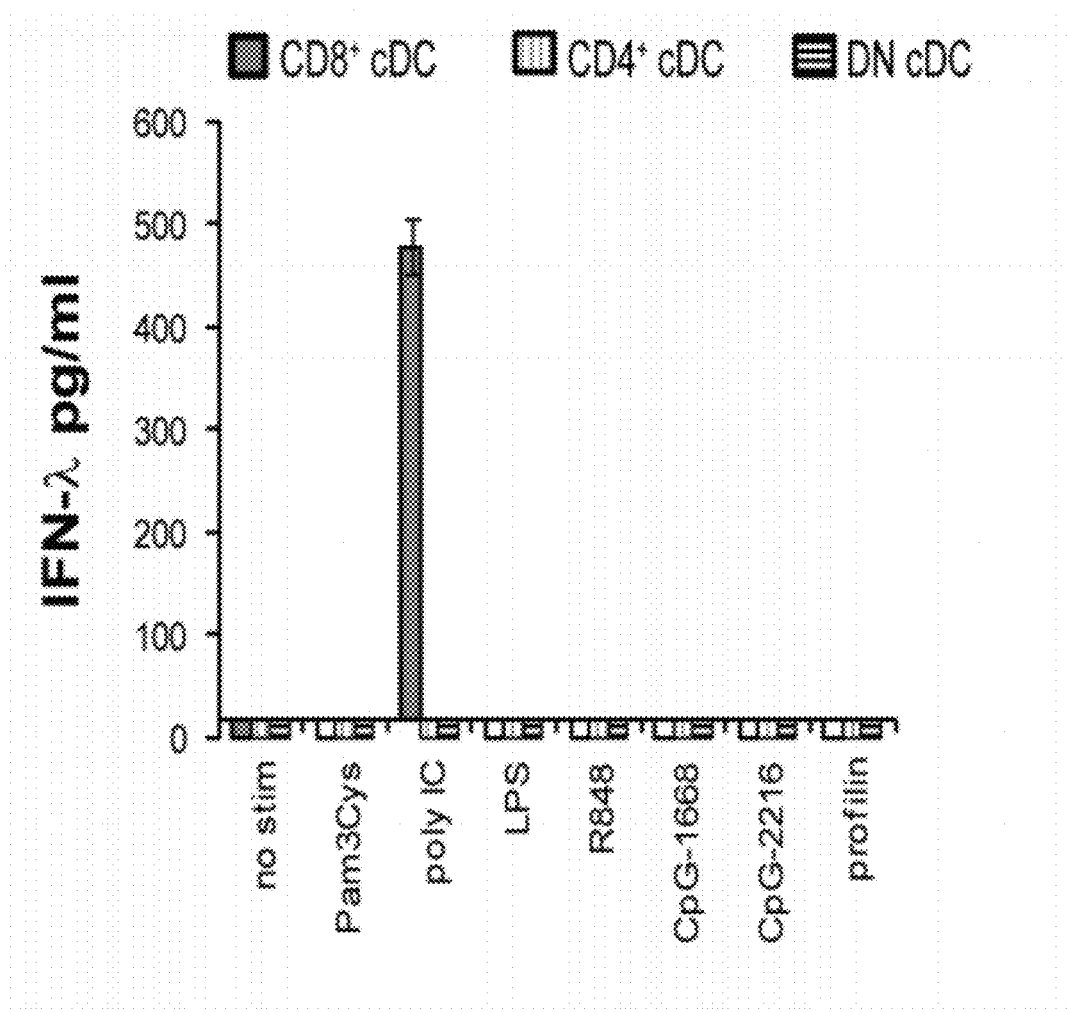
FIG. 1 depicts splenic CD8+ cDC are the major producers of IFN-λ in response to poly IC. Highly purified splenic cDC subsets $5 \times 10^5$/ml were stimulated in the presence of IL-3 and GM-CSF with the stimuli as indicated in the examples. After 18 hours, supernatants were analyzed for IFN-λ. Representative results of 3 independent experiments are shown. Data represent mean+/−SD of duplicate samples.

The present invention is further illustrated by the following Examples, which in no way should be construed as further limiting. The entire contents of all of the references cited throughout this application are hereby expressly incorporated by reference.

1. Mice

MyD88-KO mice were from S. Akira (Adachi et al., 1998), Cardif-KO mice were from J. Tschopp (Meylan et al., 2005), TLR3-KO mice were from The Jackson Laboratory (Alexopoulou et al., 2001), IRF7-KO mice from Tadatsugu Taniguchi (Honda et al., 2005) and IFN-AR-KO mice were originally from Michel Aguet (Muller et al., 1994). C57BL/6 WT mice were purchased from Harlan Winkelmann.

2. Cells and Flow Cytometric Sorting

DC subsets were isolated from pooled mouse spleens as described (Vremec et al., 2007). Briefly, spleens were chopped, digested with collagenase (Worthington Biochemical) and DNase (Roche) at room temperature, and treated with EDTA. Low-density cells were enriched by density centrifugation; non-DC lineage cells were coated with mAbs (anti-CD3, KT3-1.1; anti-Thy-1, T24/31.7; anti Gr-1, 1A8; anti-CD19, ID3; anti-erythrocytes, TER119 and anti-NK cells, DX5) and depleted using anti-rat Ig magnetic beads (Qiagen). Dead cells were excluded by propidium iodide staining. cDC populations were sorted based on the expression of CD11c, CD45RA, CD4, CD8a and CD172a and pDCs were purified based on CD11c, CD45RA, and CD172a (all BD Biosciences) expression. Cell sorting was performed on a FACS Aria instrument (BD Biosciences).

FL bone marrow culture derived dendritic cells (FLDC) were prepared as described (Hochrein et al., 2004). pDCs and eCD8+ and eCD8− cDC subsets were sorted based on the expression of CD11c, CD45R, CD11b, CD24, and CD172a or CD103 (all BD Biosciences).

3. In Vivo Challenge with Poly IC

Mice were injected i.v. into the lateral tail vein with 100 µg poly IC (Axxora) and serum was collected 3-4 h after challenge. Sera were pre-diluted 1/5, IFN-λ was analyzed by ELISA as described (Hochrein et al., 2004). IFN-λ was determined by an IFN-λ3 (IL-28B) ELISA (R&D Systems). This ELISA is largely cross-reactive to IFN-λ2 (IL-28A) and does not differentiate between these two mouse IFN-λs.

4. In Vitro Stimulation and Cytokine Detection

Cells were stimulated in vitro with single TLR agonists or combinations thereof containing 10 µg/ml Pam3Cys (InvivoGen), 100 µg/ml poly IC (Axxora), 10 µg/ml LPS (*E. coli*; Sigma-Aldrich or Axxora), 10 µg/ml R848 (Axxora), 1 µM CpG-1668 or CpG-2216 (TIB-Molbiol), 1 µg/ml profilin of toxoplasma (Axxora). The recombinant cytokines mouse-IL-3, mouse-IL-4, rat-IFN-γ (PeproTech) and mouse-GM-CSF (Tebu-Bio) (10 ng/ml each) were added as indicated. The addition of IL-3 and GM-CSF was based on previous observations that GM-CSF promoted the production of IL-12p70 and that the combination of IL-3 and GM-CSF increased virus induced IFN-λ production in pDCs and cDCs (Hochrein et al., 2000; Hochrein et al., 2004). As source of a parapoxvirus Zylexis, which is used for veterinary purposes was purchased from a pharmacy. HSV-1, in replication deficient form known as disc HSV-1 (HSV-1d) was used as described (Hochrein et al., 2004). IFN-λ in supernatants was analyzed by ELISA and IL-12p70 was determined by FlowCytomix bead assay (Bender Medsystems) according to manufacturer's protocol.

5. Isolation and Stimulation of Human DC

PBMC were prepared from peripheral blood of non-atopic blood donors by density gradient centrifugation and BDCA3+ DC were purified from PBMC using the BDCA3/CD141+Dendritic Cell Isolation Kit (Miltenyi Biotech) on an AutoMACS™ separator. Subsequently, BDCA1+ DC were purified from the BDCA3-depleted PBMC using the BDCA1/CD1c+ Dendritic Cell Isolation Kit (Miltenyi Biotech). Preliminary experiments with PBMC and DC enriched fractions of PBMCs have indicated that the addition of the recombinant human cytokines IL-3, GM-CSF and IFN-γ (all PeproTech) (10 ng/ml each) enhanced the IFN-λ1 and IFN-λ2 production and accordingly this combination of cytokines was added to all stimulations shown. After stimulation for 18-24 h the supernatants were analyzed for IFN-λ1 and IFN-λ2 by ELISA according to manufacturer's recommendations (Tebu-bio).

6. CD8+ cDCs are the Major Producers of IFN-λ in Response to Poly IC

Poly IC, well know for its ability to induce large amounts of IFN-I, has also been described as a potent inducer of IFN-λ (Kotenko et al., 2003; Sheppard et al., 2003). pDCs were identified as major producers of IFN-λs in response to several viruses or to CpG-ODN stimulation but the cellular source of poly IC induced IFN-λ remains elusive (Coccia et al., 2004; Ank et al., 2008).

Figure 8:
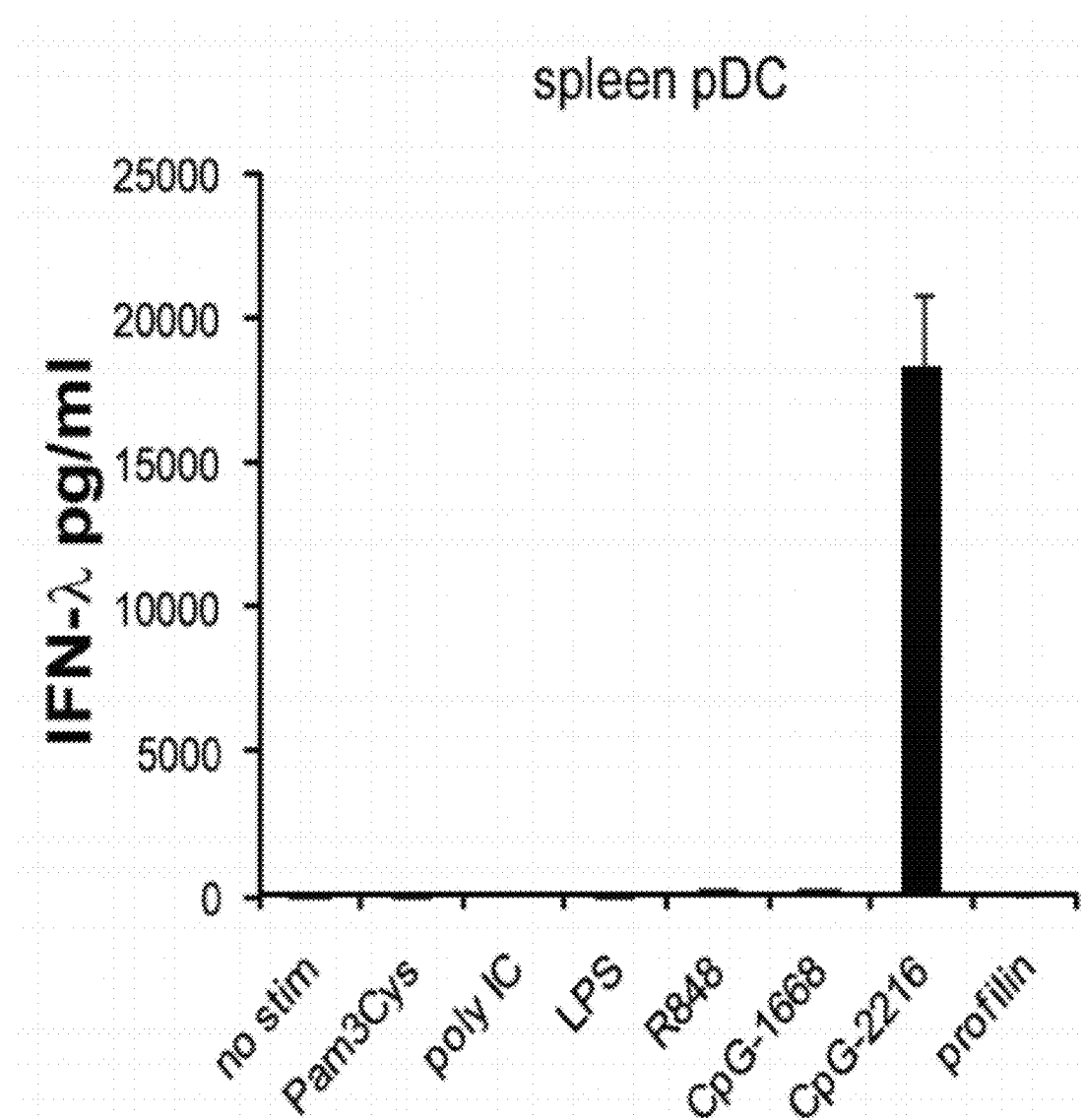
FIG. 8 depicts splenic pDCs produce large amounts of IFN-λ to CpG-2216. Highly purified splenic pDCs $5 \times 10^5$/ml were stimulated in the presence of IL-3 and GM-CSF with the stimuli as indicated. After 18 h supernatants were analyzed for IFN-λ. Representative results of 3 independent experiments are shown. Data represent mean+/−SD of duplicate samples.
Figure 9:
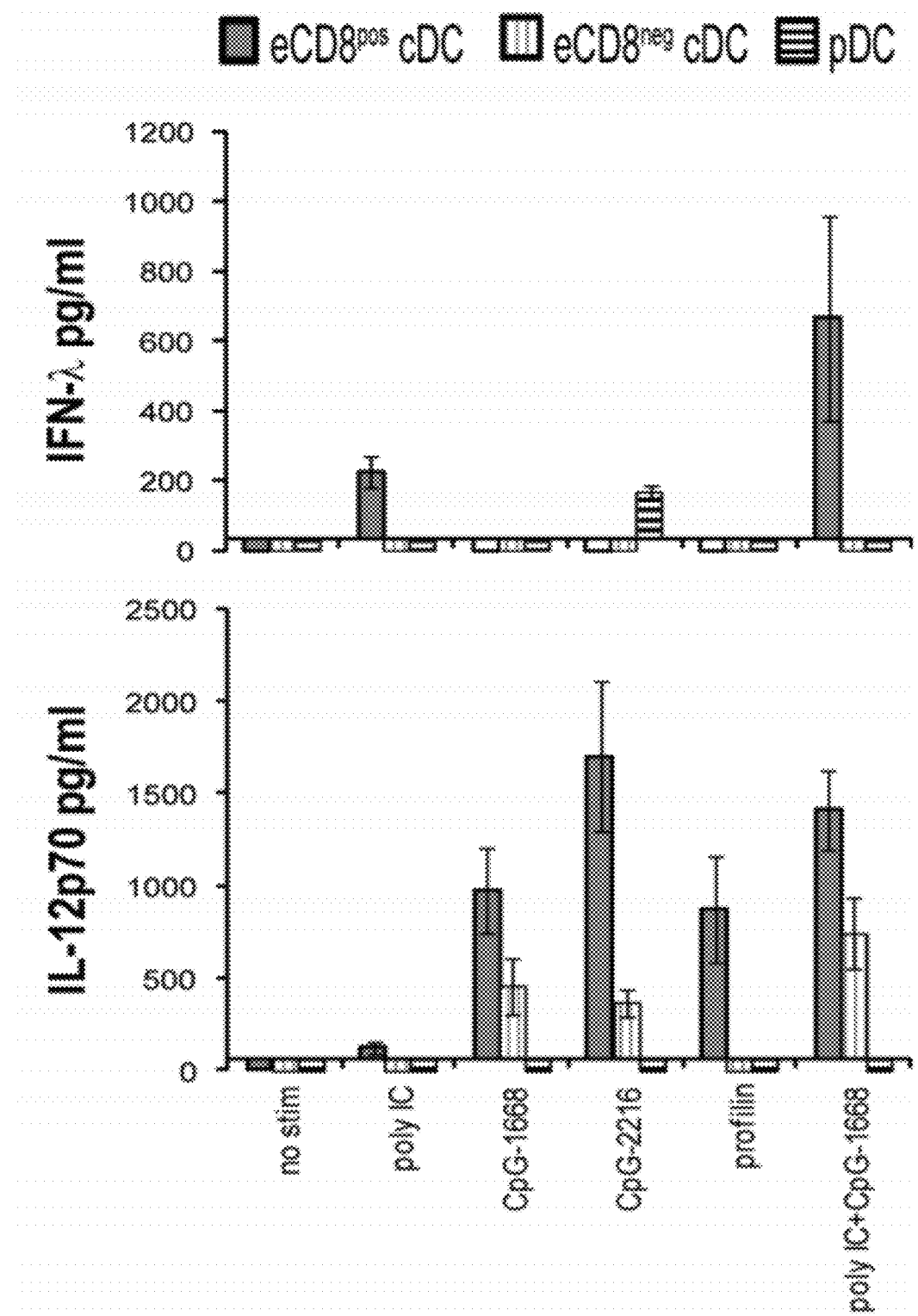
FIGS. 9A and B depict sorted FLDC-derived eCD8+ cDCs are major producers of IFN-λ to poly IC. Sorted FLDC subsets 2.5×10$^5$/ml were stimulated for 18 h and supernatants were analyzed for IFN-λ and IL-12p70. (A) Stimulated in the presence of IL-4 and IFN-γ with the stimuli as indicated. (B) Stimulated in the presence of poly IC+CpG-1668 with the cytokines as indicated. Representative results of 2 independent experiments are shown. Data represent mean+/−SD of duplicate samples.
Figure 9:
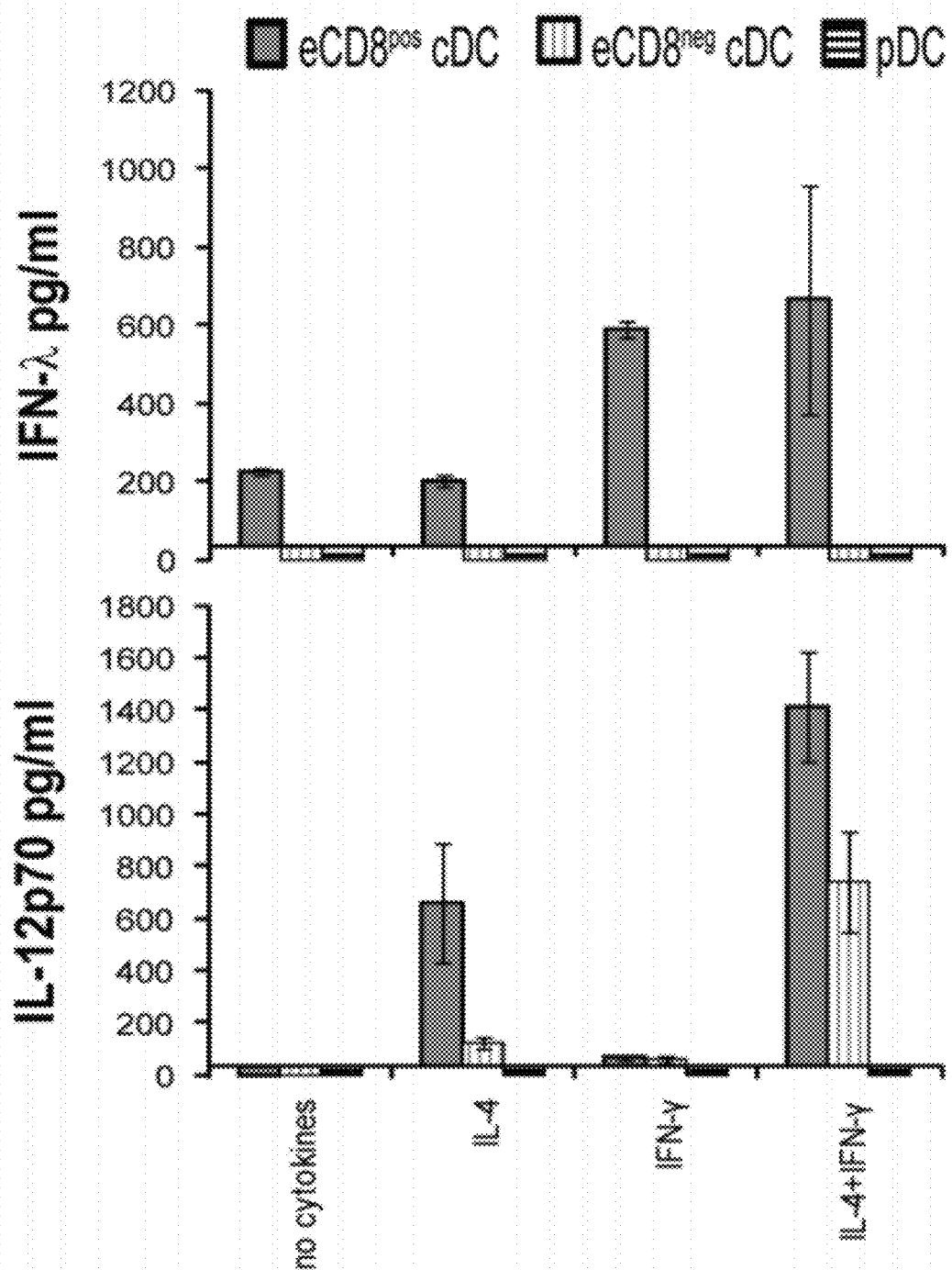

Stimulation of fractionated spleen cells with a panel of TLR ligands revealed that the major lymphocyte fractions consisting of T- and B-lymphocytes were unable to produce IFN-λ whereas all IFN-λ production was confined to enriched preparations of DCs. Among highly purified splenic DC subsets the pDCs, as previously reported, were the major source of IFN-λ in response to the A-type ODN CpG-2216 (FIG. 8). However in response to poly IC stimulation the CD8+ cDCs were the major producers, with pDCs and CD8-cDCs being largely unable to participate in IFN-λ production (FIG. 1 and FIG. 8). In vitro generated FLDC subsets were also examined. As for ex vivo isolated pDC and cDC subsets, the eCD8+, but not the eCD8-cDCs or the pDC, produced IFN-λ to poly IC (FIG. 9 A). Thus, CD8+ cDCs and their in vitro equivalents are the major producers of IFN-λ in response to poly IC stimulation.

7. IFN-λ and IL-12p70 Production by CD8+ cDCs Depends on the Type of Stimulus and the Cytokine Conditions CD8+ cDCs are well known for their exceptional capacity for IL-12p70 production. Since it was found that the CD8+ cDCs were also able to produce large amounts of IFN-λ, the conditions that would govern IFN-λ were compared to those governing IL-12p70 production. Using a panel of TLR stimuli, it was found that TLR-ligands known for their high IL-12p70 induction, such as CpG-ODN or profilin of toxoplasma (Hochrein et al., 2000; Yarovinsky et al., 2005), induced large amounts of IL-12p70, as expected, but surprisingly under these conditions the CD8+ cDCs did not produce any IFN-λ. In contrast, poly IC induced IFN-λ but not IL-12p70 production by CD8+ cDCs (FIG. 2A). Combinations of poly IC together with Pam3Cys, LPS, CpG-ODN or profilin, ligands for TLR2, TLR4, TLR9, TLR10 or TLR11, respectively, synergistically increased IFN-λ production (FIG. 2A). In line with a lack of TLR7 and thus unresponsiveness of CD8+ cDCs to TLR7 stimulation, R848 was unable to support poly IC induced IFN-λ production (FIG. 2A). These data demonstrate a synergistic increase of poly IC induced IFN-λ with myeloid differentiation primary response gene 88 (MyD88)-dependent stimuli and confirm described synergistic effects on the production of IL-12p70 by CD8+ cDCs (FIG. 2A) (Napolitani et al., 2005).

Figure 2:
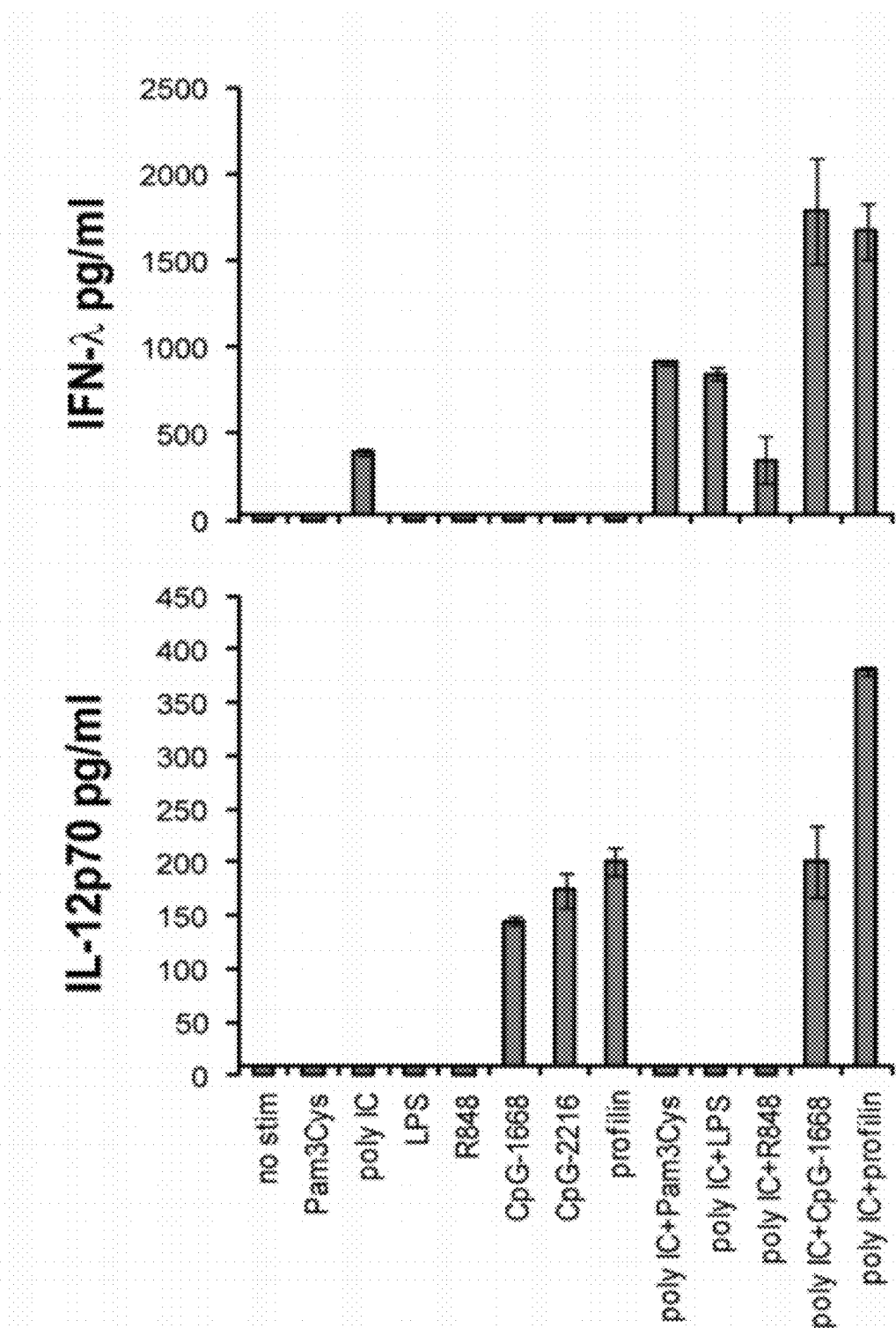
FIGS. 2A-C depict the production of IFN-λ or IL-12p70 by CD8+ cDCs depends on the stimuli and the cytokine conditions. Sorted splenic CD8+ cDC $5 \times 10^5$/ml were stimulated and supernatants were analyzed after 18 hours for IFN-λ and IL-12p70. (A) Stimulation in the presence of IL-3 and GM-CSF with the stimuli as indicated. (B) Stimulation with a combination of poly IC+CpG-1668 with the cytokines as indicated. (C) Stimulation in the presence of IL-3+IL-4+IFN-γ+GM-CSF with the stimuli as indicated. Representative results of at least 2 independent experiments are shown. Data represent mean+/−SD of duplicate samples.
Figure 2:
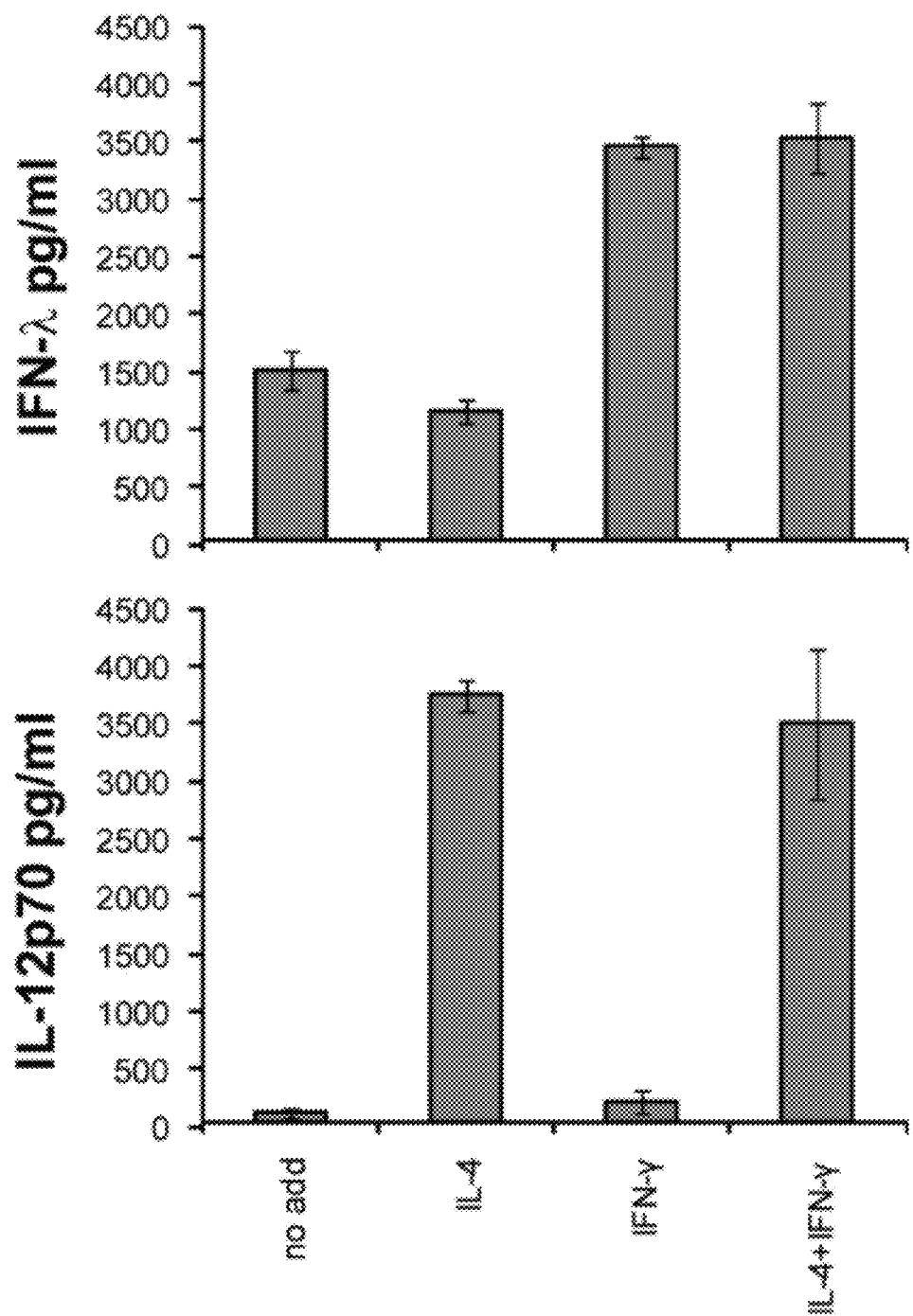
Figure 2:
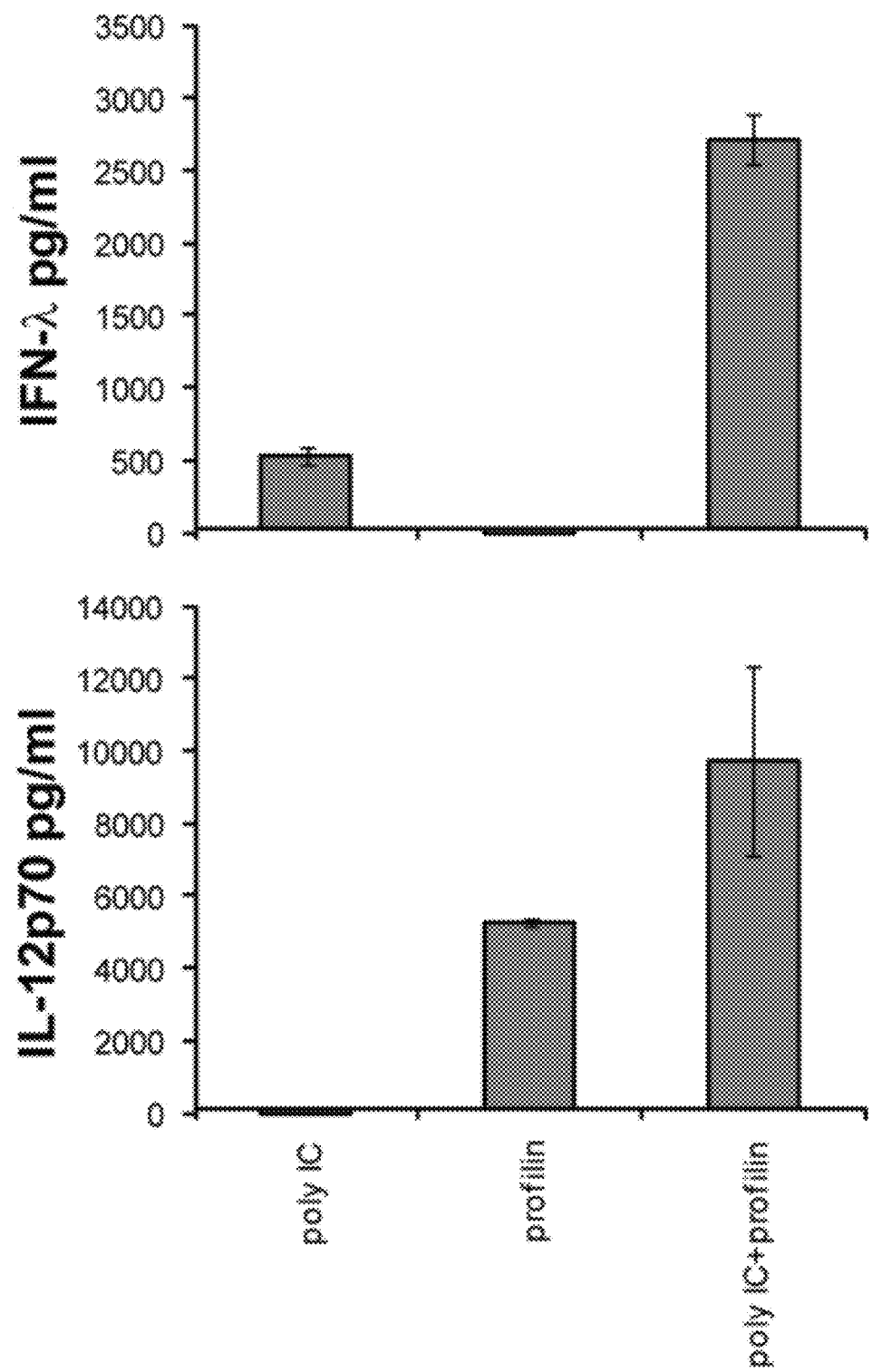

It has been previously shown that the cytokine milieu during stimulation is highly influential for IL-12p70 production in murine and human DCs, with IL-4 being a major enhancer for bioactive IL-12 production (Hochrein et al., 2000; Kalinski et al., 2000). Using a combinatory stimulus (poly IC+CpG-1668), which induced both IFN-λ and IL-12p70, it was found that IFN-γ enhanced the production of IFN-λ with little effects on IL-12p70 production, whereas IL-4 increased IL-12p70, but not IFN-λ production (FIG. 2B). Combining IL-12p70 and IFN-λ enhancing cytokines (IL-3+GM-CSF+IL-4+IFN-γ) with single stimuli (poly IC or profilin) demonstrated that the stimulus-dependent mutually exclusive production of IFN-λ or IL-12p70 by CD8+ cDCs was preserved (FIG. 2C). However, combinations of stimuli (poly IC+CpG-1668 or poly IC+profilin) plus cytokines enabled the production of large amounts of IFN-λ and IL-12p70 at the same time (FIGS. 2, B and C).

Compared to the ex vivo isolated splenic DC subsets, FACS-sorted pDC, eCD8+ cDCs and eCD8-cDCs from FLDC demonstrated a very similar subset specificity as well as stimulus and cytokine dependence for IFN-λ production (FIG. 9). Thus as described for other functional parameters such as IL-12p70 production or cross-presentation, the IFN-λ production of eCD8+ cDCs from FL cultures demonstrates a high degree of functional similarity to ex vivo isolated CD8+ cDCs.

8. FL is Involved in IFN-λ Production to Poly IC In Vivo

FL is a growth factor involved in the development of DCs in the steady state and mice deficient for FL (FL-KO) have drastically reduced amounts of DCs including pDCs and CD8+ cDCs (McKenna et al., 2000). To define the role of DCs as a source of IFN-λ in organs other than spleen, liver cells were isolated from wild type and FL-KO mice and stimulated them under cytokine conditions for expression of both IFN-λ and IL-12p70 induction with either solely poly IC or profilin or a combination thereof. As found with sorted CD8+ or eCD8+ cDCs (FIG. 2 and FIG. 8 B), liver cells from WT mice produced IFN-λ to poly IC and IL-12p70 to profilin whereas the combination of both stimuli supported the production of IFN-λ and IL-12p70 simultaneously (FIG. 3A). In contrast, liver cells of FL-KO mice displayed a largely abrogated production of IFN-λ as well as IL-12p70 to this stimulation (FIG. 3A). Since non-hematopoietic cells and most non-DC populations are believed to be normal in FL-KO mice, this suggests that DCs were the major source of the IFN-λ produced. CD8+ or eCD8+ cDCs, but not pDCs or other cDC subsets, selectively express TLR11 and thus are selectively able to respond to profilin and to produce IL-12p70 (FIG. 2 and FIG. 9A) (Yarovinsky et al., 2005). The concomitant abrogation of IFN-λ and IL-12p70 in FL-KO liver cells upon stimulation selective for CD8+ and eCD8+ cDCs strongly suggests that this cDC subset is the source of the IFN-λ produced and points to a prominent role for eCD8+ cDCs as a major source of IFN-λ in the liver in vivo. Thus, the IFN-λ production under those selective stimulatory conditions might serve as an indicator for CD8+ cDC, even in a complex mixture of different cell types.

Figure 11:
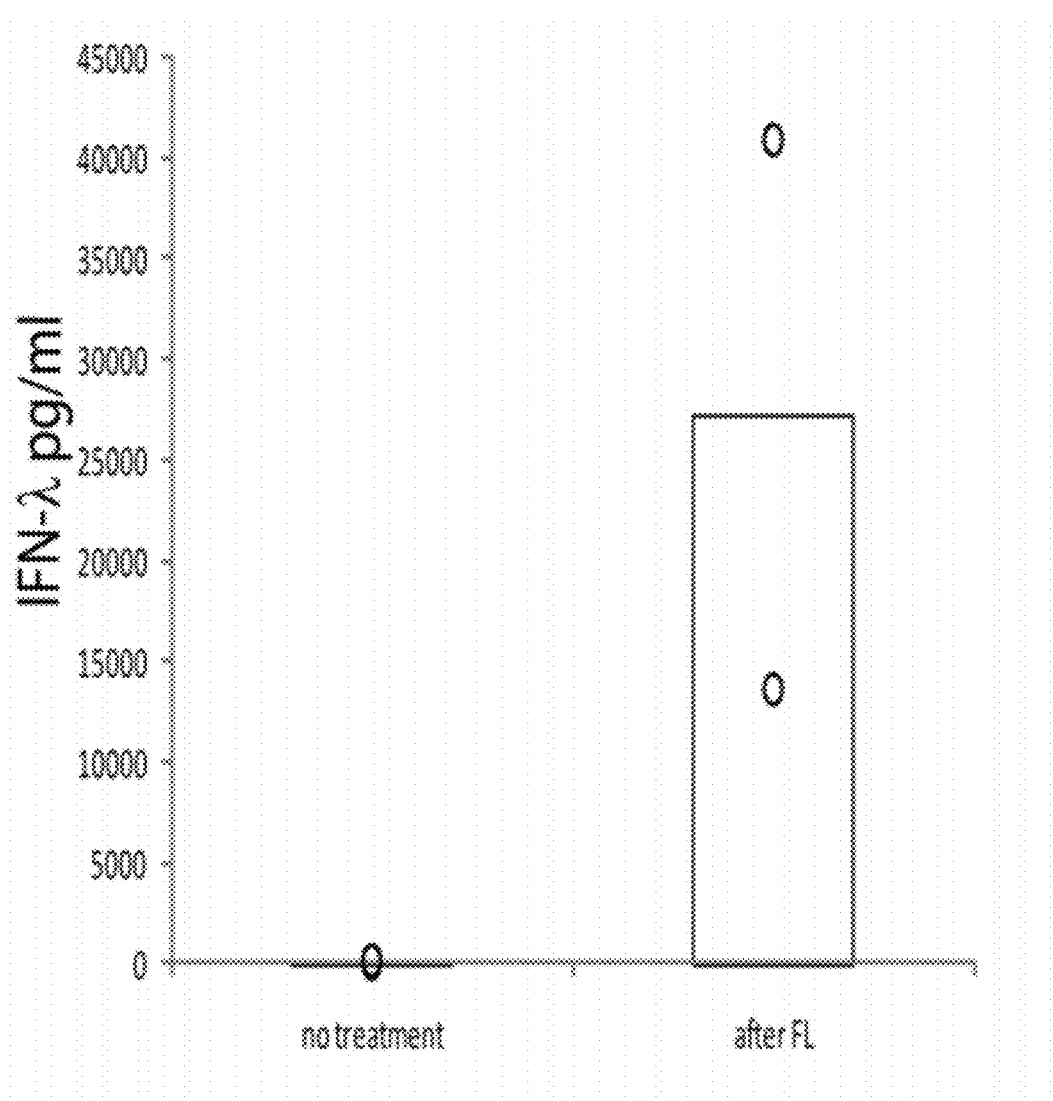
FIGS. 11A and B depict the production of IFN-λ in vivo can be increased with treatment of FL or M-CSF. FL-KO mice were treated for 7 consecutive days with 10 µg of recombinant FL (A) or M-CSF (B) per day. The next day after growth factor treatment mice were injected i.v. with 100 µg poly IC. After 3-4 h sera were analyzed for IFN-λ. Circles indicate the results of individual mice and columns represent the mean thereof.
Figure 11:
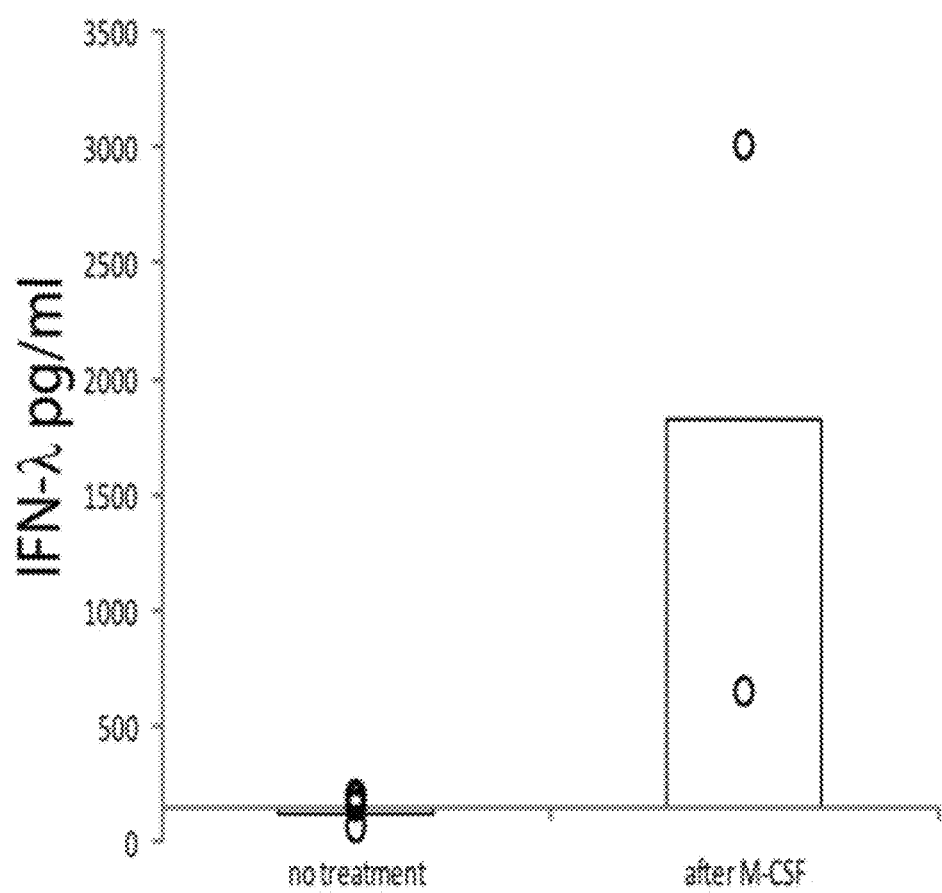

To extend these observations to a direct in vivo challenge, the response of WT and FL-KO mice to poly IC injection was compared. Serum levels of IFN-λ in response to poly IC were easily detectable in WT mice as were the levels of IFN-α. In sharp contrast, in FL-KO mice the levels of IFN-λ were almost abrogated, whereas IFN-α remained easily detectable (FIG. 3B). Application of recombinant FL into FL-KO mice not only restored, but even increased, their IFN-λ producing capacity above WT level (FIG. 11A). Application of M-CSF into FL-KO mice was also able to increase IFN-λ production to poly IC demonstrating that M-CSF is able to increase the number of IFN-λ producers to poly IC (FIG. 11B). Along those lines, FL treated WT mice which display elevated DC numbers, including CD8+ cDCs, had a greatly increased systemic IFN-λ response to poly IC challenge. The FL dependence strongly suggests that the IFN-λ production to poly IC in vivo is largely mediated by DC. Moreover these data indicate that the CD8+ and eCD8+ cDC subsets are responsible.

9. TLR3, IFN-AR and IRF7 are Involved in IFN-λ Production to Poly IC In Vivo

Figure 4:
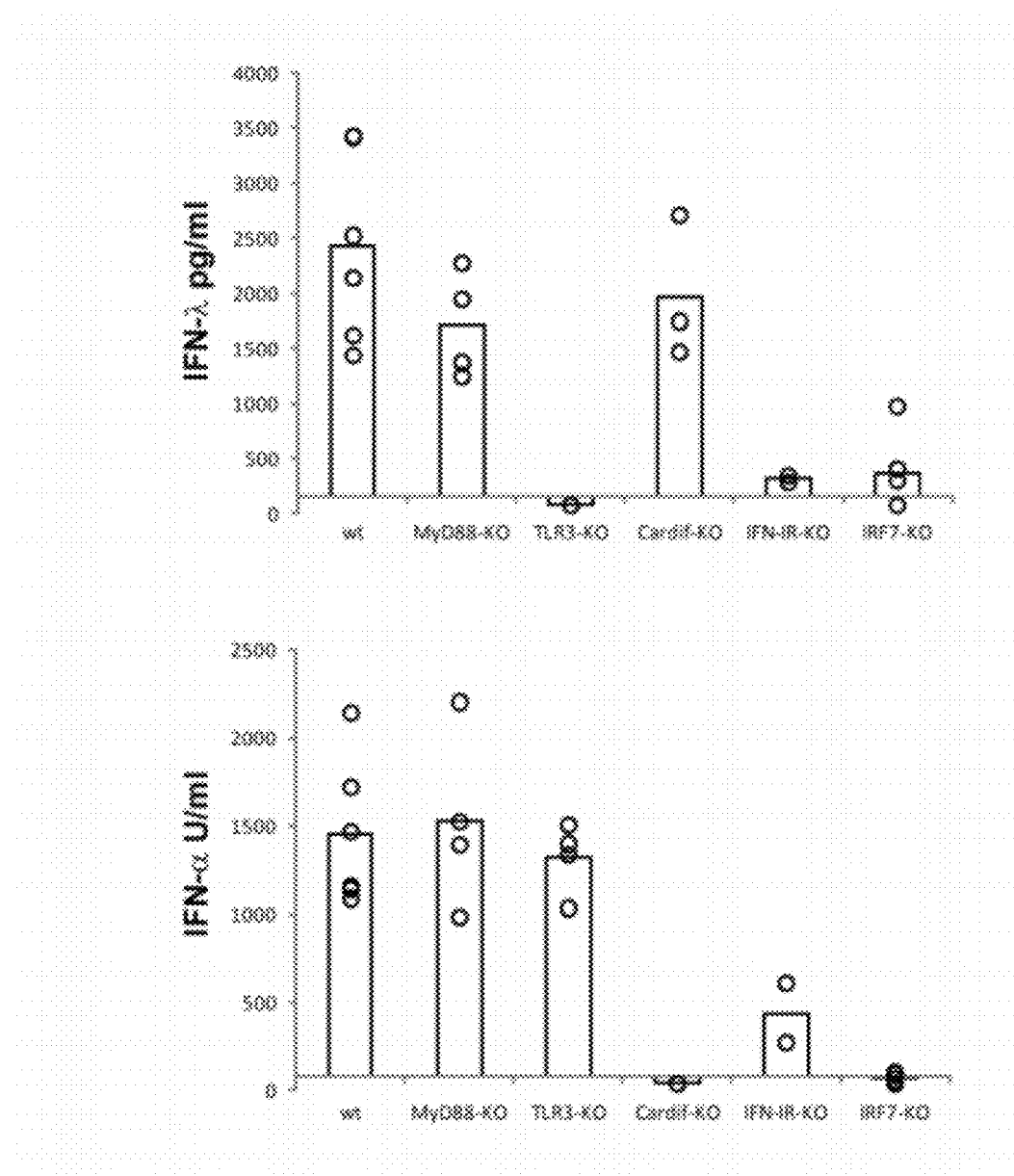
FIG. 4 depicts that TLR3, IFN-AR and IFR7, but not MyD88 or Cardif, are involved in IFN-λ production to poly IC in vivo. Mice with the indicated genotype were injected i.v. with 100 μg poly IC. After 3-4 h sera were analyzed for IFN-λ and IFN-α. Circles indicate the results of individual mice and columns represent the mean thereof.

Poly IC is detected by the immune system in redundant ways and roles for RLH as well as TLR3 have been described (Alexopoulou et al., 2001; Gitlin et al., 2006). To determine the pattern recognition receptors involved in the poly IC induced IFN-λ production in vivo, poly IC was injected into mice deficient for various pattern recognition receptors or their adaptor molecules, specifically TLR3, MyD88 or Cardif and IFN-λ as well as IFN-α were measured in the corresponding sera (FIG. 4). Large amounts of IFN-λ and IFN-α were induced in WT mice and MyD88-KO, demonstrating that MyD88-dependent TLRs were not involved and suggesting that pDC, which largely depend on MyD88 for IFN production, did not likely contribute to the production of both cytokines under those conditions. However, deficiency of TLR3 resulted in abrogated IFN-λ production with no effect on the production of IFN-α. The involvement of TLR3 in vivo supports that the CD8+ and eCD8+ cDCs are the source of IFN-λ because this subset is particularly known for its high expression of TLR3 and to recognize poly IC in a TLR3 dependent fashion (Edwards et al., 2003; Schulz et al., 2005). In contrast, Cardif-deficiency revealed no effects on IFN-λ production but, consistent with previous reports, complete abrogation of serum IFN-α (FIG. 4; Gitlin et al., 2006). Thus, whereas poly IC induced large systemic levels of both IFN-λ and IFN-α in WT mice, the involvement of TLR3 or Cardif seems to be mutually exclusive. A similar involvement of TLR3 but not Cardif or MyD88 for the production of IFN-λ could be detected with eCD8+ cDCs generated in vitro from the corresponding KO mice (FIG. 10 A-C). These findings, together with the observed involvement of FL, strongly suggest that the IFN-λ production to poly IC in vivo largely depends on DCs of the CD8+ and eCD8+ subsets. It has been described that optimal IFN-I production in vivo requires expression of a functional IFN-I receptor (IFN-AR). A role for IFN-AR has also been proposed for the production of IFN-λ in response to either Sendai Virus or Herpes simplex Virus (Ank et al., 2008). Here it was found, in line with the data of Ank and colleagues, that systemic production of IFN-λ and IFN-α in response to poly IC was largely dependent on the presence of IFN-AR (Ank et al., 2008). A similar dependence on the IFN-AR was detected using in vitro generated eCD8+ from either WT or IFN-AR-KO mice (FIG. 10D).

To shed further light on the regulation of IFN-λ production to poly IC in vivo, the response of IFN regulatory factor 7 (IRF7) deficient mice was analyzed. IFN-α production was almost abrogated in IRF7-KO mice (FIG. 4). An essential role for IRF7 has been demonstrated previously for MyD88 dependent IFN-α production by pDC and a participation of IRF7 in TRIF-dependent IFN-I production by DCs has been proposed (Honda et al., 2005; Tamura et al., 2008). It was found that the production of IFN-λ in the serum was largely reduced in the absence of IRF7 indicating a prominent role for IRF7 for the production of IFN-λ by eCD8+ cDCs (FIG. 4). The in vivo findings of a prominent role for IRF7 for the production of IFN-λ in response to poly IC are in line with previous promoter based studies proposing a role of IRF7 in the induction of IFN-α and IFN-λ (Osterlund et al., 2007).

10. Human BDCA3+ DC are Major Producers of IFN-λs upon Poly IC Stimulation

In mice, the separation into several cDC subsets is well established and correlates with subset specific phenotype and function, such as the ability of CD8+ cDCs to produce large amounts of IL-12p70 or to cross-present antigens. Even though the evidence for a similar cDC subset discrimination in human has increased in recent years, this is mainly based on phenotypic similarities with only few functional analogies. It was found that the IFN-λ production in response to poly IC in mice is a CD8+ cDC subset specific feature. It was desirable to establish if this feature correlated to any human DC subsets. Based on phenotypic similarities, such as Clec9a and Necl2 expression, the BDCA3 positive human DCs have been proposed as potential human eCD8+ cDCs. In PBMCs and fractions of DC-enriched PBMCs, it was found that poly IC induced IFN-λ1 (IL-29) and IFN-λ2 (IL-28A). Separation of cDC subsets using the markers BDCA1 or BDCA3 revealed that the BDCA3 positive cells for all donors tested were the major producers of IFN-λ1, as well as IFN-λ2 (FIG. 5). Thus, in terms of IFN-λ production upon poly IC stimulation, the human BDCA3 cDCs functionally resemble the murine eCD8+ cDCs.

11. eCD8+ cDCs are Major Producers of IFN-λ in Response to DNA Viruses

Herpesviridae is a family of double stranded DNA viruses also named herpesviruses which cause persistent recurring infections and in human include important pathogens such as Herpes simplex virus (HSV) 1 and 2; Varicella zoster virus (VZV), human cytomegalovirus (HCMV), Kaposi's sarcoma-associated herpesvirus (KSHV) and Ebstein-Barr virus (EBV). Previously, it was found that HSV-1 is recognized by pDC via TLR9 via a MyD88 dependent way but that it is seen by cDC independent of MyD88 via a up to date unknown recognition pathway (Hochrein et al., 2004). IFN-λ was able to protect against mucosal infection with HSV and TLR dependent protection was largely IFN-λ dependent (Ank et al., 2008).

The family of poxyiridae, also named poxviruses, represent double stranded DNA viruses which can be separated into several subfamilies such as orthopoxviruses, parapoxviruses and others. Among the poxviruses are important pathogens for human and animals such as variola viruses the causative agent of smallpox, cowpoxvirus, camelpox and Vaccinia viruses. Parapoxviruses are important pathogens for cattle and other animals. Orthopoxviruses and parapoxviruses are recognized by DC via TLR9 dependent and independent pathways (Samuelsson et al., 2008; Siegemund et al., 2009). Some poxviruses encode for an IFN-λ binding protein and poxviruses encoding recombinant IFN-λ were highly attenuated, suggesting a role for IFN-λ in the protection against poxvirus infections (Bartlett et al., 2005; Bartlett et al., 2004).

To determine if the eCD8+ cDC are also producers of IFN-λ in response to DNA viruses, response of cDC subsets to HSV-1 and a parapoxvirus, representing the families of Herpesviruses and poxviruses, was tested.

Figure 6:
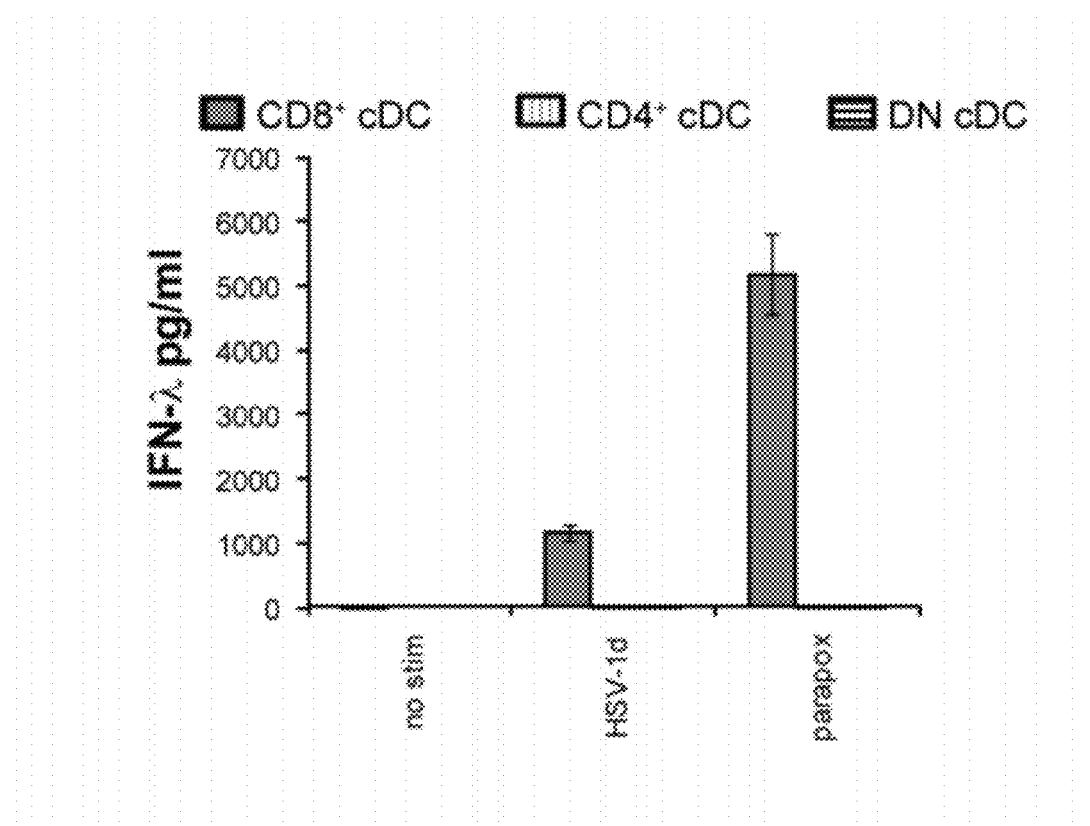
FIG. 6 depicts splenic CD8+ cDC are the major producers of IFN-λ in response to DNA viruses. Highly purified splenic cDC subsets $5 \times 10^5$/ml were stimulated in the presence of IL-3 and GM-CSF with the stimuli as indicated. After 18 h supernatants were analyzed for IFN-λ. Representative results of 3 independent experiments are shown. Data represent mean+/−SD of duplicate samples.

It was found that among ex vivo isolated cDC from spleen the CD8+ cDC were the major producers of IFN-λ in response to either HSV-1 or parapoxvirus (FIG. 6). Using in vitro generated cDC subsets, it was found that again the eCD8+ cDCs were the main producers of IFN-λ to HSV-1 and parapoxvirus. eCD8+ cDCs generated from mutant mice which lacked either Cardif, MyD88 or TLR3 revealed that neither the RLHs nor the TLRs were important for the generation of IFN-λ by eCD8+ cDCs in response to HSV-1 or parapoxvirus.

Since IFN-λs seem to induce antiviral activity against herpesviruses and poxviruses, and based on the novel knowledge of eCD8+ as a major source of IFN-λ this can lead to new therapeutic approaches such as induction of large numbers of eCD8+ cDCs with growth factors e.g. FL or M-CSF-R ligands (M-CSF, IL-34). The viruses themselves can be recognized by the enhanced numbers of eCD8+ cDCs which can induce antiviral IFN-λ, thus restricting the growth of the pathogenic viruses. Alternatively, external stimuli such as mimics for DNA or RNA, e.g. poly IC, can be used to induce the IFN-λ production by eCD8+ cDCs in vivo.

12. eCD8+ cDCs are Major Producers of IFN-λ in Response to RNA Viruses

Since it was found that double stranded (ds) RNA e.g. poly IC is inducing IFN-λ by eCD8+ cDCs, it was next determined if RNA viruses would induce IFN-λ also. It is known that dsRNA is not only present upon infection with dsRNA viruses but that dsRNA intermediates are produced upon infection with single stranded (ss) RNA viruses especially of positive ssRNA viruses. Positive ssRNA families, such as Picornaviruses Flaviviridae, Coronaviridae, Togaviridae, include human and animal pathogens such as West Nile virus, Dengue virus, Hepatitis C virus, SARS, Rubellavirus and others. To test different positive ssRNA viruses representing two different ssRNA virus families, Semliki Forest Virus (SFV) and Mouse Hepatitis Virus (MHV), representing Togaviridae and Coronaviridae respectively, were used.

Among ex vivo isolated cDCs, the IFN-λ response to SFV and MHV was restricted to the CD8+ cDC subset with no production of IFN-λ by the CD8-cDC subsets (FIG. 7A). Similar results were found for in vitro generated eCD8+ cDCs. With eCD8+ cDCs, it was found that the production of IFN-λ to SFV and MHV was still robust in the absence of MyD88, but that the IFN-λ production to those viruses was lost in the absence of TLR3. Thus, eCD8+ cDCs use TLR3 to produce IFN-λ in response to ssRNA viruses, presumably via dsRNA intermediates.

An important role for IFN-λ in the susceptibility and cure against Hepatitis C virus (HCV) has recently been implicated by genomic analysis (Ge et al, 2009; Suppiah et al., 2009; Tanaka et al., 2009; Thomas et al., 2009).

Figure 3:
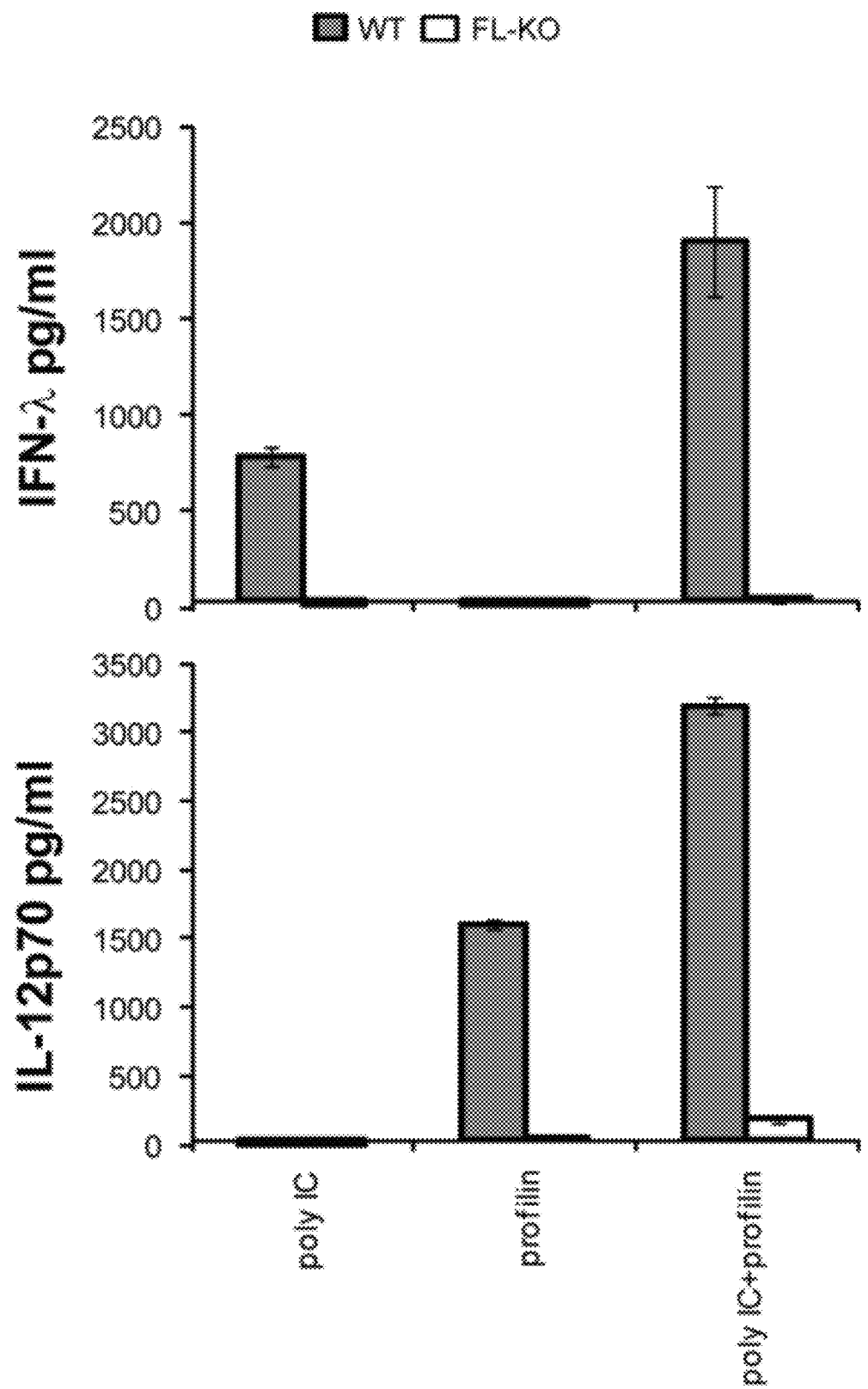
FIGS. 3A and B depict that FL is involved in the production of IFN-λ in vivo. (A) Isolated total non parenchymal liver cells $2.5 \times 10^6$/ml were stimulated in the presence of IL-3+IL-4+IFN-γ+GM-CSF with the stimuli as indicated. After 18 h supernatants were analyzed for IFN-λ and IL-12p70. Representative results of 3 experiments are shown. Data represent mean+/−SD of duplicate samples. (B) WT and FL-KO mice were injected i.v. with 100 μg poly IC. After 3-4 h sera were analyzed for IFN-λ and IFN-α. Circles indicate the results of individual mice and columns represent the mean thereof.
Figure 3:
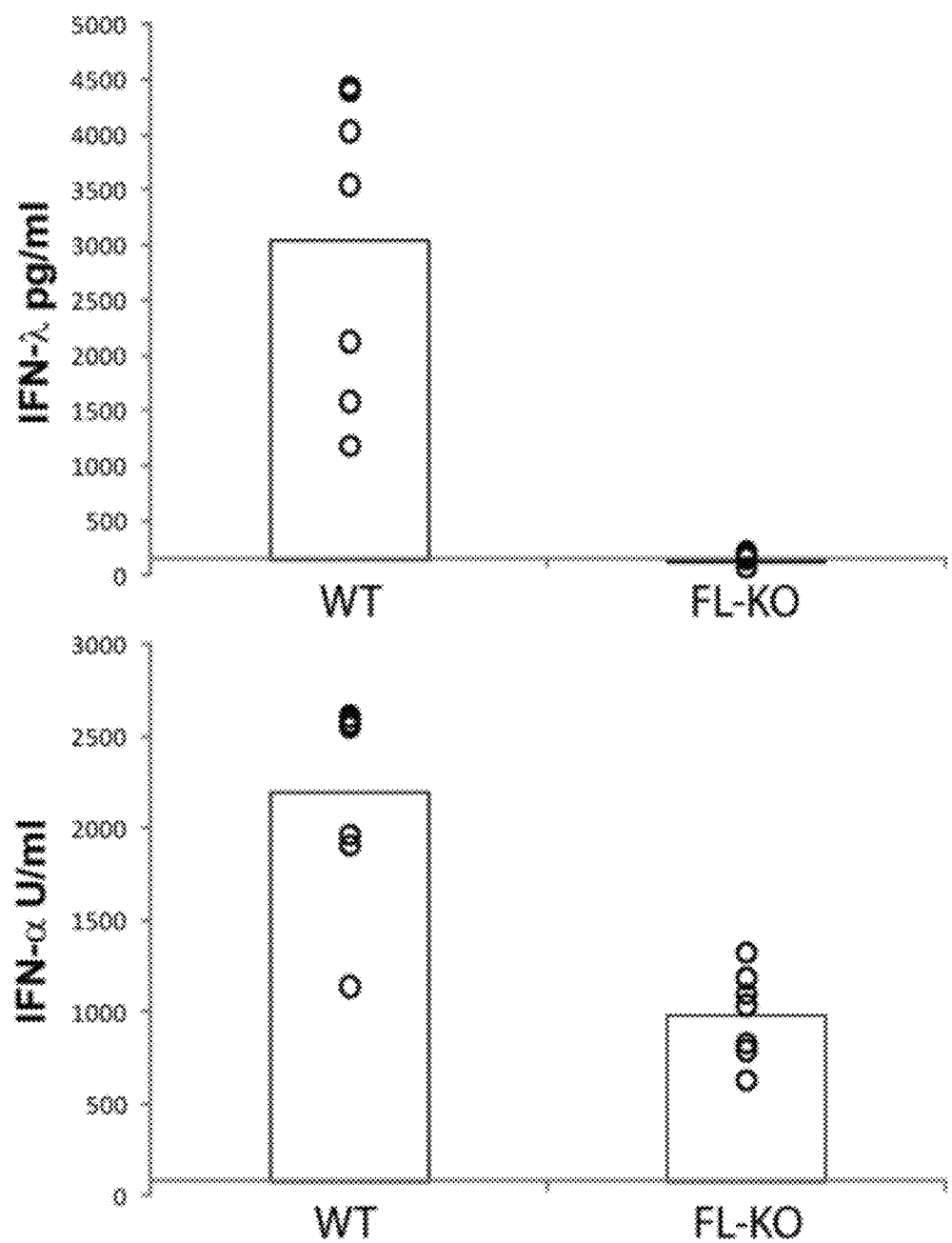
Figure 7:
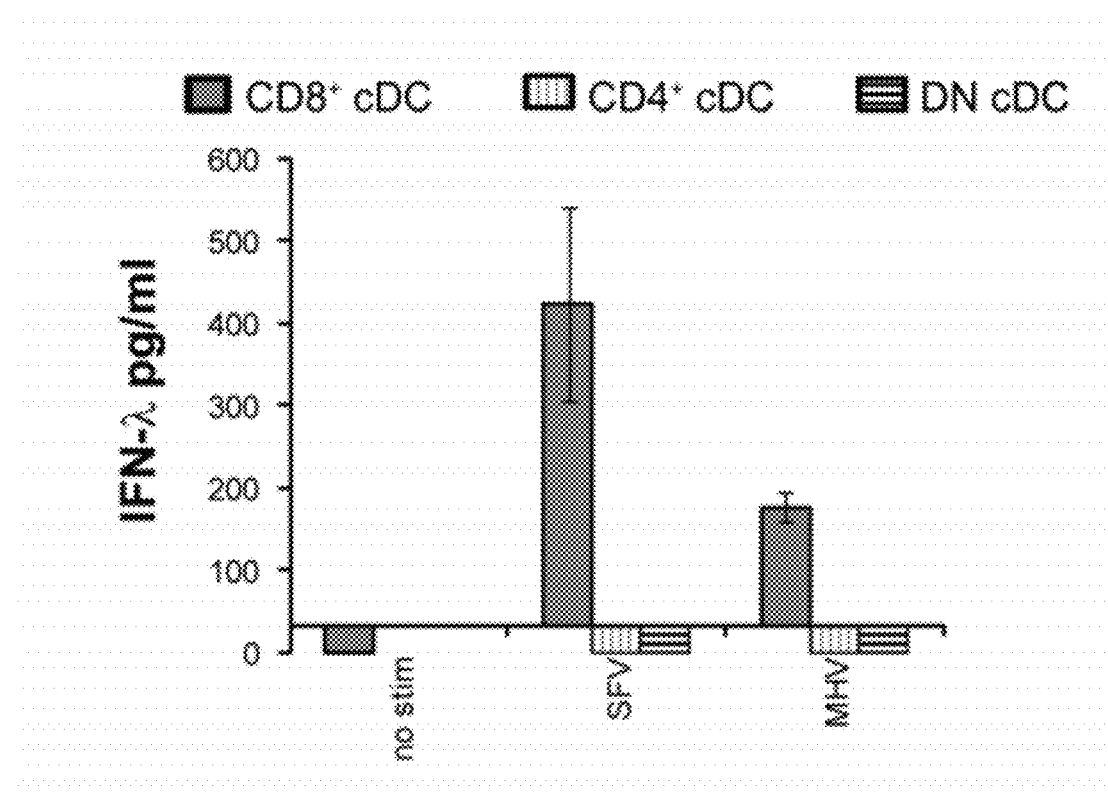
FIG. 7 depicts splenic CD8+ cDCs are the major producers of IFN-λ in response to ssRNA viruses. Highly purified splenic cDC subsets $5 \times 10^5$/ml were stimulated in the presence of IL-3 and GM-CSF with the stimuli as indicated. After 18 h supernatants were analyzed for IFN-λ. Data represent mean+/−SD of duplicate samples.

It was found that the eCD8+ cDCs produce IFN-λ in response to positive ssRNA viruses (FIG. 7). Furthermore, it was found that eCD8+ cDCs can be identified in the liver (FIG. 3 A). Importantly, eCD8+ cDCs do not depend on MyD88 or RLHs for the production of IFN-λ. HCV is known to inhibit signaling of the RLHs and thus inhibits IFN-α production of body cells including CD8-cDCs which rely on RLHs for the recognition of HCV (Meylan et al., 2005). Since it was found that eCD8+ cDCs do not use RLHs but TLR3 for the detection of poly IC and positive ssRNA viruses, this can result in eCD8+ cDCs still able to produce the antiviral cytokine IFN-λ to HCV whereas other cells that rely on RLHs are inhibited. Increasing the amount of eCD8+ cDCs can drastically increase the amount of IFN-λ produced in response to viruses including ssRNA viruses and can be further enhanced by the application of external stimuli such as poly IC or replication deficient DNA viruses (e.g. HSV-1d). The application of eCD8+ cDCs or the in vivo enhancement via growth factors can, with or without combinations with standard therapies such as IFN-I therapy, increase the antiviral response to persistent viruses such as HCV or Herpes viruses.

The production of IFN-λ upon poly IC is a novel hallmark function of eCD8+ cDCs, conserved among evolutionary distant species. It is likely that the production of IFN-λs contributes to the excellent adjuvant effect of poly IC administration. Moreover, CD8+ cDCs and their equivalents, well known for their cross-presentation and IL-12p70 capabilities, are likely contributors to TLR3 mediated anti-viral responses through their high production of IFN-λs. These new findings can be transferred into novel therapeutic approaches which can impact hard to treat persistent infections such as Hepatitis C Virus infections.

13. Poly AU Induction of IFN-λ

Figure 12:
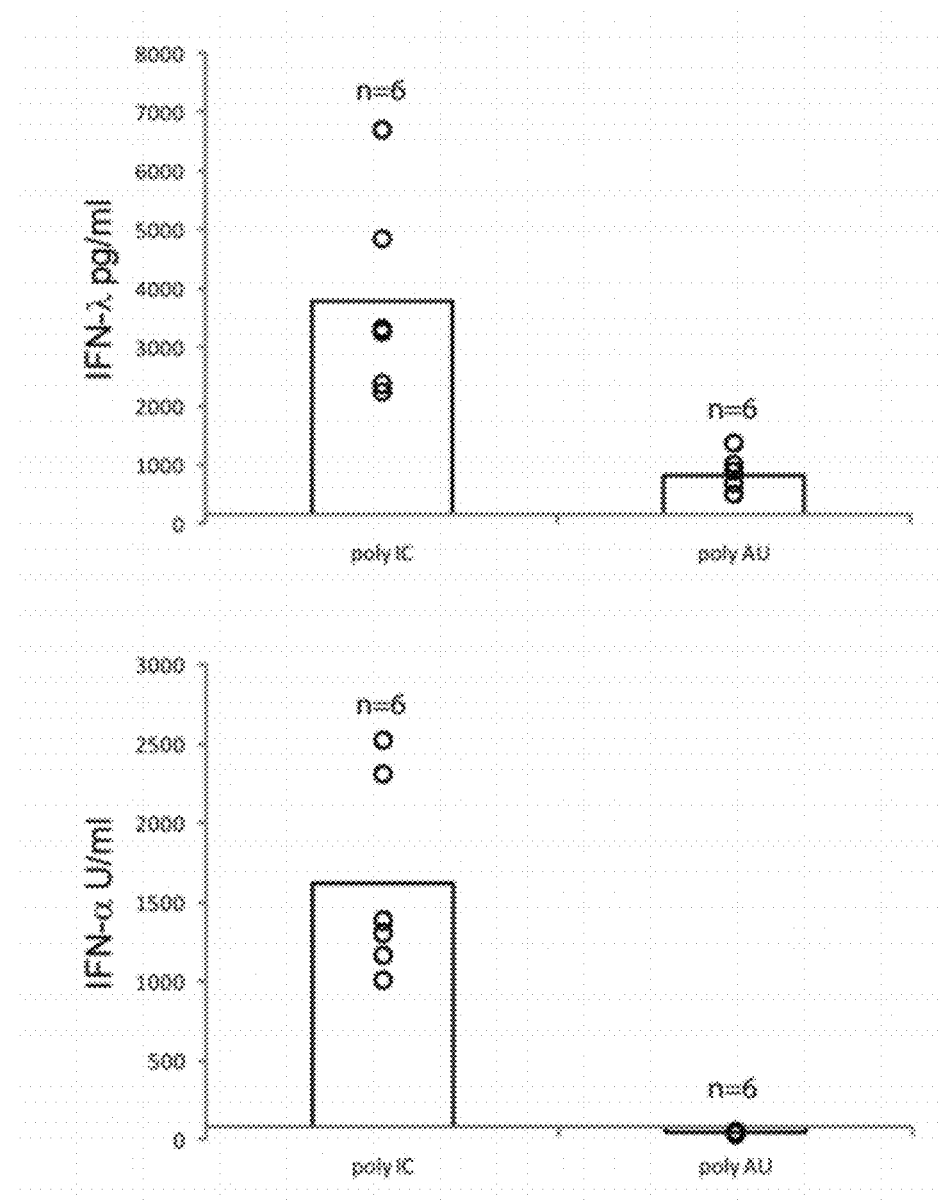
FIG. 12 depicts that poly AU induces IFN-λ but not IFN-α production in vivo. Mice were injected (i.v.) with poly IC (100 µg) or poly AU (100 or 500 µg). After 3-4 h sera were analyzed for IFN-λ and IFN-α. Circles indicate the results of individual mice and their total number (n) is indicated in the graph. The columns represent the mean of all mice used. Two independent experiments have been performed.

Double stranded RNA (dsRNA) is recognized via TLR3 or via Rig-like Helicases (RLH). However, the lengths, the composition or modifications of the RNA can influence the detection via the different RNA receptors. It was seen that in response to polyinosinic:polycytidylic acid (poly IC) the early production of IFN-λ fully depends on the presence of TLR3 and on certain DC subsets (CD8α+ and eCD8α cDCs) whereas the systemic production of IFN-α was independent of TLR3 and independent of CD8α+cDCs but was fully dependent on the RLHs (as seen with Cardif-KO mice which lack an essential adaptor molecule for RLHs). The dsRNA polyadenylic:polyuridylic acid (poly AU) is another form of dsRNA and we tested if poly AU can be used to induce IFN-λ in vivo. Interestingly, poly AU injection induced IFN-λ in the sera of mice, but systemic IFN-λ was not detectable. Thus, using certain form of stimuli it is possible to induce systemic IFN-λ without the induction of systemic IFN-λ (see FIG. 12).

Figure 13:
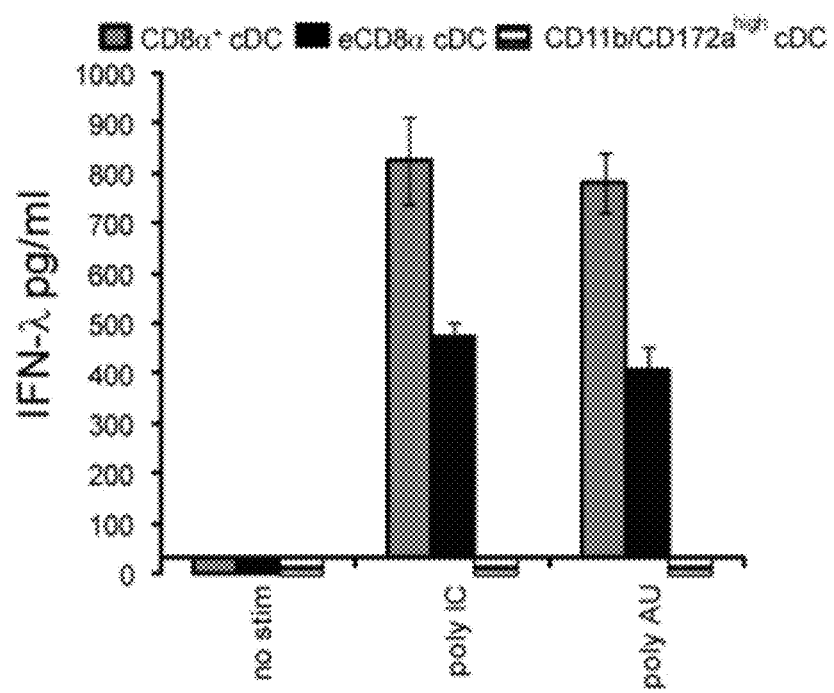
FIG. 13 depicts that in vivo FL expanded CD8α+cDCs and eCD8α cDCs selectively produce IFN-λ to poly AU in vitro. Highly purified FL expanded ex-vivo isolated splenic 5×10$^5$/ml were stimulated in the presence of IL-3+GM-CSF+IL-4+IFN-γ with either poly IC (100 µg/ml) or poly AU (100 µg/ml). After 18 h supernatants were analyzed for IFN-λ.
Figure 15:
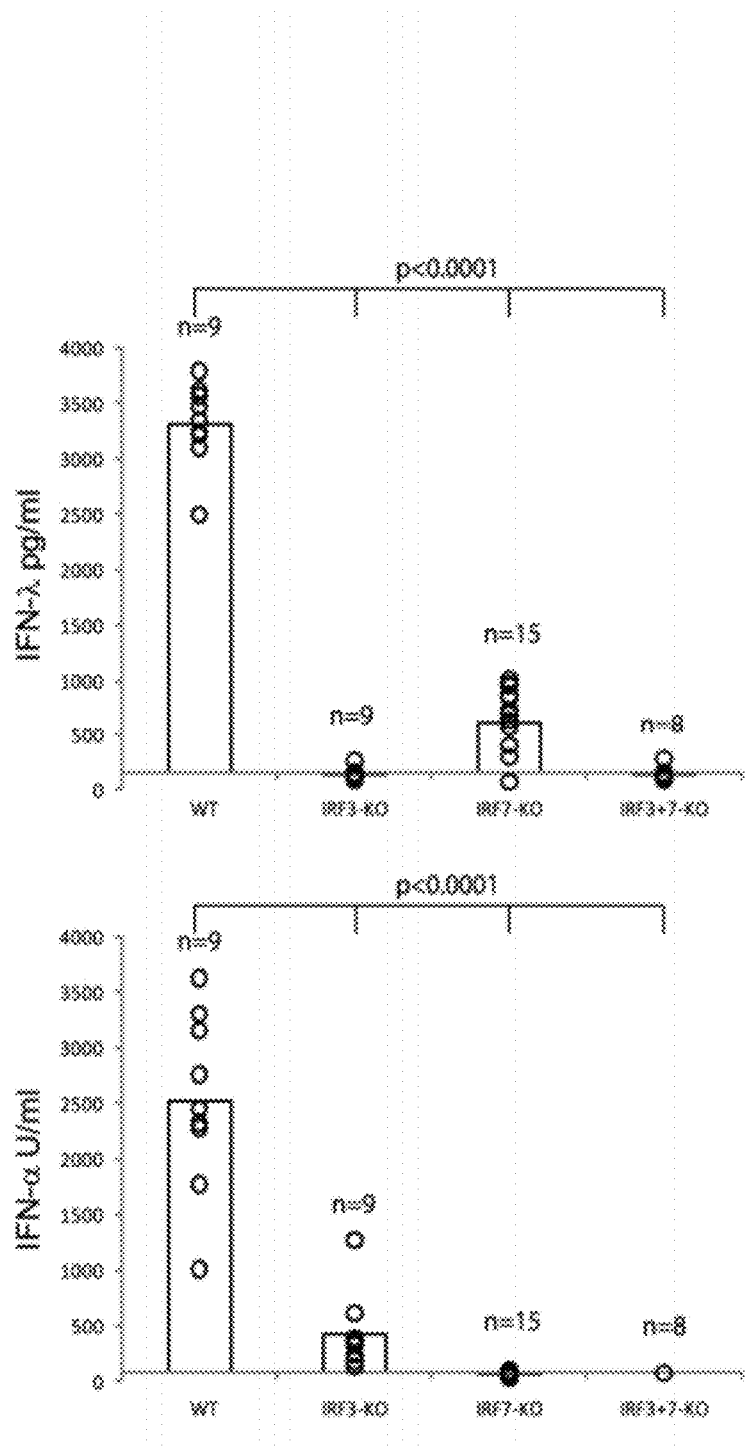
FIG. 15 depicts that IFN-λ production to poly IC in vivo depends on IRF3 and IRF7. Mice with the indicated genotype were injected i.v. with 100 µg poly IC. After 3-4 h sera were analyzed for IFN-λ and IFN-α. Circles indicate the result of individual mice and their total number (n) is indicated in the graph. The columns represent the mean of all mice per genotype. Three independent experiments have been performed.
Figure 16:
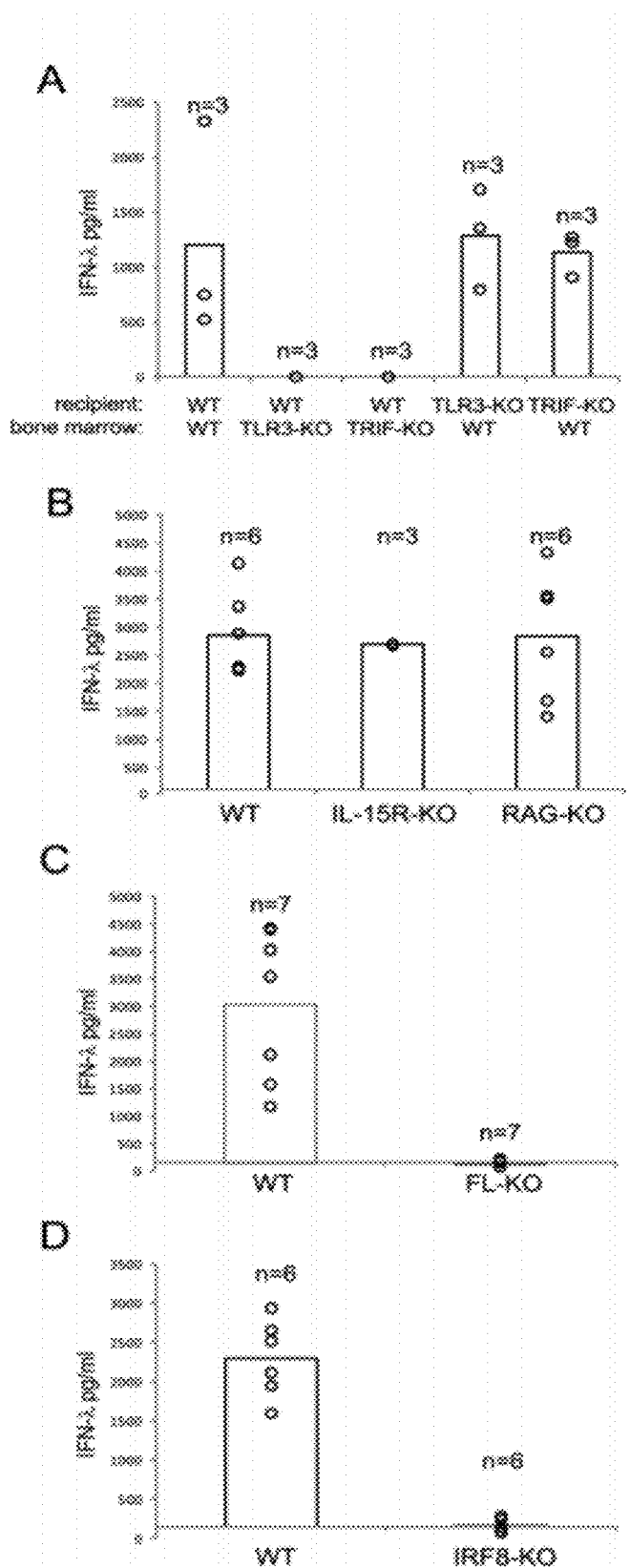
FIG. 16 depicts that IFN-λ production to poly IC in vivo depends on hematopoietic cells, FL and IRF8. Mice with the indicated genotype were injected i.v. with 100 µg poly IC and after 3-4 h sera were analyzed for IFN-λ (A) BM reconstituted mice as indicated; (B) WT, IL-15R-KO and RAG1-KO; (C) WT and FL-KO; (D) WT and IRF8-KO. Circles indicate the result of individual mice and their total number (n) is indicated in the graph. The columns represent the mean of all mice per genotype. (A) one (BM chimeras), (B) two (WT and RAG-KO) or one (IL-15R-KO), (C) three (WT and FL-KO) and (D) two (WT and IRF8-KO) independent experiments have been performed.
Figure 17:
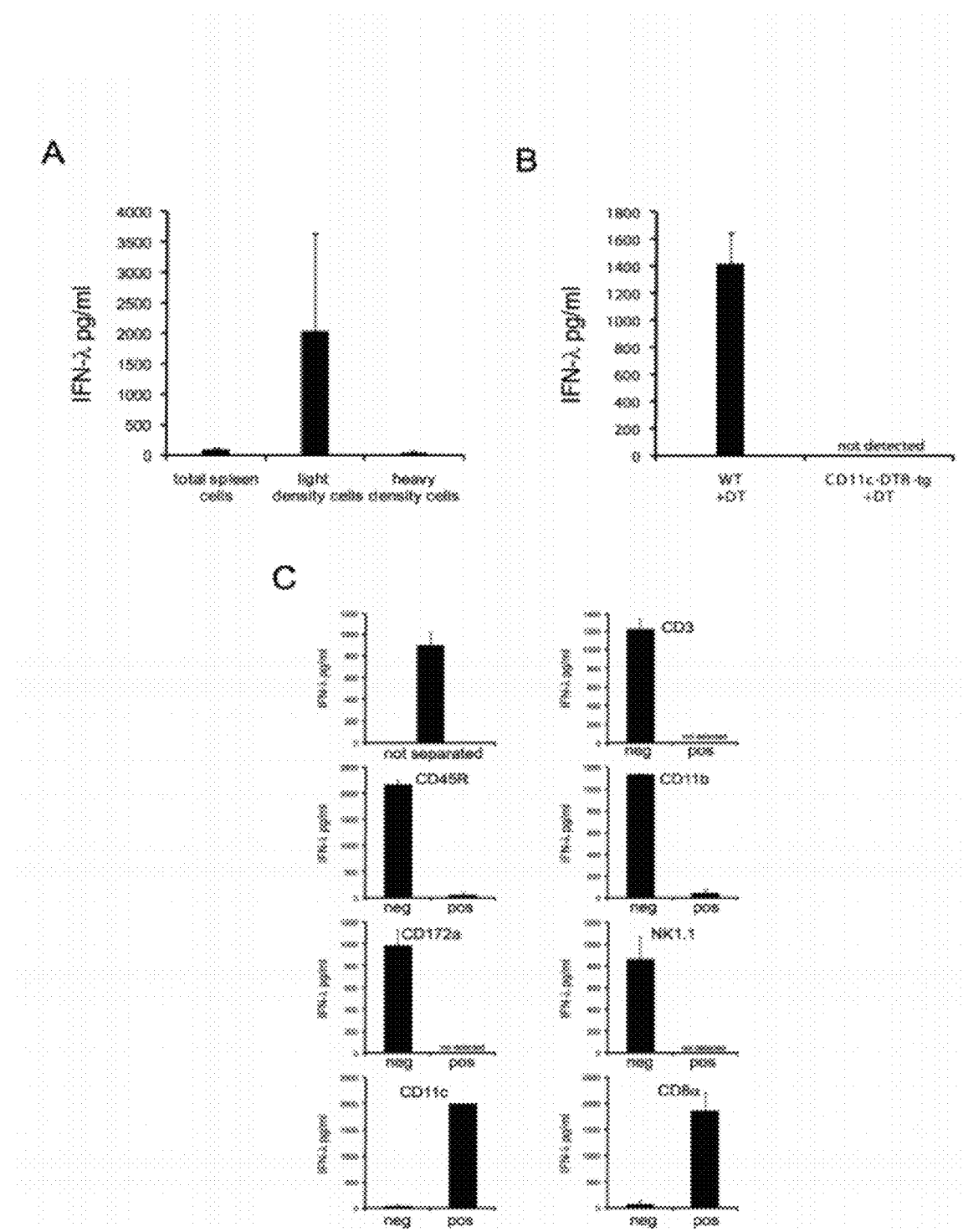
FIG. 17 depicts that IFN-λ production to poly IC injection in vivo separates with CD45R−/CD11c+/CD8α+ splenocytes. 1.5-2 h after i.v. injection of poly IC spleens were harvested and processed. Cell free supernatants were analyzed for IFN-λ after in vitro culture for 18 h. (A) 5×10$^6$ cells/ml total spleen cells or cells separated by density centrifugation into light density cells or heavy density cells. (B) total spleen cells 25×10$^6$ cells/ml of WT or CD11c-DTR-tg mice treated 2 days before with diphtheria toxin (DT). (C) Total spleen cells before separation or after magnetic bead separation into the denoted populations. The initial cell number of splenocytes added onto the column was 20×10$^6$. Without further counting each fraction was distributed into 2 wells with 200 µl medium/well. Bars represent the mean±SD of 2 independent experiments (A+C) or 1 experiment (B) using 2 mice per experiment.
Figure 18:
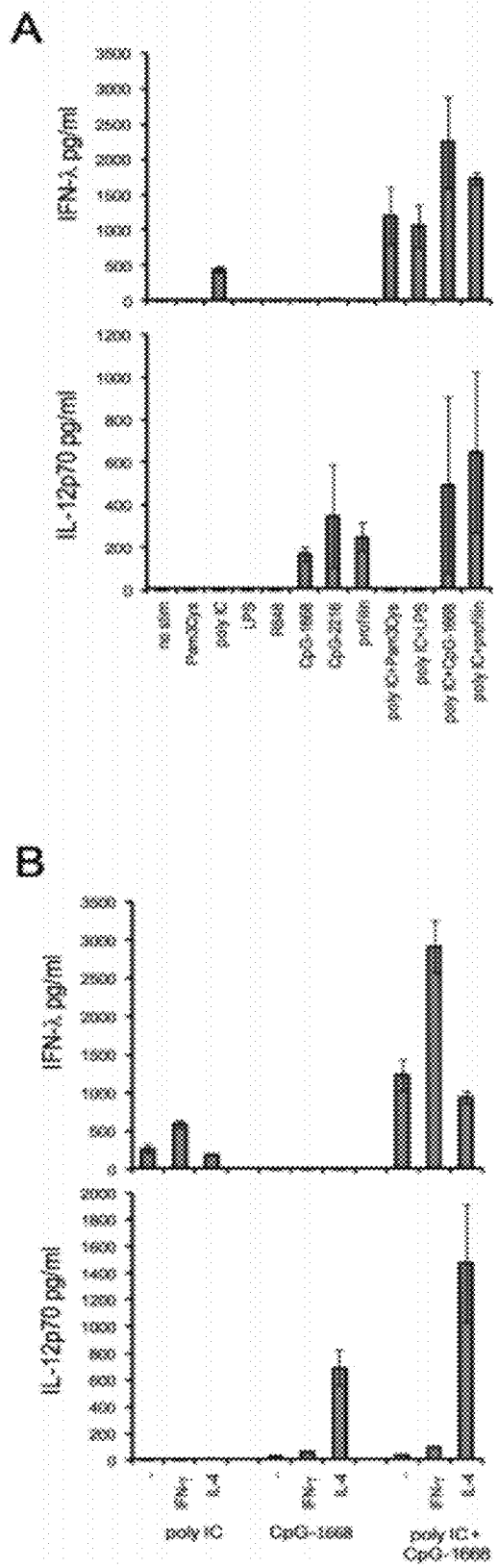
FIG. 18 depicts that the production of IFN-λ or IL-12p70 by CD8α+cDCs depends on the stimuli and the cytokine conditions. Sorted splenic CD8α+ cDCs 5×10$^5$/ml were stimulated and supernatants were analyzed after 18 h for IFN-λ and IL-12p70. (A) Stimulation in the presence of IL-3 and GM-CSF with the stimuli as indicated. (B) Stimuli and cytokines as indicated. Bars represent the mean±SD of 2 independent experiments using a pool of at least 8 mice per experiment.
Figure 19:
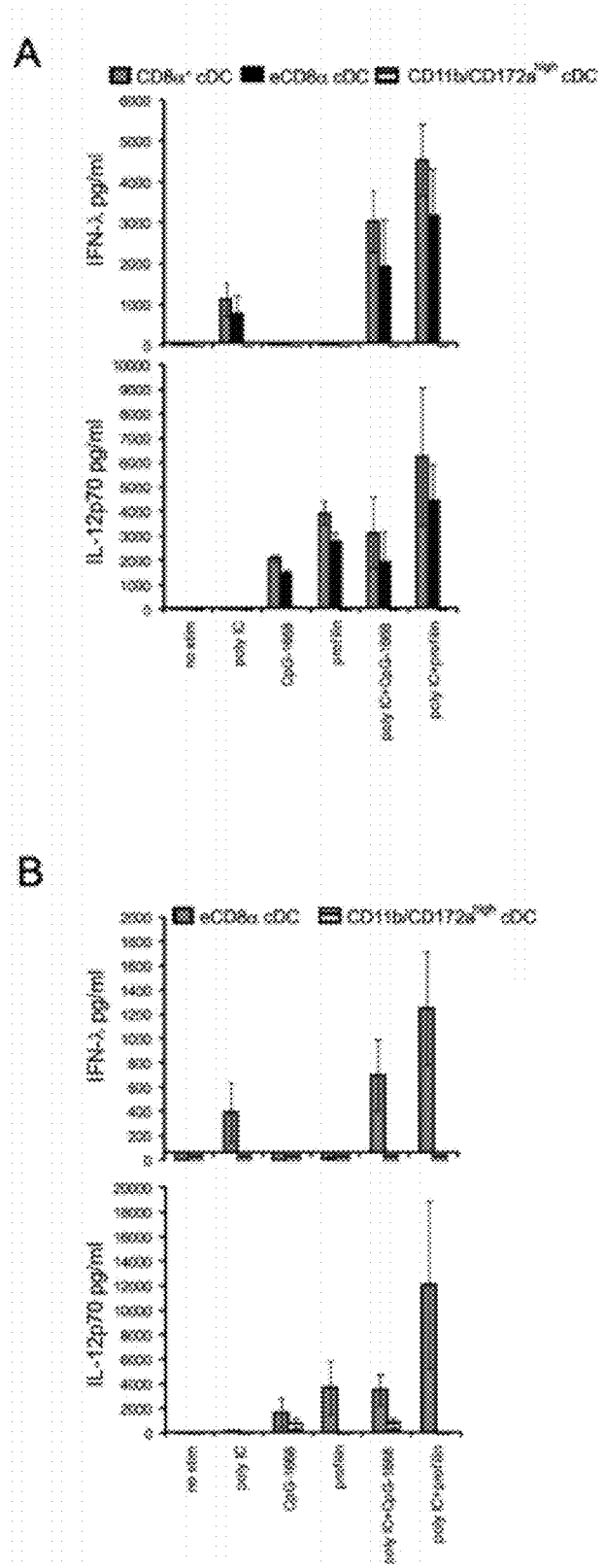
FIG. 19 depicts that in vivo and in vitro FL generated CD8a+ cDCs and eCD8α cDCs are major producers of IFN-λ and IL-12p70. Highly purified (A) FL expanded ex-vivo isolated splenic or (B) generated in vitro from BM with FL cDC subsets 5×10$^5$/ml were stimulated in the presence of IL-3+GM-CSF+IL-4+IFN-γ with the stimuli as indicated. After 18 h supernatants were analyzed for IFN-λ and IL-12p70. Bars represent the mean±SD of 2 independent experiments each using a pool of at least 2 mice per experiment.
Figure 21:
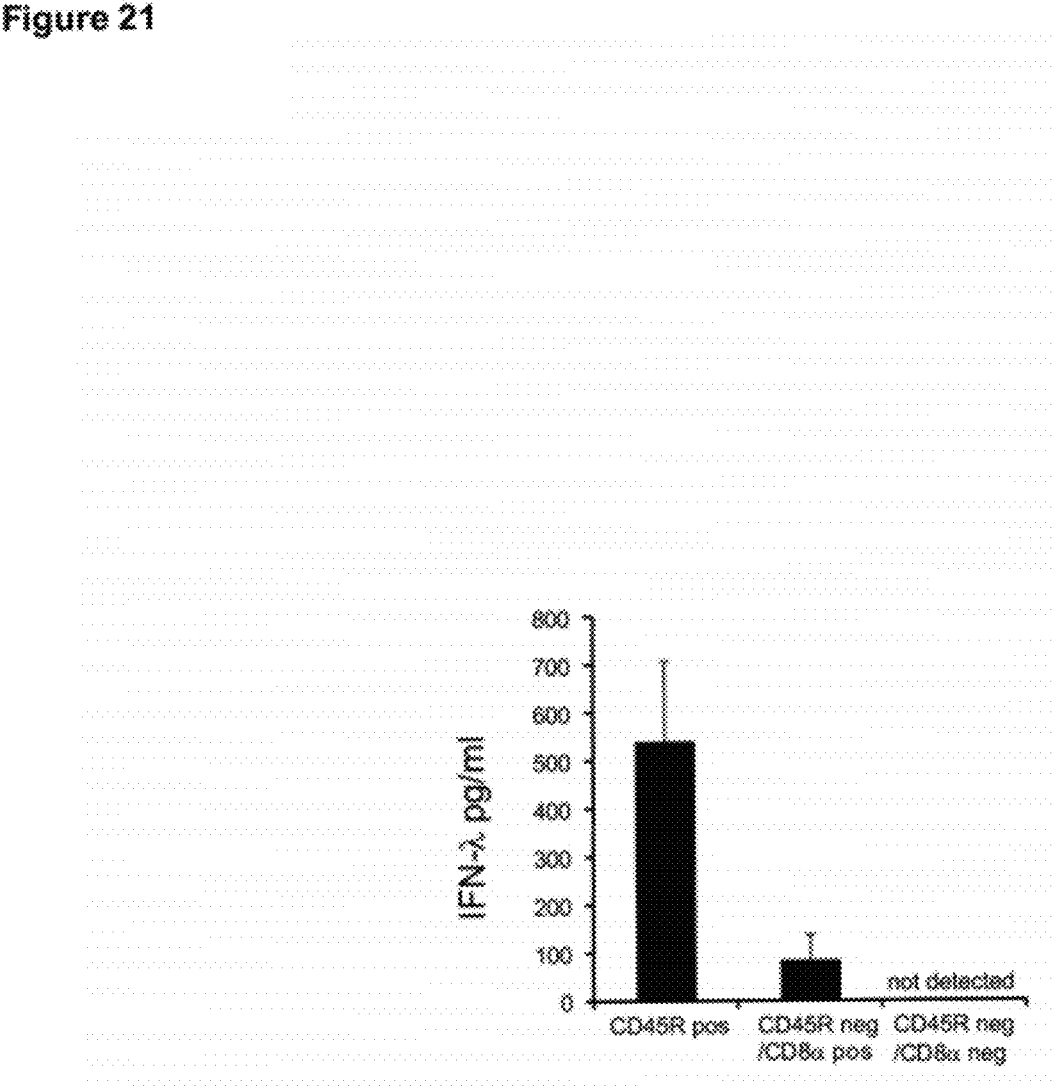
FIG. 21 depicts that the IFN-λ production to HSV-1 injection in vivo separates with CD45R+ and CD45R−/CD8α+ splenocytes. Spleen cells 1.5 h after in vivo injection with DISC HSV-1 were separated with anti-CD45R and magnetic beads into positive and negative fractions. The CD45R negative fraction was further separated into cells positive or negative for CD8α. Separated cells were cultured in vitro for the next 18 h and cell-free supernatants were analyzed for IFN-λ.¯ Bars represent the mean±SD of 2 independent experiments using one mouse per experiment.

To see if the IFN-λ production to poly AU seen in vivo would correspond with the same cells as in response to poly IC we enhanced the amount of DC in mice with FL treatment and sorted CD8α+ cDCs, eCD8α cDCs and CD11b+/CD172a+cDCs. Those cells were stimulated with poly IC or poly AU. Indeed only CD8α+cDCs and eCD8α cDCs but not the other cDCs (CD11b+/CD172a+cDCs) were able to produce IFN-λ to poly IC and to poly AU alike. The results are shown in FIG. 13.

14. Induction of IFN-λ with Poly IC and CD40 Stimulation

Dendritic cells (DC) can be stimulated with pathogen associated molecular pattern (PAMPs) such TLR-ligands and respond with maturation and cytokine production. Beside PAMPS endogenous stimuli exist and one of best described activator mechanism is the interaction of CD40 with its ligand CD40-ligand. DC express CD40 and activated T-cells express CD40-ligand and the interaction of T-cells and DC activates DC. One of the consequences of this activation is the production of cytokines including IL-12p70. Since we found that the combination of IL-12 inducers such as profilin or CpG-ODN together with poly IC induced in vitro a synergistic increase of IFN-λ production we tested if the combination of poly IC and CD40-stimulation would effect the IFN-λ production in vivo. As a stimulus for CD40 a monoclonal antibody (mAb) to CD40, know to be stimulatory in vivo, was used. The results are shown in FIG. 14.

REFERENCES

Adachi et al., 1998. Targeted disruption of the MyD88 gene results in loss of IL-1- and IL-18-mediated function. Immunity 9:143-150.
Alexopoulou et al., 2001. Recognition of double-stranded RNA and activation of NF-kappaB by Toll-like receptor 3. Nature 413:732-738.
Ank et al., 2008. An important role for type III interferon (IFN-lambda/IL-28) in TLR-induced antiviral activity. J. Immunol. 180:2474-2485.
Bartlett et al., 2005. Murine interferon lambdas (type III interferons) exhibit potent antiviral activity in vivo in a poxvirus infection model. J. Gen. Virol. 86:1589-1596.
Bartlett et al., 2004. A new member of the interleukin 10-related cytokine family encoded by a poxvirus. J. Gen. Virol. 85:1401-1412.
Brasel et al., 2000. Generation of murine dendritic cells from flt3-ligand-supplemented bone marrow cultures. Blood 96:3029-3039.
Coccia et al., 2004. Viral infection and Toll-like receptor agonists induce a differential expression of type I and lambda interferons in human plasmacytoid and monocyte-derived dendritic cells. Eur. J. Immunol. 34:796-805.
Diebold et al., 2009. Role of TLR3 in the immunogenicity of replicon plasmid-based vaccines. Gene Therapy. 16:359-366.
Dzionek et al., 2000. BDCA-2, BDCA-3, and BDCA-4: three markers for distinct subsets of dendritic cells in human peripheral blood. J. Immunol. 165:6037-6046.
Edwards et al., 2003. Toll-like receptor expression in murine DC subsets: lack of TLR7 expression by CD8 alpha+ DC correlates with unresponsiveness to imidazoquinolines. Eur. J. Immunol. 33:827-833.
Ge et al., 2009. Genetic variation in IL28B predicts hepatitis C treatment-induced viral clearance. Nature 461:399-401.
Gilliet et al. 2002. The development of murine plasmacytoid dendritic cell precursors is differentially regulated by FLT3-ligand and granulocyte/macrophage colony-stimulating factor. J. Exp. Med. 2002 195(7):953-8.
Gitlin et al., 2006. Essential role of mda-5 in type I IFN responses to polyriboinosinic:polyribocytidylic acid and encephalomyocarditis picornavirus. Proc. Natl. Acad. Sci. USA 103:8459-8464.
Hochrein and O'Keeffe 2008. Dendritic cell subsets and toll-like receptors. Handb. Exp. Pharmacol. 183:153-79.
Hochrein et al., 2000. Interleukin (IL)-4 is a major regulatory cytokine governing bioactive IL-12 production by mouse and human dendritic cells. J. Exp. Med. 192:823-833.
Hochrein et al., 2004. Herpes simplex virus type-1 induces IFN-alpha production via Toll-like receptor 9-dependent and -independent pathways. Proc. Natl. Acad. Sci. USA 101:11416-11421.
Hochrein et al., 2001. Differential production of IL-12, IFN-alpha, and IFN-gamma by mouse dendritic cell subsets. J. Immunol. 166:5448-5455.
Honda et al., 2005. IRF-7 is the master regulator of type-I interferon-dependent immune responses. Nature 434:772-777.
Ishii et al. 2006. A Toll-like receptor-independent antiviral response induced by double-stranded B-form DNA. Nat. Immunol. 7(1):40-48.
Miyake et al., 2009. Poly I:C-Induced Activation of NK Cells by CD8[alpha]+dendritic cells via the IPS-1 and TRIF-dependent pathways. J. Immunol. 183:2522-2528.
Kalinski et al., 2000. IL-4 is a mediator of IL-12p70 induction by human Th2 cells: reversal of polarized Th2 phenotype by dendritic cells. J. Immunol. 165:1877-1881
Kotenko et al., 2003. IFN-lambdas mediate antiviral protection through a distinct class II cytokine receptor complex. Nat. Immunol. 4:69-77.
Luber et al., 2010. Quantitative Proteomics Reveals Subset-Specific Viral Recognition in Dendritic Cells. Immunity 32:279-289.
Li et al., 2009. Interferon-lambdas: the modulators of antivirus, antitumor, and immune responses. J. Leukoc. Biol. 86:23-32.
Longhi et al., 2009, Dendritic cells require a systemic type I interferon response to mature and induce CD4+Th1 immunity with poly IC as adjuvant. J. Exp. Med. 206(7):1589-1602.
McCartney et al., 2009. Distinct and complementary functions of MDA5 and TLR3 in poly(I:C)-mediated activation of mouse NK cells. J Exp Med. 206(13):2967-76.
McKenna et al., 2000. Mice lacking flt3 ligand have deficient hematopoiesis affecting hematopoietic progenitor cells, dendritic cells, and natural killer cells. Blood 95:3489-3497.
Meylan et al., 2005. Cardif is an adaptor protein in the RIG-I antiviral pathway and is targeted by hepatitis C virus. Nature 437:1167-1172.
Muller et al., 1994. Functional role of type I and type II interferons in antiviral defense. Science 264:1918-1921.

Naik et al., 2005. Cutting edge: generation of splenic CD8+ and CD8– dendritic cell equivalents in Fms-like tyrosine kinase 3 ligand bone marrow cultures. J. Immunol. 174: 6592-6597.

Naik 2008. Demystifying the development of dendritic cell subtypes, a little. Immunol. Cell. Biol. 86(5):439-52.

Napolitani et al., 2005. Selected Toll-like receptor agonist combinations synergistically trigger a T helper type 1-polarizing program in dendritic cells. Nat. Immunol. 6:769-776.

O'Keeffe et al., 2002. Effects of administration of progenipietin, Flt-3 ligand, G-CSF and pegylated GM-CSF on dendritic cell subsets in mice. Blood. 99:2122-2130.

Onoguchi et al., 2007. Viral infections activate types I and III interferon genes through a common mechanism. J. Biol. Chem. 282:7576-7581.

Osterlund et al., 2005. Gene expression and antiviral activity of alpha/beta interferons and interleukin-29 in virus-infected human myeloid dendritic cells. J. Virol. 79:9608-9617.

Osterlund et al., 2007. IFN regulatory factor family members differentially regulate the expression of type III IFN (IFN-lambda) genes. J. Immunol. 179:3434-3442.

Pillarisetty, et al., 2004. Liver dendritic cells are less immunogenic than spleen dendritic cells because of differences in subtype composition. J. Immunol. 172:1009-1017.

Reis e Sousa et al., 1997. In vivo microbial stimulation induces rapid CD40 ligand-independent production of interleukin 12 by dendritic cells and their redistribution to T cell areas. J. Exp. Med. 186:1819-1829.

Robbins et al., 2008. Novel insights into the relationships between dendritic cell subsets in human and mouse revealed by genome-wide expression profiling. Genome Biol. 9:R17.

Samuelsson et al., 2008. Survival of lethal poxvirus infection in mice depends on TLR9, and therapeutic vaccination provides protection. J. Clin. Invest. 118:1776-1784.

Schulz et al., 2005. Toll-like receptor 3 promotes cross-priming to virus-infected cells. Nature 433:887-892.

Sheppard et al., 2003. IL-28, IL-29 and their class II cytokine receptor IL-28R. Nat. Immunol. 4:63-68.

Shortman et al., 2009. Improving vaccines by targeting antigens to dendritic cells. Exp. Mol. Med. 41:61-66.

Siegemund et al., 2009. Conventional bone marrow-derived dendritic cells contribute to toll-like receptor-independent production of alpha/beta interferon in response to inactivated parapoxvirus ovis. J. Virol. 83:9411-9422.

Sommereyns et al., 2008. IFN-lambda (IFN-lambda) is expressed in a tissue-dependent fashion and primarily acts on epithelial cells in vivo. PLoS. Pathog. 4:e1000017.

Suppiah 2009. IL28B is associated with response to chronic hepatitis C interferon-alpha and ribavirin therapy. Nat. Genet. 41:1100-1104.

Tamura et al., 2008. The IRF family transcription factors in immunity and oncogenesis. Annu. Rev. Immunol. 26:535-584.

Tanaka et al., 2009. Genome-wide association of IL28B with response to pegylated interferon-alpha and ribavirin therapy for chronic hepatitis C. Nat. Genet. 41:1105-1109.

Thomas et al., 2009. Genetic variation in IL28B and spontaneous clearance of hepatitis C virus. Nature 461:798-801.

Vandenabeele et al., 2001. Human thymus contains 2 distinct dendritic cell populations. Blood 97:1733-1741.

Vremec et al., 2007. Production of interferons by dendritic cells, plasmacytoid cells, natural killer cells, and interferon-producing killer dendritic cells. Blood 109:1165-1173.

Wang et al., 2002. Noncoding RNA danger motifs bridge innate and adaptive immunity and are potent adjuvants for vaccination. J. Clin. Invest. 110(8):1175-84.

Yarovinsky et al., 2005. TLR11 activation of dendritic cells by a protozoan profilin-like protein. Science 308:1626-1629.

The invention claimed is:

1. An in vitro method for producing interferon-lambda (IFN-λ), comprising the steps of:
    (a) contacting a first population of cells comprising dendritic cells or dendritic precursor cells with an agent that increases the level of CD8+ and/or eCD8+ conventional dendritic cells (cDCs);
    (b) isolating a second population of cells comprising more than 50% CD8+ and/or eCD8+ cDCs;
    (c) contacting the second population of cells with a double-stranded (ds) nucleic acid or analog thereof in an amount sufficient to induce IFN-λ production in CD8+ or eCD8+ cDCs, and
    (d) generating a population of IFN-λ producing CD8+ or eCD8+ cDCs, wherein said eCD8+ cDCs express Clec9a and/or Necl2.

2. The method of claim 1, wherein the agent that increases the level of CD8+ and/or eCD8+ is Flt3-ligand (FL) or macrophage-colony stimulating factor (M-CSF) receptor ligand.

3. The method of claim 2, wherein the population of IFN-λ producing CD8+ or eCD8+ cDCs is further incubated with an enhancer of IFN-λ production.

4. The method of claim 3, wherein the enhancer of IFN-λ production is a Toll-like receptor (TLR) ligand, a tumor necrosis factor (TNF) family member, or a cytokine.

5. The method of claim 4, wherein the TLR-ligand is a TLR2 ligand, a TLR4 ligand, a TLR9 ligand, a TLR10 ligand, or a TLR11 ligand.

6. The method of claim 4, wherein the TNF-family member is a CD40-ligand.

7. The method of claim 4, wherein the cytokine is interleukin 3 (IL-3), granulocyte macrophage-colony stimulating factor (GM-CSF), interleukin 4 (IL-4), or interferon gamma (IFN-γ).

8. An in vitro method for producing interferon-lambda (IFN-λ), comprising the steps of:
    (a) providing a population of dendritic cell precursor cells;
    (b) contacting the dendritic cell precursor cells with Flt3-ligand (FL) or macrophage-colony stimulating factor (M-CSF) receptor ligand;
    (c) isolating a population of cells comprising more than 50% CD8+ and/or eCD8+ conventional dendritic cells (cDCs);
    (d) contacting the population of cells comprising more than 50% CD8+ and/or eCD8+ cDCs with a double-stranded (ds) nucleic acid or analog thereof in an amount sufficient to induce IFN-λ production in CD8+ or eCD8+ cDCs, and
    (e) generating a population of IFN-λ producing CD8+ or eCD8+ cDCs, wherein said eCD8+ cDCs express Clec9a and/or Necl2.

9. The method of claim 8, wherein the population of IFN-λ producing CD8+ or eCD8+ cDCs is further incubated with an enhancer of IFN-λ production.

10. The method of claim 9, wherein the enhancer of IFN-λ production is a Toll-like receptor (TLR) ligand, a tumor necrosis factor (TNF) family member, or a cytokine.

11. The method of claim 10, wherein the TLR-ligand is a TLR2 ligand, a TLR4 ligand, a TLR9 ligand, a TLR10 ligand or a TLR11 ligand.

12. The method of claim 10, wherein the TNF-family member is a CD40-ligand.

13. The method of claim 10, wherein the cytokine is interleukin 3 (IL-3), granulocyte macrophage-colony stimulating factor (GM-CSF), interleukin 4 (IL-4), or interferon gamma (IFN-γ).

14. An in vitro method for producing interferon-lambda (IFN-λ), comprising the steps of:
   (a) providing a population of cells comprising more than 50% CD8+ and/or eCD8+ conventional dendritic cells (cDCs);
   (b) contacting the cDCs with a double-stranded (ds) nucleic acid or analog thereof in an amount sufficient to induce IFN-λ production in CD8+ or eCD8+ cDCs, and
   (c) generating a population of IFN-λ producing CD8+ or eCD8+ cDCs, wherein said eCD8+ cDCs express Clec9a and/or Necl2.

15. The method of claim 14, wherein the population of IFN-λ producing CD8+ or eCD8+ cDCs is further incubated with an enhancer of IFN-λ production.

16. The method of claim 15, wherein the enhancer of IFN-λ production is a Toll-like receptor (TLR) ligand, a tumor necrosis factor (TNF) family member, or a cytokine.

17. The method of claim 16, wherein the TLR-ligand is a TLR2 ligand, a TLR4 ligand, a TLR9 ligand, a TLR10 ligand or a TLR11 ligand.

18. The method of claim 16, wherein the TNF-family member is a CD40-ligand.

19. The method of claim 16, wherein the cytokine is interleukin 3 (IL-3), granulocyte macrophage-colony stimulating factor (GM-CSF), interleukin 4 (IL-4), or interferon gamma (IFN-γ).

* * * * *